(12) United States Patent
Fahim et al.

(10) Patent No.: US 8,536,403 B2
(45) Date of Patent: Sep. 17, 2013

(54) WHEAT PLANTS WITH IMMUNITY TO WHEAT STREAK MOSAIC VIRUS (WSMV)

(75) Inventors: Muhammad Fahim, Acton (AU); Philip John Larkin, Weston (AU); Ligia Isabel Ayala-Navarrete, Page (AU); Anthony Alan Millar, O'Connor (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 12/807,969

(22) Filed: Sep. 17, 2010

(65) Prior Publication Data

US 2011/0154534 A1    Jun. 23, 2011

Related U.S. Application Data

(60) Provisional application No. 61/276,867, filed on Sep. 17, 2009.

(51) Int. Cl.
| | | |
|---|---|---|
| *C12N 15/113* | (2010.01) | |
| *C12N 15/82* | (2006.01) | |
| *C12N 5/10* | (2006.01) | |
| *A01H 5/00* | (2006.01) | |
| *A01H 4/00* | (2006.01) | |
| *B02B 3/00* | (2006.01) | |
| *B02B 5/00* | (2006.01) | |

(52) U.S. Cl.
USPC .......... 800/279; 435/430; 536/24.1; 800/285; 800/320.3; 99/600

(58) Field of Classification Search
USPC ....................................... 800/279
See application file for complete search history.

(56) References Cited

U.S. PATENT DOCUMENTS

2008/0104732 A1*  5/2008  Waterhouse et al. ......... 800/281

OTHER PUBLICATIONS

Sivamani et al. (Transgenic Res. (2002) 11: 31-41.*
Niu et al. (Nature Biotechnol. (2006) 24: 1420-1428.*
Wang et al. (RNA (2008) 14: 903-913.*
Komari et al. (Plant J. (1996) 10: 165-174.*
Yang et al. (Nucleic Acids Res. (2006) 34: 667-675.*
Dupre et al. (2002) Barley Yellow Dwarf disease: recent advances and future strategies, pp. 27-28.*
Choi et al. (2000) NCBI Acession No. AF285170.1.*
Golnik et al. (2009) GenBank Accession No. FJ666337.1.*

* cited by examiner

*Primary Examiner* — David T Fox
*Assistant Examiner* — Steven Bernacki
(74) *Attorney, Agent, or Firm* — John P. White; Gary J. Gershik; Cooper & Dunham LLP

(57) ABSTRACT

The present invention provides a transgenic wheat cell or wheat plant, the wheat cell or wheat plant comprising a chimeric DNA molecule which encodes a dsRNA molecule which is capable of inhibiting wheat streak mosaic virus (WSMV) replication, wherein the wheat cell or plant is immune to WSMV. The present invention also provides a chimeric DNA, the chimeric DNA comprising (i) a wheat expressible promoter; (ii) a region which encodes a dsRNA which is capable of inhibiting WSMV replication; and (iii) a transcription termination and polyadenylation signal. Finally, the present invention provides a process for producing the aforementioned transgenic wheat cell or plant, comprising (i) introducing a chimeric DNA molecule comprising (a) a wheat expressible promoter; (b) a region which encodes a dsRNA which is capable of inhibiting WSMV replication; and (c) a transcription termination and polyadenylation signal into a parental wheat cell; and optionally (ii) regenerating a wheat plant from the wheat cell comprising the chimeric DNA molecule; and (iii) identifying and/or selecting a plant which is immune to WSMV.

19 Claims, 35 Drawing Sheets

Figure 8. Multiple sequence alignment of WSMV strains using ClustalW (AlignX /Vector NTI 10)

Figure 10A. Natural miR395 sequence (truncated) encoding five native miRNAs in rice.

AGTCAAAATTTGGTTGTTGTCCACTGAGTTCTCCTCAATCCACTTCAGTAGATAGCTATGCCTAGGCCTCATTGCATTGCACTGTTACATAACT
GTGATCATGGGCCAAAAGCTAGCTATGTATAGTGAAGTGCTTGGGGAACTCCAGTTGACACTCAGCATTTCAAGTTAGTATGTAAGTGCTTG
TACTTTATGAATTTGTAAGTGACAGAGAATGATTAGGTTTGGAGTCCCTAGGAGTCCTTTCAAGCACTTTACGACACACTGTATTGAGAGTTGTC
GTGAAGTGTTTTGGGGAACTCTAGTGTCTCGCCAAGCATTTAAGCCATTATTTATAGGGTTGTTGTGAAGTGTTGGAGGAACTCTCGGTGTCATCAAACAATTAGTAGATAGTG
TTCTCTTTAAGCACTTCATACGACACCAACGTTTGGTATTGTCGTGAGTTCCTTCAAGCACTTCAGTGGCACTATCTCAATGCCTACTATGTGAAGTGT
TTTAAACCACAAGACTGAGAGCCACGTTTCAAGGCCTATTGTCGGCCCTATTGTTAAACACGAGATTGAGATGGGAGCCACTTTGTTATTATCGAGAGTTCCTTT
CAACCACTTCAGTGGCCAGTGCCACTGTTTCAAGGCCTATTGTGAAGTGTTTTGGGGAACTCGATATCACCAAACATTTAATGTAGTGCTTAAACCAC
AA

Figure 10B. Modified miR395 sequence encoding five amiRNAs targeting WSMV

AGTCAAAATTTGGTTGTTGTCCACTGAGTTCTATCCTCAGTGCTTATTCTCTATGCGAGAGCTGTA

WHEAT PLANTS WITH IMMUNITY TO WHEAT STREAK MOSAIC VIRUS (WSMV)

This application claims benefit of U.S. Provisional Application No. 61/276,867, filed Sep. 17, 2009, the contents of which are hereby incorporated by reference.

This application incorporates-by-reference nucleotide and/or amino acid sequences which are present in the file named 120814_0683_80892_A_SEQUENCELISTING_REB.TXT", which is 79.7 kilobytes in size, and which was created Aug. 14, 2012 in the IBM-PC machine format, having an operating system compatibility with MS-Windows, which is contained in the text file filed Aug. 14, 2012 as part of this application.

FIELD

The present invention relates to transgenic wheat plants which are immune to wheat streak mosaic virus. The present invention further relates to genetic constructs for use in producing immune wheat plants and to methods of developing immune wheat plants.

BACKGROUND

Wheat streak mosaic virus (WSMV), vectored by Wheat curl mite (WCM), causes disease of wheat plants of great economic importance in the USA and Canada. Recently, the virus has been identified in Australia. In a short span of time, the virus has spread to all major wheat growing areas. WSMV, a tritimovirus of the Family Potyviridae has a monopartite genome of single-stranded RNA (ssRNA) with messenger polarity and a genome size that varies from 9,339 to 9,384 nucleotides depending upon the isolate (Choi et al., 2001; Rabenstein et al., 2002; Stenger et al., 1998). The host range of WSMV is restricted to species in the family Gramineae and it is naturally transmitted by the wheat curl mite Aceria tosichella Keifer (Harvey and Seifers, 1991; Seifers et al., 1998; Slykhuis, 1955).

Wheat Streak Mosaic disease is one of the most destructive viral diseases of wheat (Conner et al., 1991; Jiang et al., 1993; Makkouk and Kumari, 1997; Nyitrai, 1991). For instance, in the Great Plains of North America endemics may cause yield losses up to 100% (French and Stenger, 2003; Stenger et al., 2002). In Australia, WSMV was first identified in 2003 in South Australia, Victoria, New South Wales and Queensland, followed by Western Australia in 2006 and more recently in Tasmania (Dwyer et al., 2007; Ellis et al., 2003; Ellis et al., 2004), with losses reaching 80% in some instances (Dwyer et al., 2007; Murray et al., 2007).

Two sources of natural resistance have been described to date in wheat and in its wild relatives but have proved to be temperature sensitive (Seifers et al., 1995; 2006) and of limited usefulness. One of those sources, a Thinopyrum intermedium chromosomal translocation to wheat, can incur a significant yield penalty in the absence of the virus (Baley et al., 2001; Divis et al., 2006; Sharp et al., 2002). The other resistance has been released once in the wheat cultivar RonL (Seifers et al., 2007). Synthetic resistance has been reported (Li et al., 2005) using a coat protein gene of WSMV. However, the resistance was only partial—the plants were not immune to the virus—and was unstable in later generations of the transgenic plants. Since all viruses included in the Potyviridae are thought to encode suppressors of gene silencing, the loss of transgene silencing and the observed unstable resistance may have been associated with suppression of silencing.

There is therefore a need to create improved sources of resistance to minimize losses, especially for environments with higher early season temperatures where the existing resistances break down.

SUMMARY OF THE INVENTION

In a first aspect the present invention provides a transgenic wheat cell or wheat plant, the wheat cell or wheat plant comprising a chimeric DNA molecule which encodes a dsRNA molecule which is capable of inhibiting wheat streak mosaic virus (WSMV) replication, wherein the wheat cell or plant is immune to WSMV.

In a second aspect the present invention provides a chimeric DNA, the chimeric DNA comprising (i) a wheat expressible promoter; (ii) a region which encodes a dsRNA which is capable of inhibiting WSMV replication; and (iii) a transcription termination and polyadenylation signal.

In a third aspect the present invention provides a process for producing the transgenic wheat cell or plant of the first aspect of the present invention, comprising
  i) introducing a chimeric DNA molecule comprising (i) a wheat expressible promoter; (ii) a region which encodes a dsRNA which is capable of inhibiting WSMV replication; and (iii) a transcription termination and polyadenylation signal into a parental wheat cell; and optionally
  ii) regenerating a wheat plant from the wheat cell comprising the chimeric DNA molecule; and
  iii) identifying and/or selecting a plant which is immune to WSMV.

In order that the nature of the present invention may be more fully understood various forms thereof will now be described with reference to the following Figures and Examples.

BRIEF DESCRIPTION OF THE FIGURES

FIG. 8. (Panels a to w) Sequence alignment of multiple WSMV strains using ClustalW (AlignX/Vector NTI 10). The sequences are as described in Example 6, and are SEQ ID NOs: 26, 27, 28, 29, 1 and 30 ordered from top to bottom, respectively. A concensus sequence derived from the five sequences is also shown below each panel. Each "N" in the concensus represents any nucleotide; these are indicated where the five strains comprise any one of at least three different nucleotides.

FIG. 9. Schematic diagram of the structure of WSMV genomic RNA, indicating the different protein encoding regions of WSMV, and the positions of the three miRNA sequences within the genome, or in the cases of WEB88 and WEB89, the positions of the identical sequences on the genomic RNA of WSMV. See Example 6 for further explanation.

FIG. 10. Shown are (A) the nucleotide sequences of the DNA encoding the truncated mi395 gene of rice (SEQ ID NO: 31) and (B) the chimeric DNA encoding the five artificial miRNAs (SEQ ID NO: 32) constructed as described in Example 6. The sequences highlighted in dark gray correspond to the miRNA sequences, whereas the sequences highlighted in light gray correspond to the complementary sequences to each of the miRNA sequences.

DETAILED DESCRIPTION

General Techniques

Figure 1:
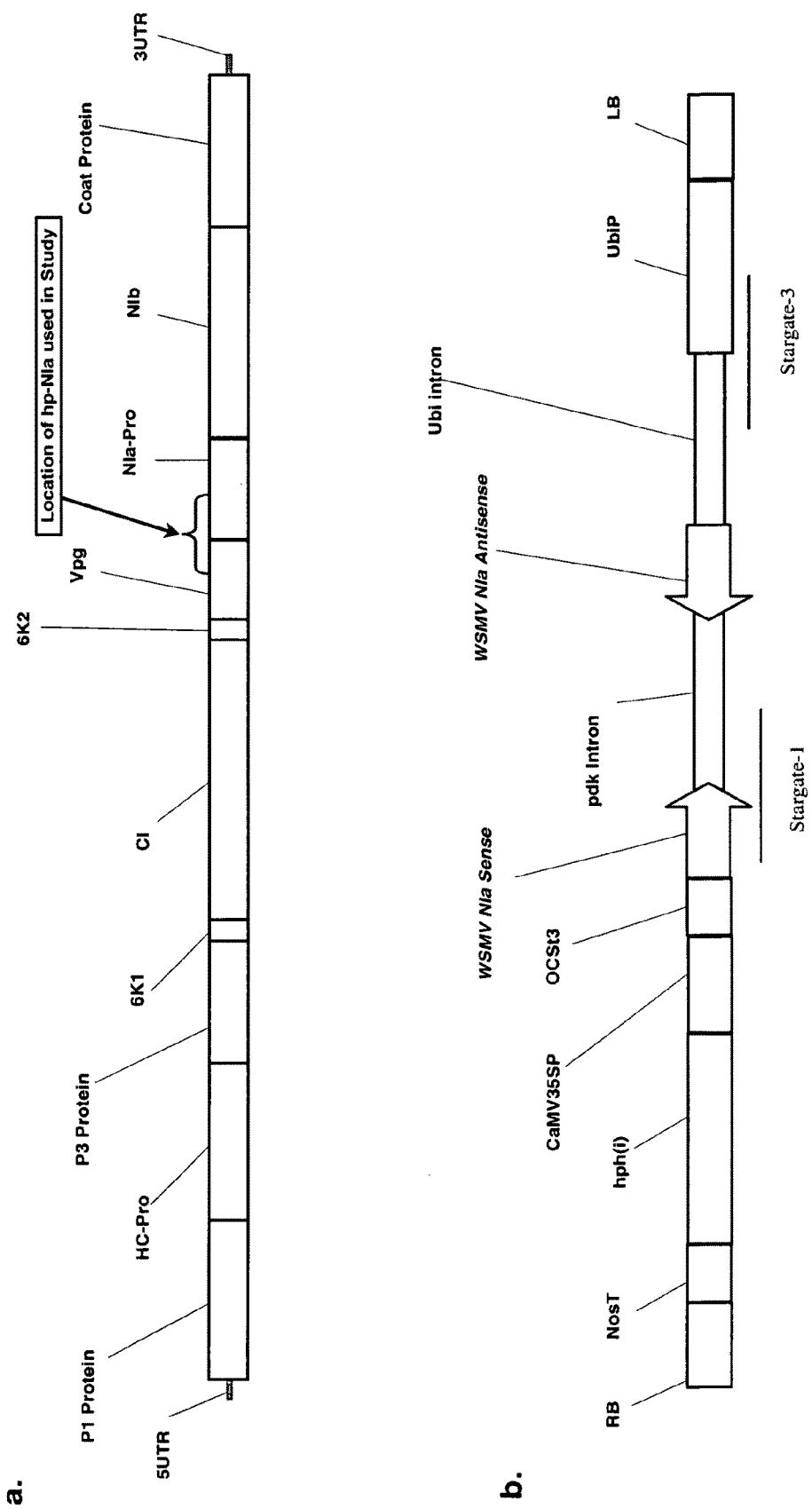
FIG. 1. Location of NIa gene on WSMV genome and construction of pStargate-NIa plasmid. a. Genome map of WSMV showing the region used, spanning the junction between the Vpg and NIa coding regions, to generate pStargate-NIa, b. Design of pStargate-NIa construct used to transform wheat, and the two Stargate amplicons (1 & 3) used to characterize the putative transgenics.

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

All references cited herein either in the reference listing or in the text are incorporated by reference.

This invention is based on the finding that silencing RNAs produced from a chimeric DNA can provide immunity to Wheat Streak Mosaic Virus (WSMV) to transgenic wheat plants expressing the chimeric DNA, to an extent much greater than in previous attempts to produce wheat plants resistant to WSMV. In a first aspect the present invention provides a transgenic wheat cell or wheat plant, the wheat cell or wheat plant comprising a chimeric DNA molecule which encodes a dsRNA molecule which is capable of inhibiting wheat streak mosaic virus (WSMV) replication, wherein the wheat cell or plant is immune to WSMV.

"Wheat Streak Mosaic Virus" or "WSMV" as used herein refers to a virus in the group Potyviridae which infects wheat plants, thereby causing pathogenic symptoms on the plants, and which is at least 90% identical in sequence to SEQ ID NO: 1, when the full length nucleotide sequences are aligned, SEQ ID NO: 1 being the cDNA sequence corresponding to the genomic RNA nucleotide sequence of the type member of WSMV (Genbank Accession No. AF285169).

As used herein the term "immunity" refers to a plant or plant cell in which replication of WSMV is inhibited at least 1000-fold, preferably at least 10,000-fold, relative to WSMV replication in a corresponding wheat cell or plant lacking the chimeric DNA molecule. Immunity may be determined as a 1000-fold lower level of WSMV replication or accumulation when the transgenic plant or plant cell is inoculated with a defined level of WSMV, compared to a corresponding wheat plant or cell lacking the chimeric DNA molecule; or as the same or lower level of virus replication or accumulation when the transgenic plant or plant cell is inoculated with 1000-fold higher level of WSMV as compared to the corresponding wheat plant or cell lacking the chimeric DNA. As used herein, a "corresponding wheat plant (or cell) lacking the chimeric DNA" or "isogenic wheat plant (or cell) lacking the chimeric DNA" refers to a wheat plant or cell which is essentially the same as the transgenic wheat plant or cell except for the presence of the chimeric DNA, and typically would be of the same cultivar or wheat variety as the parental wheat plant or cell from which the transgenic wheat plant or cell was derived.

It is preferred that in an immune wheat plant WSMV is essentially undetectable by reverse transcription-polymerase chain reaction (RT-PCR), enzyme linked immunosorbent assay (ELISA) or virus bioassay or a combination of two or more of these methods. Immunity may be determined by any of these three methods, by RT-PCR and ELISA assays, by RT-PCR and virus bioassays, by ELISA and virus bioassays, or by all three methods. These assays are preferably carried out by the methods described in the Examples herein. "Virus bioassays" refers to an assay where an extract prepared from the inoculated wheat plant or cell is used to inoculate a second, susceptible wheat plant, followed by methods to detect the presence or absence of viral replication, symptoms or pathogenesis in the second wheat plant after a suitable time period of culturing. Such virus bioassays and methods are well known in the art.

As used herein, "capable of inhibiting WSMV replication" refers to the ability of the dsRNA molecule, or a silencing RNA produced by processing from the dsRNA, to reduce the replication or accumulation of WSMV in the cell or plant. "Inhibiting", "reducing" and the like terms are relative terms, referring to the comparison with the same parameter in the corresponding wheat plant or cell which lacks the chimeric DNA. It would be appreciated that the capability of the dsRNA molecule or silencing molecule is a property of the molecule that does not require the presence of WSMV—typically, transgenic wheat plants comprising the chimeric DNA are produced before infection with WSMV may occur and in order to prevent infection.

Immunity to WSMV may be provided to wheat cells or plants by the use of silencing RNAs. As used herein, "silencing RNAs" are RNA molecules that have 21 to 24 contiguous nucleotides that are identical to or complementary to a region of the genomic RNA of WSMV. The cDNA sequence corresponding to the genomic RNA of the WSMV type member is provided as SEQ ID NO: 1. The silencing RNAs may be either "sense" (identical) or "antisense" (complementary) to the WSMV genomic RNA. It is readily appreciated that the antisense silencing RNAs are capable of hybridizing directly to the genomic RNA ((+) RNA strand) of WSMV by basepairing, and so of inhibiting the genomic RNA either prior to or during replication, whereas the sense silencing RNAs are capable of hybridizing to the (−) replicative strand of WSMV which is produced during replication of WSMV, and thereby are capable of inhibiting replication of WSMV during viral replication. The sequence of the 21 to 24 nucleotides is preferably fully identical to, and more preferably fully complementary to, a sequence of 21 to 24 contiguous nucleotides of the genomic RNA of WSMV, ie. the sequence of the 21 to 24 nucleotides of the silencing RNA is identical to the 21 to 24 nucleotides of the region of the genomic RNA of WSMV, or to its complement, particularly if the silencing RNA is an siRNA. However, miRNA sequences which have up to three, or even up to five mismatches compared to the region of the genomic RNA of WSMV may also be used (Palatnik et al, 2003). Basepairing of the siRNA or the miRNA to the WSMV genomic RNA or the (−) replicative strand may involve one or two or three G-U basepairs. When not all of the 21 to 24 nucleotides of the silencing RNA are able to basepair with the WSMV genomic RNA or its complement, it is preferred that there are only one or two mismatches between the 21 to 24 nucleotides of the silencing RNA and the region of the genomic RNA. With respect to the miRNAs, it is preferred that any mismatches, up to the maximum of five, are found in the 3' half of the miRNA, more preferably towards the 3' end of the miRNA. In a preferred embodiment, there are not more than one or two mismatches between the sequences of the silencing RNA and its target, the region of the WSMV genomic RNA or of the (−) replicative strand of WSMV. Mismatches as defined herein are nucleotide pairs other than an A-U, G-C or G-U pairs. It is also preferred that there are no non-basepaired nucleotides in the siRNA or miRNA when it hybridizes to the target RNA.

Silencing RNAs derive from longer RNA molecules that are encoded by the chimeric DNAs of the invention. The longer RNA molecules, also referred to herein as "dsRNAs" or "precursor RNAs", are the initial products produced by transcription from the chimeric DNAs in the wheat cells or plants and have partially or wholly double-stranded character formed by intra-molecular basepairing between complementary regions. The precursor RNAs include hairpin RNAs and pri-miRNAs and are non-naturally occurring. The precursor RNAs are processed by a specialized class of RNAses, commonly called "Dicer(s)", into the silencing RNAs, typically having a length of 21 to 24 nucleotides. Silencing RNAs as used herein include short interfering RNAs (siRNAs) and microRNAs (miRNAs), which differ in their biosynthesis. SiRNAs derive from fully or partially double-stranded RNAs having at least 21 contiguous basepairs, including possible G-U basepairs, without mismatches or non-basepaired nucleotides bulging out from the double-stranded region. These double-stranded RNAs are formed from either a single, self-complementary transcript which forms by folding back on itself and forming a stem-loop structure, referred to herein as a "hairpin RNA", or from two separate RNAs which are at least partly complementary and that hybridize to form a double-stranded RNA region. The stem-loop of a hairpin RNA may be part of a larger RNA molecule or structure. For example, chimeric DNAs typically include regulatory sequences such as promoters and transcription terminators which, when transcribed, give rise to 5' and 3' RNA sequences in the larger RNA molecule. MiRNAs are produced by processing of longer, single-stranded transcripts that include complementary regions that are not fully complementary and so form an imperfectly basepaired structure, so having mismatched or non-basepaired nucleotides within the partly double-stranded structure. The basepaired structure may also include G-U basepairs. Processing of the precursor RNAs to form miRNAs leads to the preferential accumulation of one distinct, small RNA having a specific sequence, the miRNA. It is derived from one strand of the precursor RNA, typically the "antisense" strand of the precursor RNA, whereas processing of the long complementary precursor RNA to form siRNAs produces a population of siRNAs which are not uniform in sequence but correspond to many portions and from both strands of the precursor. It is understood that the siRNA or miRNA molecule may occur in nature but that the chimeric DNA and the longer RNA molecules encoded by the chimeric DNAs are non-naturally occurring.

MiRNAs were first discovered as a small regulatory RNA controlling the lin-4 gene in C. elegans (Lee et al., 1993). Since then, large numbers of other naturally occurring miRNAs have been reported to be involved in regulation of gene function in animals and plants. MiRNA precursor RNAs (pri-miRNAs) of the invention, also termed herein as "artificial miRNA precursors", are typically derived from naturally occurring miRNA precursors by altering the nucleotide sequence of the miRNA portion of the naturally-occurring precursor so that it is complementary, preferably fully complementary, to the 21 to 24 nucleotide region of the WSMV genomic RNA, and altering the nucleotide sequence of the complementary region of the miRNA precursor that basepairs to the miRNA sequence to maintain basepairing. The remainder of the miRNA precursor RNA may be unaltered and so have the same sequence as the naturally occurring miRNA precursor, or it may also be altered in sequence by nucleotide substitutions, nucleotide insertions, or preferably nucleotide deletions, or any combination thereof. The remainder of the miRNA precursor RNA is thought to be involved in recognition of the structure by the Dicer enzyme called Dicer-like 1 (DCL1), and therefore it is preferred that few if any changes are made to the remainder of the structure. For example, basepaired nucleotides may be substituted for other basepaired nucleotides without major change to the overall structure. The naturally occurring miRNA precursor from which the artificial miRNA precursor of the invention is derived may be from wheat, another plant such as another cereal plant, or from non-plant sources. Examples of such precursor RNAs are the rice mi395 precursor, the *Arabidopsis* mi159b precursor, or the mi172 precursor.

Processing of the precursor RNAs to form siRNAs or miRNAs occurs by distinct Dicer enzymes. Wheat has at least five different Dicer enzymes, called DICER-LIKE (DCL) enzymes. DCL1 and DCL4 produce siRNAs of mostly 21 nucleotides length, DCL2 produces siRNAs of mostly 22 nucleotides length, and DCL3 produces siRNAs of mostly 24 nucleotides length. MiRNA precursor RNAs are processed mostly and perhaps entirely by DCL1. The primary transcripts giving rise to miRNAs are mostly generated by RNA polymerase II (Pol II) and often have a length up to several kilobases. The partly double-stranded structures with imperfect basepairing within the primary transcripts usually have a length of 80 to 250 nucleotides in plants, or approximately 70-80 nucleotides in animals. The miRNA can be produced from either the 5' or the 3' arm of the partly double-stranded structure. In plants, miRNA precursors are typically processed in a several steps. The precursors are first processed in the nucleus by DCL1, releasing the miRNA duplexed with its complementary sequence. The miRNA duplexes are then often modified by methylation of the 3'-terminal ribose by the HEN1 methylase (Yu et al 2005) which stabilizes the RNAs. The miRNA part of the duplex is transported to the cytoplasm where it associates with Argonaute protein and possibly other proteins to form RNA-induced silencing complexes (RISC), the mediators of gene silencing. Plant miRNAs often start with a U and have a C at position 19, which is the last pairing nucleotide in a 21 nucleotide miRNA duplexed with its complementary sequence.

Artificial miRNAs have been demonstrated in plants, for example Alvarez et al (2006), Parizotto et al (2004), Schwab et al (2006) each herein incorporated by reference.

In certain embodiments of the present invention, the chimeric DNA encodes a dsRNA molecule which is a hairpin RNA molecule or two complementary RNA strands which are capable of annealing to form the dsRNA molecule. The double-stranded portion of the dsRNA molecule should comprise at least 19 contiguous basepairs, preferably at least 21 or at least 27 contiguous basepairs, more preferably at least 30 contiguous basepairs or at least 50 contiguous basepairs, or at least 100 contiguous basepairs, or at least 150 contiguous basepairs. The maximum length of the double-stranded region is considered to be the full length of the WSMV genome. In preferred embodiments, the length of the double stranded region of the dsRNA is 30-1000 basepairs, or 50-1000 basepairs. One strand of the double-stranded RNA region should be at least 90% identical, preferably at least 95% identical, and more preferably at least 98% identical or 100% identical to the corresponding region of WSMV. It is appreciated that the longer the double stranded region, the lower the degree of identity may be, provided that the siRNA that is produced by processing of the dsRNA is able to inhibit replication of WSMV and provide immunity to the wheat plant or cell.

The dsRNA molecule is preferably an RNA which is capable of being processed in the wheat cell or plant to form an RNA molecule of 21 to 24 nucleotides long which is capable of said inhibition of WSMV replication.

In another embodiment the dsRNA is a pri-miRNA.

In another embodiment, the dsRNA molecule comprises more than one nucleotide sequence, or at least three different nucleotide sequences, or at least four different nucleotide sequences, or at least five different nucleotide sequences, each of a length of at least 19 contiguous nucleotides or at least 21 contiguous nucleotides, preferably each of 21-24 contiguous nucleotides in length, wherein each different nucleotide sequence is identical to a different protein coding region or untranslated region on WSMV or its complement, or where one or more such different sequences are identical to regions of the genomic strand of WSMV and one or more such different sequences are identical to the (−) replicative strand of WSMV. That is, the dsRNA molecule targets multiple regions of the WSMV genome and/or the (−) replicative strand. The different nucleotide sequences may each be a miRNA, or part of one strand of a hairpin RNA, or a combination of these, wherein the dsRNA molecule is processed to give multiple, independent and different miRNAs and/or siRNAs. Such a dsRNA also comprises complementary sequences to each of the different nucleotide sequences. Such a molecule is exemplified in Example 6. DsRNA molecules of this embodiment have advantages in producing even greater extent of resistance, and more durable and stable immunity, to wheat plants or cells. As is readily understood, the invention includes chimeric DNA molecules encoding these multi-targeting dsRNAs, wheat plants and cells, or grain, comprising the dsRNAs or chimeric DNAs, and the processes of making and using such plants or grain as disclosed more generally herein.

It is preferred that the chimeric DNA molecule comprises a Pol II or Pol III promoter which is operably linked to a DNA region encoding the dsRNA.

In certain embodiments the wheat cell or plant is a hexaploid wheat cell or plant, such as *Triticum aestivum* ssp *aestivum*, or a tetraploid wheat cell or plant such as *Triticum durum*, or triticale.

The wheat cell or plant is preferably homozygous for the chimeric DNA molecule. As used herein, "homozygous" has its common meaning in plant genetics. The wheat plant or cell preferably has a single transgenic locus comprising the chimeric DNA such as, for example, a single T-DNA insertion comprising a single chimeric DNA. It is also preferred that the wheat plant or cell does not comprise other transgenic sequences such as vector backbone sequences or parts of the vector outside of the T-DNA. Such single transgenic locus plants are preferred for regulatory purposes.

It is also preferred that the wheat cell or plant does not comprise a transgene encoding an antibiotic-resistance marker. As used herein, an "antibiotic resistance marker" refers to a transgene which encodes a product, preferably a polypeptide, which confers on the cell comprising the transgene resistance or tolerance to the effects of an antibiotic. Numerous antibiotic resistance markers are well known in the art. Examples of antibiotic resistance markers are the NptII gene encoding resistance to kanamycin, or the hyg gene encoding resistance to hygromycin, commonly used in plant transformation.

The wheat cell or plant may also comprises a transgene, such as a transgene encoding a herbicide tolerance marker or resistance or immunity to a second virus. An example of a herbicide tolerance marker is a polypeptide that confers resistance or tolerance to the herbicide glyphosate. Examples of a second virus are Barley Yellow Dwarf Virus (BYDV) or Cereal Yellow Dwarf Virus (CYDV).

It is preferred that the wheat plant is characterized by stable immunity to WSMV. As used herein, "stable immunity" refers to the stable inheritance of the immune phenotype from one generation of the transgenic plants to the next, without substantial loss of the immune phenotype. In a preferred embodiment, the extent of inhibition of WSMV in the progeny plants is at least 90% as great as in the parental generation. In a more preferred embodiment, the extent of inhibition of WSMV in the progeny plants is essentially the same as in the parental generation. Typically, stability is tested over at least three generations of the plants where the first generation of plants is at least a T2 generation of plants. The "T2 generation of plants" as used herein refers to plants which are two generations removed from the first regenerated transgenic plant (T0 generation). Seed obtained from a T0 plant is defined herein as T1 seed which, when sown, gives rise to T1 plants. Seed obtained from T1 plants is defined herein as T2 seed, which gives rise to T2 plants, etc. Stability of the immune phenotype is preferably determined on the T2, T3, T4 or later generations. Typically, the testing is done on a plurality of plants and preferably on plants which are homozygous for the chimeric DNA and therefore not segregating for the transgene(s). The immune phenotype in progeny plants may be determined by any of the means available in the art, preferably by RT-PCR detection assays for WSMV, ELISA assays for WSMV, bioassays for WSMV, or a combination of any of these.

In certain embodiments, the wheat plant is at least a third generation transgenic plant (T2 generation) or later progeny from the initially regenerated wheat plant.

In a second aspect the present invention provides a chimeric DNA, the chimeric DNA comprising (i) a wheat expressible promoter; (ii) a region which encodes a dsRNA which is capable of inhibiting WSMV replication, or which is processed in a wheat cell or wheat plant to form a silencing RNA which is capable of inhibiting WSMV replication; and (iii) a optionally a transcription termination signal. The region of the chimeric DNA DNA encoding the dsRNA typically comprises an inverted repeat of a sequence corresponding to the targeted region of WSMV. One of the two repeated sequences is in the "sense orientation" with respect to the promoter, while the other is in the "antisense orientation" with respect to the promoter. The order of the two repeated sequences with respect to the promoter may be sense followed by antisense (tail-to-tail orientation) or, antisense followed by sense (head-to-head orientation). The two repeated sequences may be identical or essentially identical to each other in the case of chimeric DNAs encoding a hairpin RNA, or either identical or non-identical in the case of chimeric DNAs encoding pir-miRNAs. The termination signal may or may not provide for polyadenylation of the dsRNA. For example, if the wheat expressible promoter is of the Pol III type, the transcription terminator is a sequence of at least four or five consecutive T nucleotides.

The present invention also provides an isolated or recombinant dsRNA molecule which is capable of being processed into a silencing RNA molecule as defined herein, characterized in that is capable of inhibiting wheat streak mosaic virus (WSMV) replication and of conferring immunity to a wheat cell or plant to WSMV. As used herein, the term "recombinant" refers to the dsRNA as it exists in a plant following production by transcription of a chimeric DNA in the plant. The recombinant dsRNA is non-naturally occurring, in that it comprises RNA sequences which have been joined together in combination(s) that do not occur in nature and/or it has been produced by transcription from one or more chimeric DNAs of the invention. Typically, the "sense" and "antisense" portions of the dsRNA do not occur in nature as a covalently-joined molecule. In a preferred embodiment of the dsRNA such as the hairpin RNA or the pri-miRNA, the sense and antisense sequences are joined by a loop or stem-loop structure in the initially transcribed RNA produced from the chimeric DNA. It is appreciated that the dsRNA is processed in the wheat plant or cell such as by a Dicer enzyme, to produce a dsRNA product which has the loop, or part of the stem-loop removed, so that the dsRNA product has two separate strands which are not covalently joined. Therefore, the dsRNA may be detected as an unprocessed dsRNA molecule, or by the presence of its processed products.

The dsRNA molecule may be a hairpin RNA molecule or a pri-miRNA, or comprise two complementary RNA strands which are annealed to form the dsRNA molecule. In the case of the two complementary strands, the dsRNA molecule may be encoded by one chimeric DNA or by two separate chimeric DNA molecules.

In a third aspect the present invention provides a process for producing a transgenic wheat cell or plant of the first aspect of the present invention, comprising
  i) introducing into a parental wheat cell a chimeric DNA molecule comprising (i) a wheat expressible promoter; (ii) a region which encodes a dsRNA which is capable of inhibiting WSMV replication or which is processed in a wheat cell or wheat plant into a silencing RNA molecule which is capable of inhibiting WSMV replication; and (iii) optionally, a transcription termination signal; and optionally
  ii) regenerating a wheat plant from the wheat cell comprising the chimeric DNA molecule; and
  iii) identifying and/or selecting a cell obtained in step (a) or a plant obtained in step (b) or a progeny plant thereof which is immune to WSMV.

In a preferred embodiment, the process further comprises producing progeny plants from the wheat plant selected or identified in (iii). The identifying and/or selecting step is typically on the basis of assays performed after inoculating the wheat plant or cell with WSMV, as described herein. The wheat plant may be selected as one in which WSMV replication is inhibited by at least 1000-fold, preferably at least 10,000-fold, or at least 100,000-fold. The identifying and/or selecting step may be carried out on progeny plants obtained from the regenerated plant, such as, for example, T2 plants or subsequent generations of progeny.

In a preferred embodiment, the chimeric DNA molecule is introduced into a parental wheat cell by biolistics or by bacterium-mediated transformation, such as *Agrobacterium*-mediated transformation. It is preferred that the *Agrobacterium* is *Agrobacterium tumefaciens*, particularly of a strain which is disabled for the naturally occurring oncogenic genes.

In another aspect the present invention provides a transgenic wheat cell or wheat plant, comprising
  a chimeric DNA molecule which encodes a precursor RNA molecule, and
  a silencing RNA molecule, wherein the silencing RNA molecule is 21-24 nucleotides long and is identical to, or complementary to, a WSMV genomic RNA, wherein the wheat cell or plant is immune to WSMV. The silencing RNA may or may not comprise a 3' nucleotide (ie. the 3'-terminal nucleotide) which is methylated in its ribose moiety.

In a preferred embodiment, the silencing RNA molecule is fully identical to, or complementary to, 21 to 24 consecutive nucleotides of the WSMV genomic RNA.

In other embodiments, the silencing RNA molecule has no nucleotides or only one nucleotide, or not more than two nucleotides, or if it is an miRNA not more than three or not more than five nucleotides, which are not identical to a corresponding nucleotide position in the WSMV genomic RNA or its complement. That is, the silencing RNA may have one or two nucleotides which are not identical to the region of the WSMV genomic RNA, or if it is a miRNA, up to three or even up to five nucleotides which are not identical, without affecting the efficacy of the silencing effect.

As will be understood the wheat plant of the present invention may be used for commercial production of wheat products such as wheat grain, or after harvesting the grain, for processed grain which is no longer able to germinate, such a milled grain, flour, wholemeal, bran, starch or other products derived from the grain, for ingredients for making food products, for food products, or for non-food products such as ethanol. The plants may also be used as animal feed, either by direct feeding of the animals in the field, or after harvesting the wheat plants for hay or silage, or use of the grain as animal feed. The wheat grain obtained from the wheat plant of the present invention may comprise the chimeric DNA molecule.

The wheat grain may be processed so that it is not able to germinate. The wheat grain may be milled, ground, rolled, flaked, pearled, parboiled, or cracked grain.

A process is also provided for producing the wheat grain of the present invention, comprising
  i) growing a wheat plant according to the first aspect of the present invention,
  ii) harvesting the grain from the wheat plant, and optionally
  iii) processing the grain.

Also provided is a process for producing wheat flour, wholemeal, bran or starch, comprising
  i) obtaining the grain of the present invention, and
  ii) milling the grain, and optionally
  iii) refining the milled grain to produce the wheat flour, wholemeal, bran or starch.

As will be understood the wheat grain, flour, wholemeal or bran of the present invention may be used to produce a food product, or as animal feed, or to produce a non-food product such as starch or ethanol.

The present invention also provides a process for selecting a molecule which is capable of inhibiting WSMV, comprising:
  (i) introducing into a parental wheat cell a chimeric DNA molecule encoding an RNA molecule,
  (ii) optionally, regenerating a transgenic wheat plant comprising the chimeric
  DNA molecule from the parental wheat cell,
  (iii) determining whether the wheat cell of i) or plant of ii) or a progeny plant thereof is immune to WSMV,
  (iv) identifying a wheat cell or plant or a progeny plant that is immune to WSMV, thereby selecting the molecule,
wherein the RNA molecule is 21-24 nucleotides long and is identical to, or complementary to, a WSMV genomic RNA.

In this process step (iii) may comprise RT-PCR to detect WSMV RNA in the cell or plant or progeny plant, immunoassay such as ELISA to detect WSMV protein in the cell or plant or progeny plant, or virus bioassay to detect WSMV in the cell or plant or progeny plant.

Polynucleotides and Genes

The present invention refers to various polynucleotides. As used herein, a "polynucleotide" or "nucleic acid" or "nucleic acid molecule" means a polymer of nucleotides, which may be DNA or RNA, and includes mRNA, cRNA, cDNA, tRNA, siRNA, shRNA, hpRNA and miRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid".

By "isolated polynucleotide" we mean a polynucleotide which has generally been separated from the polynucleotide sequences with which it is associated or linked in its native state. Preferably, the isolated polynucleotide is at least 90% free from other components with which it is naturally associated.

The present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A genomic form or clone of a gene containing the transcribed region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome.

As used herein, a "chimeric gene" refers to any gene that is not a native gene in its native location. Typically, a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations.

Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Furthermore, the term "exogenous" in the context of a polynucleotide (nucleic acid) refers to the polynucleotide when present in a cell in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide of the invention includes polynucleotides which have not been separated from other components of the transgenic (recombinant) cell in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide.

The % identity of a polynucleotide is determined by GAP (Needleman and Wunsch, 1970) analysis (GCG program) with a gap creation penalty=5, and a gap extension penalty=0.3. Preferably, the GAP analysis aligns two sequences over their entire length. Alternatively, the query sequence is at least 450 nucleotides in length, and the GAP analysis aligns the two sequences over a region of at least 450 nucleotides.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further embodiment, the present invention relates to polynucleotides which are substantially identical to those specifically described herein. As used herein, with reference to a polynucleotide the term "substantially identical" means the substitution of. one or a few (for example 2, 3, or 4) nucleotides whilst maintaining at least one activity of the polynucleotide. In addition, this term includes the addition or deletion of nucleotides which results in the increase or decrease in size of the polynucleotide whilst maintaining at least one activity of the polynucleotide.

The present invention refers to use of oligonucleotides. As used herein, "oligonucleotides" are polynucleotides up to 50 nucleotides in length. The minimum size of such oligonucleotides is the size required for the formation of a stable hybrid between an oligonucleotide and a complementary sequence on a nucleic acid molecule of the present invention. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length. Oligonucleotides of the present invention used as a probe are typically conjugated with a label such as a radioisotope, an enzyme, biotin, a fluorescent molecule or a chemiluminescent molecule.

Polynucleotides and oligonucleotides of the present invention include those which hybridize under stringent conditions to a sequence provided as SEQ ID NO: 1, the cDNA sequence of the WSMV type strain. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. A variant of a polynucleotide or an oligonucleotide of the invention includes molecules of varying sizes of, and/or are capable of hybridising to, the WSMV genome close to that of the reference polynucleotide or oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close to, for example to within 50 nucleotides, the region of the WSMV genome where the specific oligonucleotides defined herein hybridise. The terms "polynucleotide variant" and "variant" also include naturally occurring WSMV variants.

Nucleic Acid Constructs

The present invention includes nucleic acid constructs comprising the polynucleotides of the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a wheat plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in leaves and/or stems of the wheat plant or another cereal plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

The promoters contemplated by the present invention may be native to the wheat plant to be transformed or may be derived from an alternative source, where the region is functional in the wheat plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in monocotyledonous plants are well known in the art (see, for example, Greve, 1983; Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992, 1993), Sambrook et al. (1989, supra) and U.S. Pat. No. 5,164,316.

Alternatively or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

In an embodiment, the promoter is at least capable of expressing the polypeptide in leaves of the plant, particularly adult leaves. Examples of leaf-specific promoters which can be used include those described in Yamamoto et al. (1994 and 1997), Kwon et al. (1994), Gotor et al. (1993), Orozco et al. (1993), Matsuoka et al. (1993) and Stockhaus et al. (1987 and 1989).

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of *Agrobacterium tumefaciens* (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

Vectors

The present invention includes use of vectors for manipulation or transfer of genetic constructs. By "chimeric vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a wheat cell or tissue or a progenitor cell or tissue thereof, or capable of integration into the genome of the wheat plant or cell such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a wheat cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of the wheat plant or cell. Accordingly, the nucleic acid comprises appropriate elements which allow the molecule to be incorporated into the genome, or the construct is placed in an appropriate vector which can be incorporated into a chromosome of the wheat plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of wheat cells or for the establishment of transgenic wheat plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The level of a dsRNA, or the silencing RNA produced by processing of the dsRNA, may be modulated by increasing or decreasing the level of expression of the chimeric gene that codes for the dsRNA in the wheat cell. The level of expression of a gene may be modulated by altering the copy number per cell. A plurality of transformants may be selected and screened for those with a favourable level and/or specificity of transgene expression arising from influences of endogenous sequences in the vicinity of the transgene integration site. A favourable level and pattern of transgene expression is one which results in an immune phenotype to WSMV.

Recombinant Cells

Another embodiment of the present invention includes a recombinant wheat cell comprising a host cell transformed with one or more recombinant molecules of the present invention, or progeny cells thereof. Transformation of a nucleic acid molecule into a wheat cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a wheat plant. Transformed nucleic acid molecules of the present invention can remain extrachromosomal or can integrate into one or more sites within a chromosome of the transformed (i.e., recombinant) cell in such a manner that their ability to be expressed is retained. Preferred host cells are wheat cells.

Transgenic Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "compared to an isogenic plant" refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a wheat cell, tissue or plant that has not been modified according to the invention. Wild-type wheat cells, tissue or plants may be used as controls to compare levels of expression of an exogenous nucleic acid or the extent and nature of trait modification with cells, tissue or plants modified as described herein.

Transgenic wheat plants, as defined in the context of the present invention include progeny of the plants which have been genetically modified using recombinant techniques, wherein the progeny comprise the transgene of interest. Such progeny may be obtained by self-fertilisation of the primary transgenic wheat plant or by crossing such plants with another plant of the same species. Transgenic plant parts include all parts and cells of said plants comprising the transgene such as, for example, cultured tissues, callus and protoplasts.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. A preferred species of hexaploid wheat is *T. aestivum* ssp *aestivum* (also termed "breadwheat"). Tetraploid wheat includes *T. durum* (also referred to herein as durum wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to Triticale.

Several general methods for delivery of a gene into wheat cells may be used. Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy, Madison Wis. (1987).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transformation of cereal plants such as wheat for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. Nos. 5,589,617, 6,541,257, and other methods are set out in WO 99/14314. Preferably, transgenic wheat plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

EXAMPLES

Example 1

Generation of Hairpin RNAi Construct Targeting WSMV

Wheat streak mosaic virus sequences were retrieved using VirusFASTAs® Rothamsted Research Institution Version 2005.05.20. Sequences of NIa region from five full genome sequences (Type strain with Genbank Accession No. AF285169, Turkey Isolate Accession No. AF454455, Czech Isolate Accession No. AF454454, El Batan strain Accession No. AF285170 and Sydney Isolate Accession No. AF057533) were retrieved and aligned using AlignX (Vector NTI Advance® 10.3.0). This identified a highly conserved portion of the NIa gene of WSMV (FIG. 1a) which was amplified by PCR and cloned into the vector pStargate, to generate the pStargate-NIa (FIG. 1b) that would transcribe into a hairpin RNA. Primers were designed against the NIa gene (FIG. 1a) based on the most conserved regions identified from the alignment. Leaf samples were collected from WSMV-infected wheat plants and preserved at −80° C. until RNA was extracted from them. RNA was extracted from leaf tissues with a Qiagen miniprep kit, following the manufacturer's instructions. One step reverse transcription (RT) reactions were performed using a Qiagen onestep RT PCRKIT. Primers NIaF1(5554) 5'-CTGGACCGATCGGATTAAGA-3' (forward) and NIaR2(6249) 5'-GGCAAGGTTAATGCTACCA-GATCC-3' (reverse) were used for NIa amplification using 50° C. for 30 min, 95° C. for 15 min, followed by (94° C. for 30 s, 60° C. for 45 s, 72° C. for 60 s) for 40 cycles with a final extension at 72° C. for 10 min. The amplified fragment was cloned into pGEM-T-Easy vector (Promega), sequenced and aligned with reported WSMV sequences to confirm the identity of the amplified sequence.

To generate the RNAi constructs, a 615 bp Topo fragment, covering 370 bp of the genome linked protein (Vpg) and 245 bp of Nuclear Inclusion Protein (NIa) genes including the cleavage site between the two genes, was generated using primers, NIaF1-Topo1, 5'-CACCTCCTCACAATACTG-GCACTTCTA-3' and NIaR2(6249) 5'-GGCAAGGTTAAT GCTACCAGATCC-3' using PCR amplification from the NIa clone. The resulting PCR fragment was cloned into pENTR/D-TOPO® Entry vector (Invitrogen), which was subsequently transferred into pStargate destination vector by a single LR Clonase reaction (Invitrogen). In these reactions, the PCR-derived fragments are inserted into two regions flanked by two recombination sites (attB1 and attB2) in opposite directions, and the spliceable intron is flanked by the two inverted repeats. The resulting plasmid was called pStargate-NIa which is shown schematically in FIG. 1b. The construct therefore comprised a sense copy and an antisense copy of the Vpg-NIa sequence, separated by spliceable pyruvate dehydrogenase kinase (pdk) intron under the control of the maize polyubiquitin promoter.

pStargate, a binary vector, is a modified pHellsgate (Wesley et al., 2001) suitable for use in *Agrobacterium* mediated transformation in monocot plants and uses the same Gateway™ recombination system. It contains a maize ubiquitin promoter and its intron for the hairpin construct, along with a 35S: hph for plant selection using hygromycin, and spectinomycin resistance gene for bacterial selection.

For confirmation of insertion in the binary vector, pStargate, with and without RNAi fragment VPg-NIa, was digested with NotI at 37° C. for three hours and compared with simulated restriction analysis carried out with Vector NTI Advanced (10.03.0). The constructs were also validated by sequencing.

Selected colonies of *E. coli* containing pStargate-NIa were grown in 400 mL of LB media with spectinomycin (100 μg.μL-1) and the plasmid DNA was extracted using Nucleobond Machery Nagel® (Duren Germany) Maxi kit following manufacturer's instructions, for use in wheat transformation with biolistics.

Example 2

Transformation of Wheat Embryos and Regeneration of Transgenic Plants

Despite the fact that the transformation vector was a binary plasmid, biolistics rather than *Agrobacterium*-mediated transformation was employed to generate transgenic wheat plants containing the RNAi construct. Although a hygromycin selectable marker was present on pStargate-NIa, transformation selection was based on co-bombardment with pNeo (Pharmacia) containing a nptII marker and transformants were selected with 50 mg.l-1 geneticin.

The scutella of 450 freshly isolated embryos from Bob-White 26 spring wheat, at about 14 days post-anthesis were co-transformed by biolistics bombardment with DNA of pStargate-NIa and pNeo (Pharmacia) carrying nptII as plant selectable marker. Three fold greater weight of pNeo was used to give approximately equal moles of the two plasmids. The biolistics and tissue culture protocols were largely as described by Pellegrineschi et al., 2002. The only modification was the use of Phytagel instead of Bacto-Agar. At the end of the tissue culture phase, T0 plants, being the first generation of transgenic plants, were transferred to a glasshouse and seed collected individually from each spike separately as a precaution against transplanted plants containing unseparated shoots from different events.

A total of 16 independent T0 transgenic wheat plants were generated with a transformation efficiency of 3.5% per bombarded embryo. All the primary transgenic lines presumed to have the hairpin transgene, were designated as hpws. Where multiple T0 plants were recovered from a single bombarded embryo, they were distinguished with letters, e.g. hpws2a and hpws2b. All T1 progeny had no obvious visible difference in morphological phenotype from the parental cultivar, Bob White selection 26 (BW26).

Example 3

Methods for Analysis of Transgenic Plants

DNA extraction was carried out from leaf samples using "DNAeasy Plant Mini Kit" following manufacturer's instructions (Qiagen Inc., Valencia, Calif. USA) and PCR was carried out for selectable marker nptII using PCR. A 700-bp nptII fragment was amplified using the forward primer Neo3 5'-tacggtatcgccgctcccgat-3' and reverse primer Neo5 5'-ggc-tattcggctatgactg-3', both sequences being in the nptII coding region using the following thermal cycle conditions: 94° C. for 30 s, 55° C. for 30 s, 72° C. for 60 s for 40 cycles with a final extension at 72° C. for 10 min.

Analysis of T0 Transgenic Plants—Southern Hybridization Method

Wheat genomic DNA was extracted from transgenic wheat by standard methods. Approximately 15 μg of DNA was digested overnight with BamHI and separated by 0.8% agarose gel electrophoresis (Sambrook, 2001) and the DNA transferred onto a nylon membrane (Pall Biodyne® B), followed by standard hybridization procedures (Sambrook 2001). The Stargate3 amplicon was labeled as probe using [α-32 P] dCTP (NEN) using the multiprime system (Amersham, IL USA), X-Ray film was exposed to the blots at –80° C.

Analysis of T1 Transgenic Plants—Genomic PCR Method

T1 seeds of each transgenic event were kept on moist filter paper in petri plates for 3-4 days and the germinated seeds were transferred to pots. Approximately a three centimeter-long young leaf was collected from each plant and freeze dried. Genomic DNA was extracted in DNA extraction buffer containing 0.1M Tris-HCL, pH 8.0, 0.05M EDTA pH 8.0, 1.25% SDS. Primers were designed against the two extremes of the hairpin construct. Primers Stargate 1F 5'-atatcatgcgat-cataggcgtctcg-3' and Stargate 1R 5'-atgatgataactgcagcg-caagctt-3' covering regions from the pdk intron through the NIa sense fragment to the ocsT 3' terminator and amplifying a 920 bp PCR product. Primers Stargate-3F 5'-cccaaagagaaa-cactggca-3' and Stargate-3R 5'-taaacgccgtcgacgagtctaa-3', covering the Ubi Intron and Ubi Promotor, were used to amplify a PCR product of 603 bp.

The PCR reaction was performed in a Thermalcycler PC-960C (Corbett Research) with the following protocol: 95° C. for 15 min; (94° C. for 1 min; 63° C. (stargate1)/65° C. (stargate3) for 45 seconds; 72° C. for 1 min)×35 cycles and final extension of 10 minutes at 72° C. Two amplicons were used in the study to assay for both ends of the hpRNA transgene including a large portion of the promoter (FIG. 1b).

Analysis of T1 Transgenic Plants—Virus Bioassay Method

Virus inoculum was prepared by grinding WSMV infected tissue in a mortar and pestle at a 1:10 w/v ratio in 0.02 M Potassium phosphate buffer (pH 7). The homogenate was filtered through four layers of Miracloth® (Calbiochem, USA), abrasive Celite (Johns-Manville, USA) was added at 2% w/v to the final volume of inoculum, and the mixture was left on ice for one hour. Putative transgenic BW26 plants were doubly inoculated at the 2-3 leaf stage, with the prepared sap extracts from WSMV-infected leaf material. The sap plus celite abrasive was first applied with an air-powered spray gun and then leaves were gently rubbed with gloved fingers to ensure the infection of plant by the virus. The plants were scored for symptoms at 14 dpi on a scale of 0-4 with 0 as healthy, 1 as mild with very few streaks, 2 as moderate with streaks that coalesce, 3 as severe with approximately 50 percent leaf area with streaks, 4 as the most severe or lethal symptoms where the streaks develop into chlorosis of more than 70 percent of leaf area. Samples were collected for WSMV-specific ELISA using Agdia reagents (Elkhart, Ind.) following manufacturer's instructions. Plates were read at A405 nm in ELISA Reader Spectra Max 340 PC (Molecular Devices, CA USA) 60 minutes after addition of substrates. Healthy controls were included on every plate, every sample was duplicated, and means were used in calculating the ELISA value ratio between inoculated and healthy controls. Data was also recorded on the fertility and height of plants.

Detection of WSMV Particles and RNA from Inoculated Transgenic Lines

Total RNA was extracted from WSMV inoculated transgenic plants using a Qiagen RNAeasy mini kit following the manufacturer's instructions. 500 ng total RNA was serially diluted in 1:10 steps to 5 pg (final dilution 10-5). In order to amplify viral RNA but avoid amplifying transcripts from the transgene, primers were designed to hybridize to sequences just outside the cloned NIa sequence used in the transgene. The primers used were NIa-1F 5'-CTGGACCGATCGGAT-TAAGA-3' and NIa-3R 5'-CTGAGAACTTCCATG-GCACA-3' and the PCR reactions amplified a 1045 bp viral product. Reverse transcription (RT) reaction was carried out at 50° C. for 30 min, following by 95° C. for 15 min; (94° C. for 1 min; 60° C. for 45 seconds; 72° C. for 1 min)×35 cycles and final extension of 10 minutes at 72° C.

Test-inoculation to Detect Infectious Virus in Leaf Sap

Sap was extracted from inoculated transgenic plants at 28 dpi using 0.02 M potassium phosphate buffer; the initial concentration was 1:10 (w leaf/v buffer). This was further diluted to 1:250 and 1:500 concentrations. Each dilution was mixed with celite abrasive and then inoculated onto three plants each. This method was used to evaluate the effectiveness of the hpRNA construct in eliminating viral replication and preventing the formation of infectious particles. Symptoms were scored and leaf samples collected 14 dpi for ELISA as described previously.

Segregation Analysis of NIa Transgene and Resistance in Selected T1 Families

Twenty five to 35 seeds from four selected transgenic lines were germinated in pots. Leaf samples were collected and DNA was extracted as described above. Genomic PCR was carried out as described in Example 3 to detect both Stargate 1 and Stargate 3 amplicons, to ensure the presence of the complete transgene promoter and hairpin construct. In order to observe if resistance co-segregated with the transgene, the plants were inoculated with WSMV as described above, ELISA was performed 14 dpi on inoculated plants, plant heights and symptoms were recorded. Segregation of selectable marker nptII was also determined using PCR as described above.

Example 4

Molecular and Serological Characterization of Transgenic Resistance to WSMV

Figure 2:
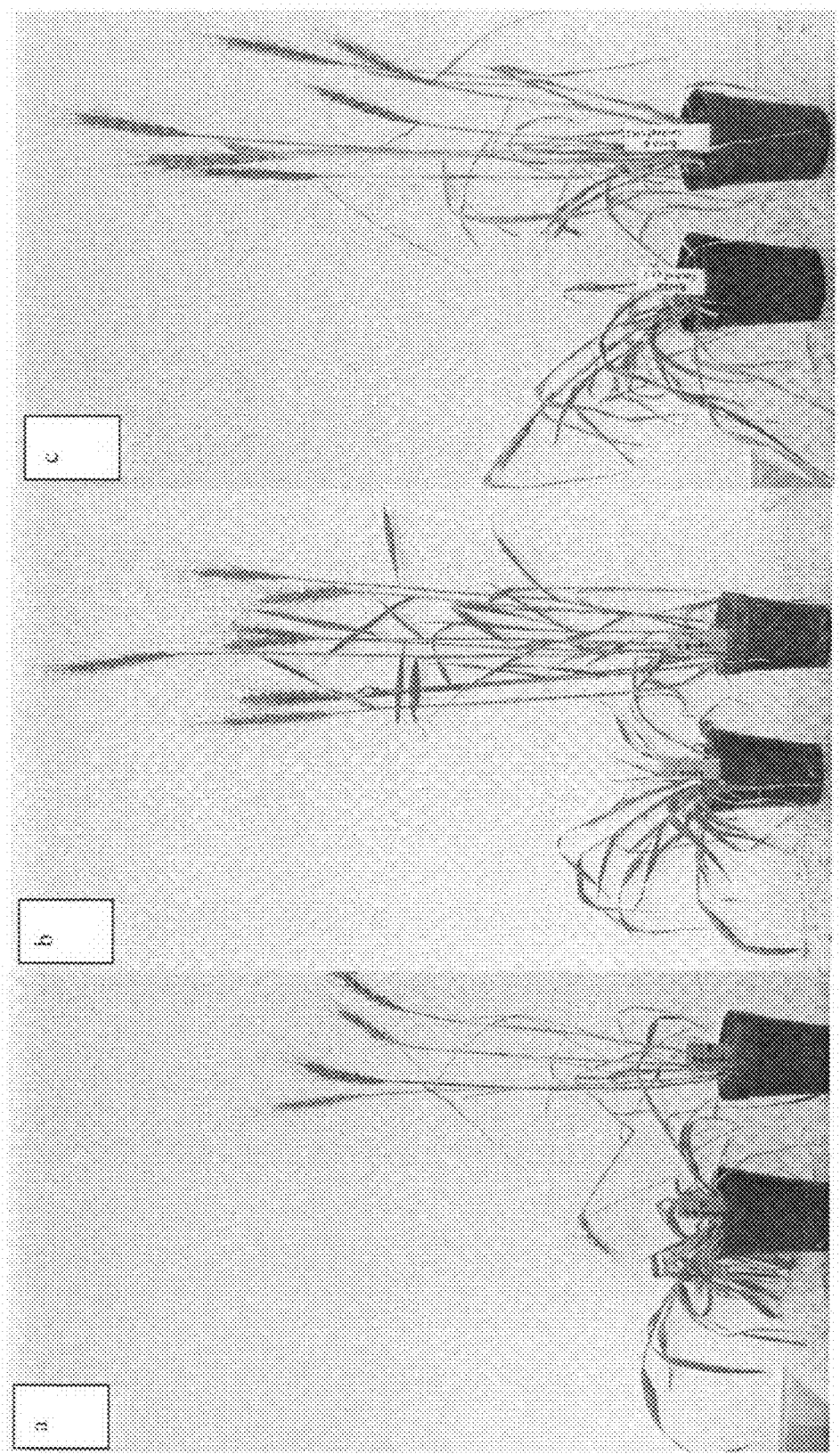
FIG. 2. Reaction of hpws transgenic wheat lines to infection by WSMV. a) family hpws24b where the presence of the transgene was responsible for an intermediate resistance or recovery phenotype evident in the inoculated right plant compared to a susceptible plant (left). b) fully resistant inoculated transgenic segregant (right) and susceptible non-transgenic segregant (left) of family hpws2b. c) Bobwhite26 controls, infected (left) and uninoculated (right).

An initial assessment of 6-8 T1 individuals of all sixteen transgenic families indicated the presence of the selectable marker nptII via genomic PCR, verifying that these plants were transgenic. Further analysis involved inoculating each individual plant with WSMV and assaying with DAS-ELISA at 14 days post inoculation (dpi). WSMV typically causes light-green to faint yellow blotches and streaks in wheat leaves parallel to the veins. As the disease progresses affected plants appear retarded and show a general yellow mottling. Diseased plants are usually yellowed and moderately to severely stunted (FIG. 2) with prostrated tillers often with empty spikes or spikes with shriveled kernels.

Figure 3:
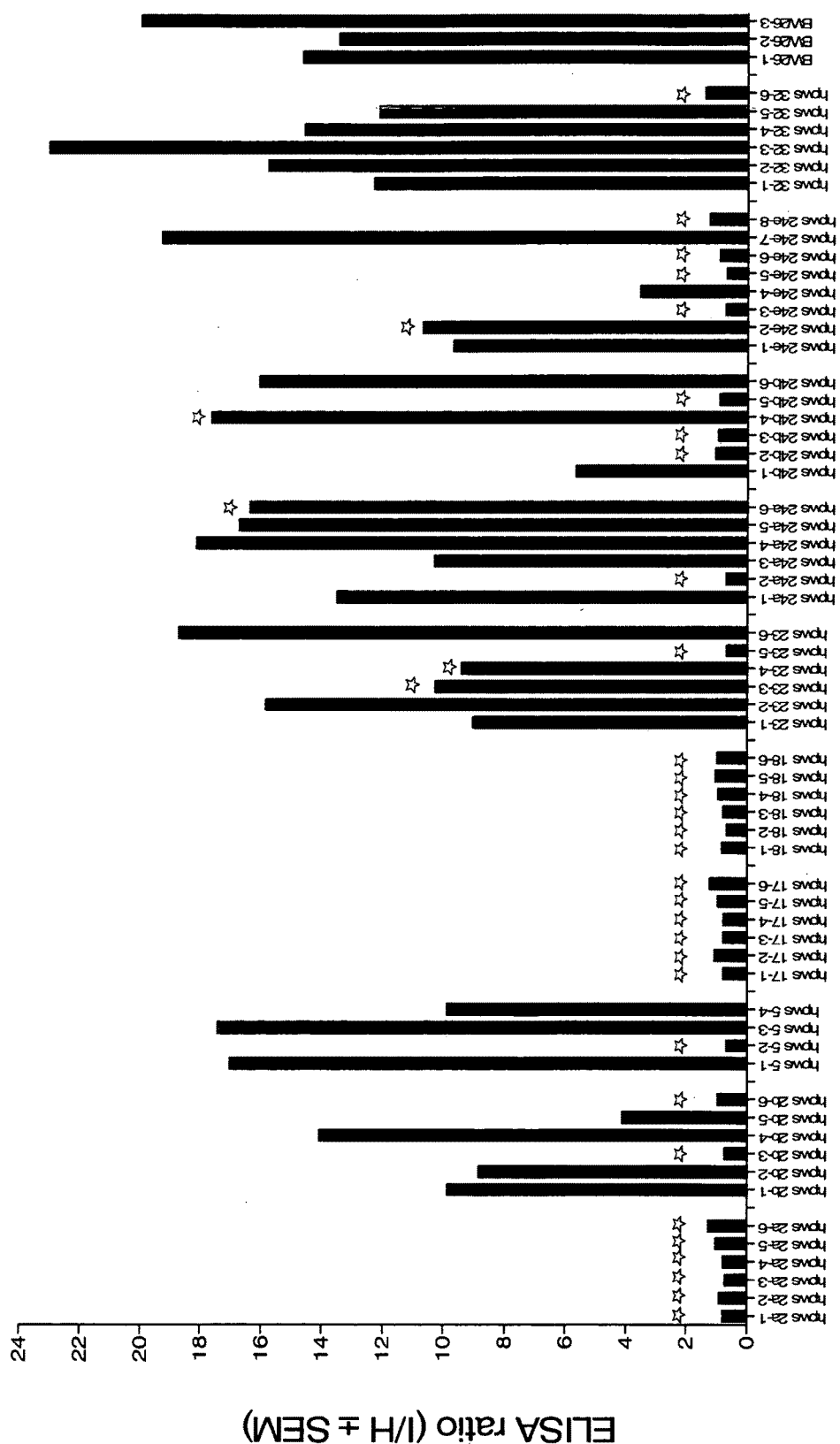
FIG. 3. Families of ten T1 segregating transgenic families showing at least one resistant individual. Virus levels detected by ELISA 14 day post inoculation. The ELISA ratio plotted is the ELISA reading of the inoculated plant divided by the average ELISA reading of all healthy controls. The star ( ) represents the presence of both Stargate1 and Stargate3 amplicons in a transgenic plant, whereas the absence of the star indicates that at least one of the amplicons is missing.

Virus accumulation in leaves was determined using ELISA and expressed as a ratio of the average ELISA value for samples from the inoculated plants relative to the ELISA value for samples from the non-inoculated controls. This was done since the ELISA value for non-inoculated controls gave a low, background reading above zero using the Agdia kit. Ten families had at least one highly-resistant individual (ELISA ratio approximately 1) while all Bobwhite 26 (BW26) non-transformed control plants were highly susceptible (ELISA ratio>9) (FIG. 3). All T1 individuals of three families hpws2a, 17 and 18 were completely immune to WSMV when challenged, suggesting they possessed genetically unlinked, multiple insertions of Stargate-NIa. Seven families were segregating for both resistant and susceptible T1 individuals. The immune individuals in all families were indistinguishable, in plant morphology and phenotype and in ELISA values, from the healthy uninoculated controls. Both Stargate 1 and 3 amplicons could be amplified from the 10 transgenic lines, suggesting that they contained the complete Stargate-NIa transgene. All tested T1 progeny of the remaining six families were highly susceptible to WSMV and lacked one or both Stargate amplicons; these families had the selectable nptII gene but lacked the full Stargate-NIa transgene and therefore were not analysed further. It was presumed that in these lines, only a non-functional part of the RNAi construct was inserted.

The RNAi Construct Confers Immunity Against WSMV in Wheat

The complete absence of symptoms in inoculated transgenic individuals from some transgenic events over a number of experiments led us to hypothesize that they were immune. Experiments were conducted to see if infectious virus or viral RNA could be recovered from the resistant inoculated transgenic plants. Leaf sap from plants in four transgenic inoculated families was extracted and inoculated onto test plants of control BW26 at various dilutions to investigate the presence of any infectious WSMV particles.

Figure 4:
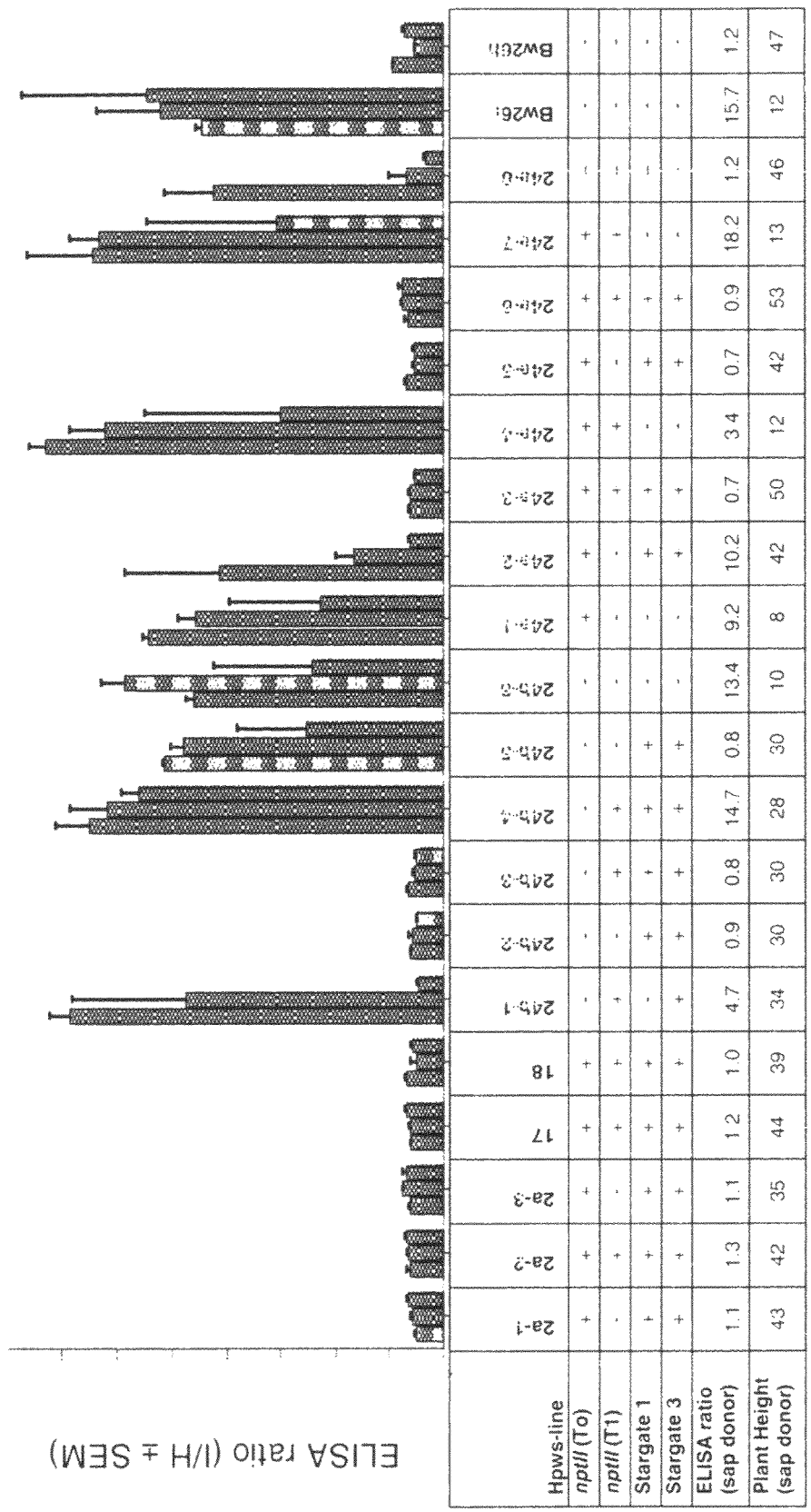
FIG. 4. Virus transmission from inoculated transgenic plants onto Bobwhite26. Sap was extracted from inoculated transgenic plants at three dilutions, 1/10, 1/250 and 1/500 from left to right in each cluster of three bars. Each dilution was inoculated onto three non-transgenic Bobwhite26. At 14 dpi samples were collected and processed for WSMV ELISA. Plotted is the average ELISA ratio (inoculated divided by healthy) for the three test-inoculated plants for each sap dilution. Also tabulated are the molecular analysis of the T0 parent (nptII), the molecular analysis of the inoculated T1 individual serving as sap donor (nptII, Stargate1 and Stargate3 PCR), and the ELISA ratio and plant height (cm) at booting stage of the inoculated sap donor T1 individual.

Results from these dilution experiments revealed that all plants from the T1 families of hpws2a, hpws17 and hpws18 were apparently immune to WSMV as no virus was recovered and carried over to control wheat through mechanical inoculation, even at the highest sap concentration. Sap from segregants with transgenes failed to transmit infection as judged by symptoms and ELISA, whereas sap from segregants with no transgene and non-transformed controls (BW26) did transmit infection in every case and at all dilutions (FIG. 4). Transgenics lines hpws24b and hpws24e, which may be clones of the same transgenic event, showed some deviation from the pattern observed for the other transgenic families. As expected, segregants amplifying neither Stargate amplicon had fully-infectious sap and some segregants amplifying both amplicons were immune. However, some segregants (e.g. hpws24e-2, FIG. 4) amplifying both amplicons were themselves intermediate in susceptibility and their sap was infectious, at least at the highest concentration. Also some segregants amplified only one of the Stargate amplicons (hpws24b-1 and hpws24e-8, FIG. 4), and were intermediate in their susceptibility and yielded infectious saps. It was concluded that these lines contained multiple, genetically unlinked insertions, some of which provided immunity and some of which provided an intermediate level of resistance.

Figure 5:
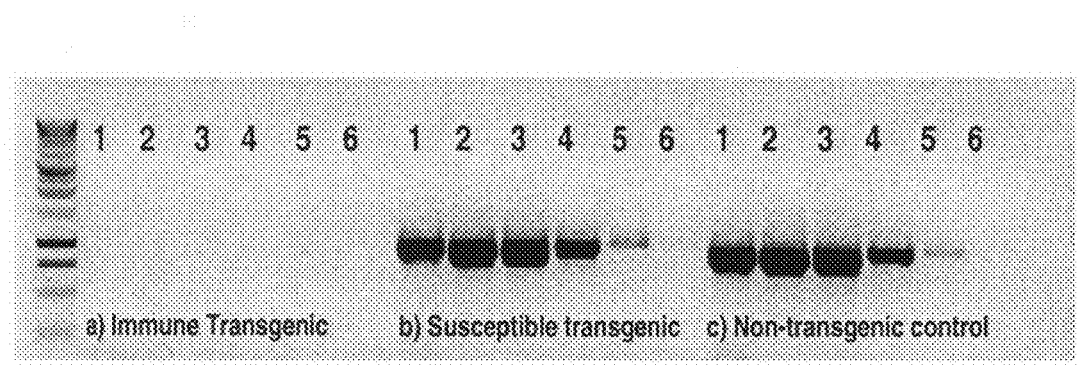
FIG. 5. Immunity in hpws transgenic wheat against WSMV as evident from RT PCR for WSMV in inoculated plants: a) immune transgenic wheat (hpws2b-5); b) susceptible transgenic wheat (hpws2b-6); and c) susceptible non transgenic BW26. Lanes 1, 2, 3, 4, 5 and 6 have decreasing amounts of leaf RNA used in the RT-PR reaction: 500, 50, 5, 0.5, 0.05 and 0.005 ng, respectively.

Furthermore, even the highly-sensitive RT-PCR was unable to detect viral RNA in resistant transgenic individuals. RT-PCR was carried out on all members of 2b, 17 and 24a transgenic events representing both susceptible and resistant transgenic plants, selection was based on ELISA reaction and the presence of both Stargate amplicons. No virus RNA was amplified from the transgenic plants that were negative for WSMV through ELISA, reflecting that RNA interference was conferring immunity. The sensitivity of the assay, and the extent of resistance, could be appreciated from the observation that WSMV sequences could not be amplified from resistant transgenic plants using as high as 500 ng of total RNA in the RT-PCR reaction; on the other hand WSMV was amplified from as little as 5 pg of total RNA from infected susceptible controls (FIG. 5). In other words, the suppression of viral RNA replication appeared to be complete and can be quantified at more than five orders of magnitude. The virus was not detectable by these methods in immune plants after inoculation.

Example 5

Segregation of pStargate-NIa and pNeo Plasmids in Transgenic Wheat

The studies above indicated that resistance was co-segregating with the transgene in all hpws transgenic families. The inheritance of transgenic resistance was more extensively examined in larger T1 populations of four transgenic lines, hpws2b, hpws17, hpws18 and hpws24b, through PCR amplification of two regions of the pStargate-NIa construct (Stargate1 and Stargate3) and also by WSMV bioassay. These four lines were representative of the different segregation patterns observed in the smaller T1 populations of the ten transgenic lines showing some resistance. In three out of four analyzed transgenic families, the resistance perfectly co-segregated with the hairpin transgene, and the immune plants remained symptom-less throughout the experiment. The plants where one or both fragments (Stargate 1 and 3) were absent, developed characteristic symptoms of WSMV and had a marked difference in height as compared to resistant transgenic plants. In hpws24b, the plants developed severe symptoms where one or both the amplicons of the transgene were missing. However, all transgenic wheat plants of hpws24b containing both amplicons developed only mild to moderate symptoms.

Figure 6:
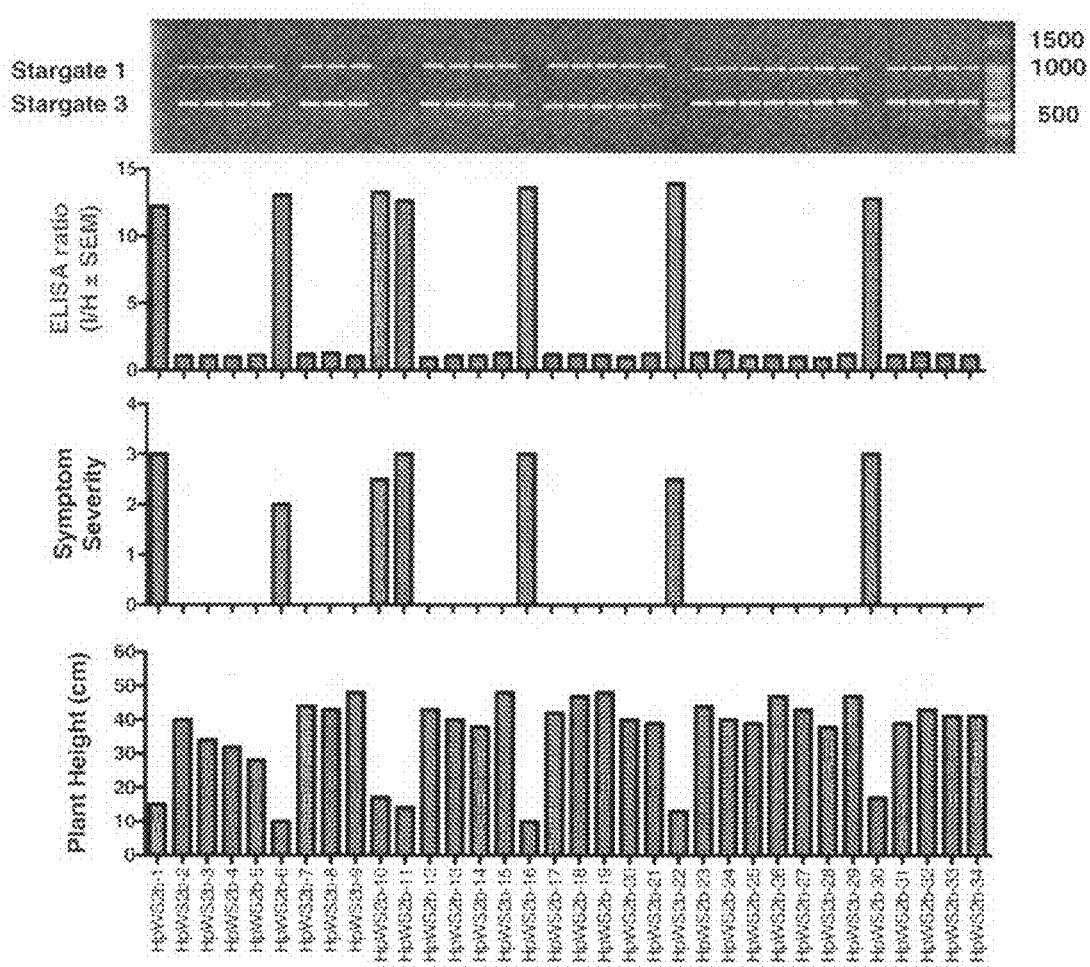
FIG. 6. WSMV inoculation of 34 T1 individuals of hpws2b transgenic family. The transgene segregated with resistance in simple Mendelian ratio. Shown are the PCR amplification of both Stargate fragments, ELISA ratio at 14 dpi, symptom severity and plant height at booting stage.

In the T1 family of hpws2b, there was perfect co-segregation of Stargate1 and Stargate3 amplicons with virus resistance (FIG. 6). The segregation of resistance and transgene amplicons conformed to a 3:1 Mendelian ratio (27 resistant:7 susceptible; P=0.779 Fisher's exact test). Interestingly, the nptII selectable marker was segregating independently of the hpws insertion. This independence was confirmed by a segregation pattern consistent with a 9:3:3:1 ratio (P=0.6, Fisher's exact test), where out of 27 resistant plants, 17 carried the marker gene while 10 did not; and where out of 7 susceptible plants, 4 plants carried the marker gene while 3 plants did not. It therefore appears that this transgenic event had a single insertion of hpws and a single insertion of nptII at a separate, genetically unlinked locus. Southern blot hybridization analysis of hpws2b using Stargate3 as probe also indicated a single copy of the transgene. T1 individuals were easily recovered which were transgenic for the RNAi construct but were missing the selectable marker gene.

Figure 7A:
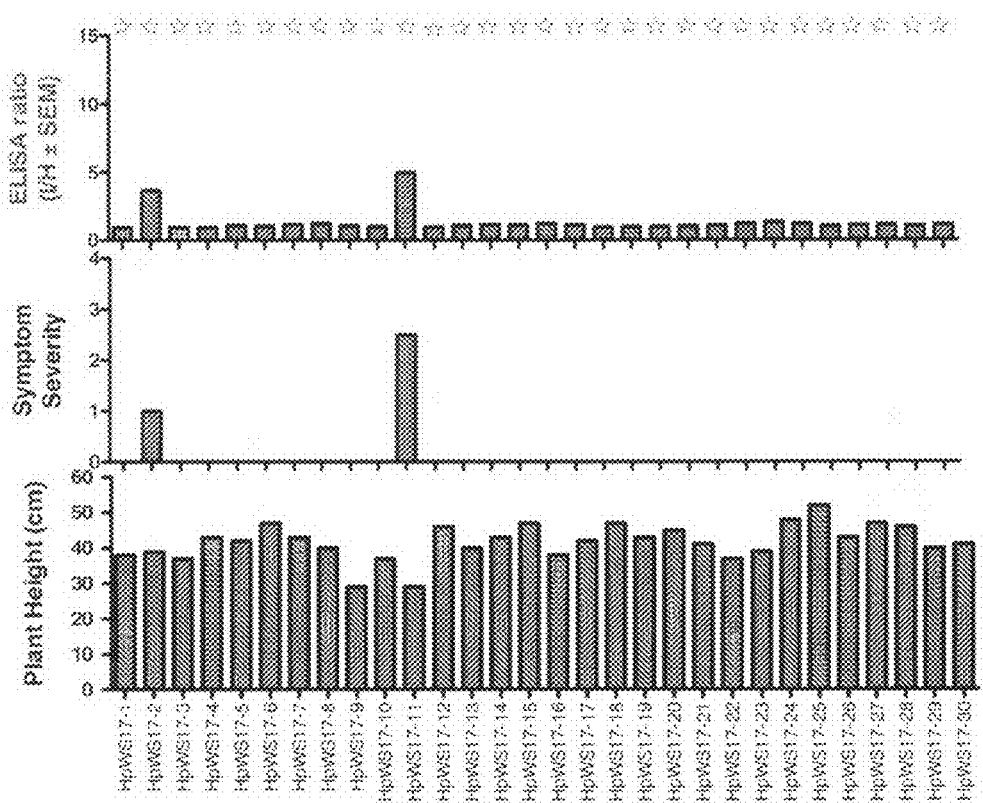
FIG. 7. WSMV inoculation of T1 transgenic families. Shown are the ELISA ratio at 14 dpi, symptom severity and plant height at booting stage. a) 30 plants of hpws17; b) 30 plants of hpws18; c) 36 plants of hpws24b. The star represents the presence of both Stargate1 and Stargate3 amplicons in a transgenic plant, whereas the absence of the star indicates that at least one of the amplicons is missing.
Figure 7B:
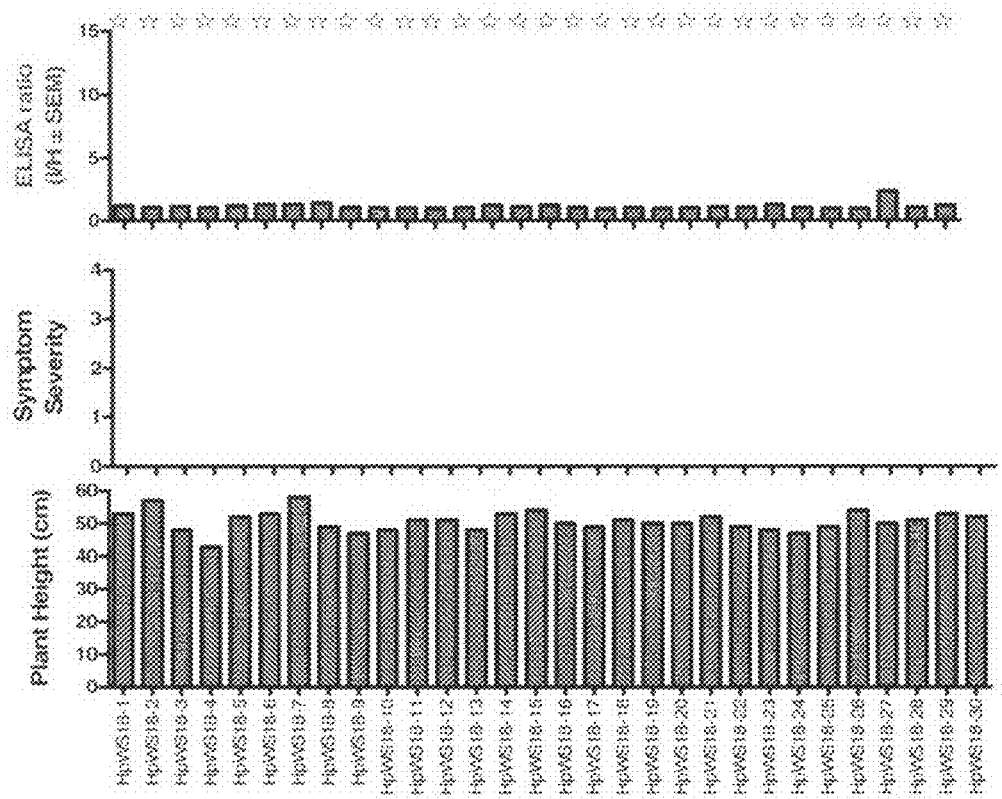
Figure 7C:
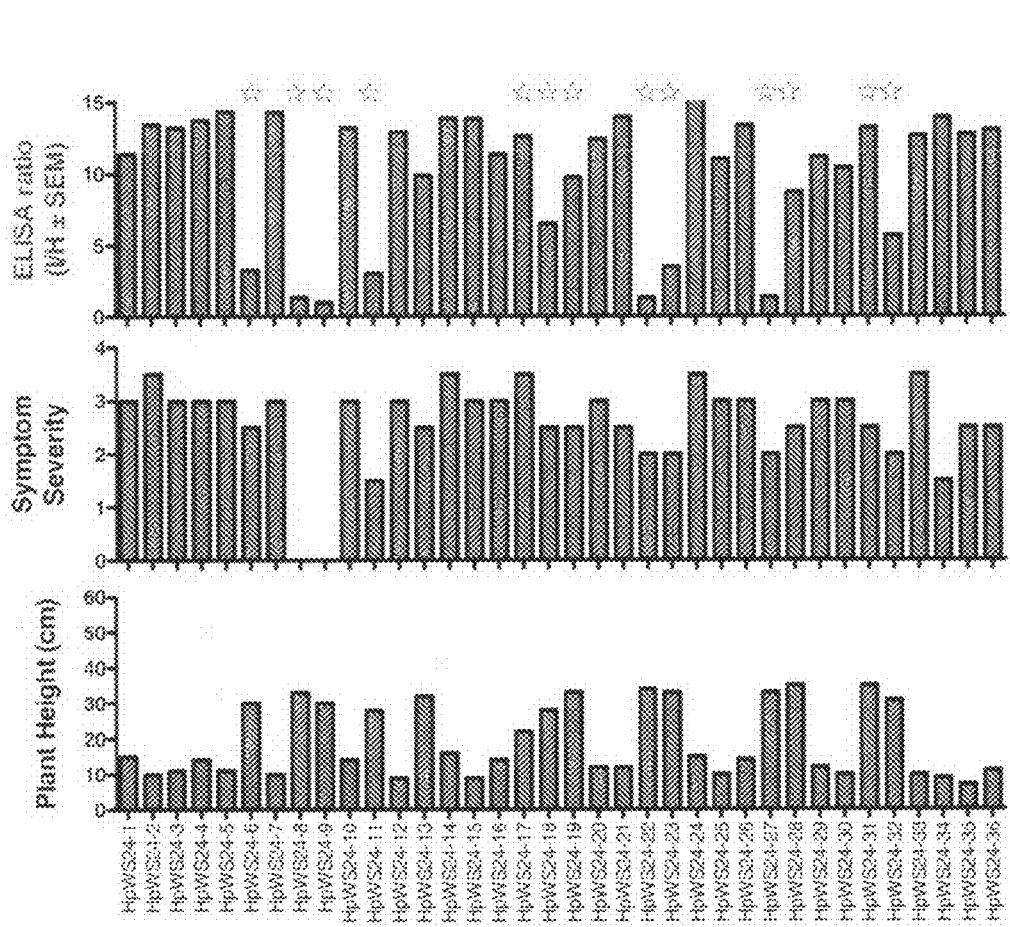
Figure 11:
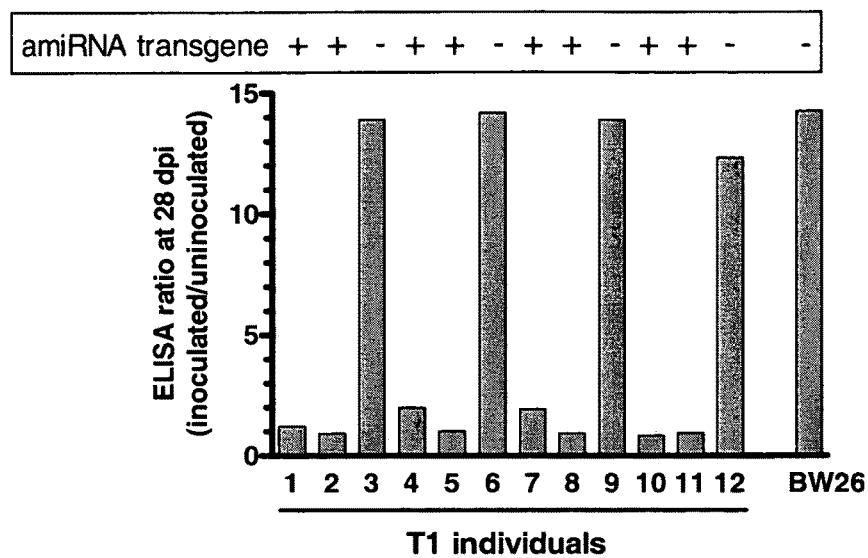
FIG. 11. ELISA data for T1 plants from one family of wheat plants transformed with the chimeric miRNA construct, after inoculation with WSMV.

In families hpws17 and hpws18, the resistance was uniform in all test plants, with the exception of two plants of family hpws17 in which a low level of virus accumulation was evident causing mild symptoms. The ELISA ratio for hpws17-2 and hpws 17-11 was 3.6 and 4.9 respectively, indicating a slight accumulation of virus (FIG. 7). However, the plants recovered by 21 dpi, so that newly emerging tissues were asymptomatic, and at booting stage the plant height was not significantly different from the immune inoculated plants or healthy controls. Both Stargate amplicons were successfully amplified in these two plants. These moderately-resistant plants had upright tillers in contrast to the prostrate tillers of inoculated susceptible controls. The selectable marker in these two families segregated independently of the hpws transgene. The segregation for resistance and the selectable marker gene in family hpws17 was 23 R, nptII+:5 R, nptII-:2 r, nptII+:0 r, nptII- (where R is resistant, r is susceptible). Southern blot hybridization analysis of DNA from the T0 hpws17 plant showed two hybridizing fragments using Stargate3 as probe. It was concluded that hpws17 had one copy of functional nptII and two copies of functional hpws transgenes. For family hpws18 the segregation of nptII was 23+:7-. There were no susceptible plants in a total of 36 hpws18 T1 individuals (FIGS. 3 and 7). It was concluded that hpws18 had one functional nptII and 3, or more, copies of functional hpws transgenes.

The plants in family hpws24b appeared to have a non-Mendelian segregation pattern, where fourteen out of 36 T1 plants amplified both Stargate amplicons. Initially only two plants, hpws24a-8 and hpws24a-9, were resistant to WSMV inoculation at 14 dpi (FIG. 7) and 21 dpi but the resistance in hpWS24a-8 started breaking down at 28 dpi. The hpws24 plants, with both amplicons, had erect stems and achieved reasonable height as compared to susceptible controls. In some plants only one Stargate amplicon was amplified and these were completely susceptible; some with Stargate 1 only, and some with Stargate 3 only. The segregation pattern for nptII was independent of the transgene. Only one plant, hpws24-9, was fully resistant by ELISA at 28 dpi, and had no nptII selectable marker. Thirteen plants displayed intermediate resistance phenotypes where the virus accumulated but the plant developed normally. Of the 23 susceptible transgenics, 17 did not have the nptII selectable marker, while 6 had an nptII insert.

Discussion

This study reports for the first time engineered RNAi mediated immunity in wheat against WSMV using a gene silencing construct.

It was notable that in a relatively small set of transgenic lines, transgenic plants were obtained with a single insertion of the transgene of interest and that were completely immune to WSMV. In selected lines, the immunity co-segregated with the transgene in a simple Mendelian fashion. It was concluded that RNA silencing, induced by the expression of intron-separated hairpin RNA (ihpRNA) from the WSMV-Vpg-NIa genes, was responsible for the observed immunity to WSMV.

Co-transformation with different transgenes carried on two separate plasmids has been shown to facilitate the segregation of transgenes of interest from selectable marker genes (Huang et al., 2004; Jayaraj et al., 2008; Komari et al., 1996; Matthews et al., 2001; Vidal et al., 2006; Zhao et al., 2007). It is evident also in this study that a number of our transgenic events had the transgene and selectable marker inserted in unlinked loci and segregating independently of each other. This was very evident in hpws2b. This technique therefore permitted the development of marker-free WSMV immune plants. Modifications of the transformation protocol, especially the molar ratio of the two plasmids may be useful in achieving desired co-transformation efficiencies and opportunity for marker-free segregants (Chen et al., 1998).

WSMV may be seed transmitted in wheat although at a low frequency (Jones et al., 2005). Infected seed may serve as initial foci for infection in the field. Acaria tosichella, the wheat curl mite, is the primary natural vector of WSMV (Slykhuis, 1955) and plays an important role in secondary spread of the virus and development of epidemics under favorable agro-climatic conditions. It was therefore of particular epidemiological importance that the hpws construct described above could achieve immunity, with no prospect of infectious particles being recovered for secondary infection. A number of lines of evidence justified classifying the level of resistance as immunity. The resistance was classified as immunity by four criteria: no visible disease symptoms were produced in inoculated plants, ELISA readings for WSMV were as in uninoculated plants, viral sequences could not be detected by RT-PCR from leaf sap, and leaf saps failed to give infections in susceptible plants when used in test-inoculation experiments. In particular, saps from inoculated immune transgenic plants failed to transmit infection to test plants and WSMV could not be detected by RT PCR analysis even from 500 ng of leaf RNA from the same leaf samples. The immunity suppressed viral RNA accumulation more than 105 fold in the immune transgenic hpws plants as compared to susceptible controls. It was considered that the transgenic plants were pre-primed by the hpws transgene so that corresponding RISC RNA-protein complexes were ready to degrade invading viral RNA and thus effective at preventing any viral replication.

Populations of transgenic lines hpws17 and hpws18, with multiple inserts, were almost completely immune, and non-segregating for the transgene. The evidence suggested in these cases that the multiple inserts continued to be functional and were not inactivated through mechanisms such as methylation. Two plants, hpws17-2 and hpws17-11, were not immune but did display a recovery type of resistance; the initial virus accumulation at 14 dpi did not arrest normal plant growth and at the booting stage the plant height was not significantly different from that of immune transgenic plants or uninoculated controls.

Transgenic line hpws24 produced a number of segregants with intermediate resistance which changed over time. Transgenic individuals were symptom free up to at least 14 dpi when non-transgenic controls had evident symptoms, but later developed symptoms and higher ELISA ratios. It would require further investigations to understand what is happening in this event. There may be interactions between multiple transgenes resulting in DNA methylation and transgene suppression. Non-Mendelian inheritance of some transgene insertions has been previously reported (reviewed by Yin et al., 2004). Various factors in the process of transgene integration may contribute to instability of expression such as insertion near repetitive DNA or in heterochromatin (reviewed by Fagard and Vaucheret, 2000; Pawlowski and Somers, 1996; Prols and Meyer, 1992; Stam et al., 1997a; 1997b; 1998).

Example 6

Construction of a Chimeric DNA to Express miRNA in Wheat Against WSMV

Five WSMV genomic sequences including that of the WSMV type strain were aligned to identify conserved nucleotide sequences that could be used in a multi-miRNA construct (FIG. 8). FIG. 8 also shows the concensus WSMV sequence obtained from the alignment. The conserved sequences chosen as candidates for targeting in WSMV were each present in the five representative WSMV strains. The WSMV strain for which sequences were aligned were:
WSMV Type Strain. Length: 9384 nucleotides; Accession No. AF285169; Version AF285169.1; GI:11066853 (Choi, et al., (2001) Arch. Virol. 146: 619-628.
WSMV El Batan Strain Length: 9339 nucleotides; Accession No. AF285170; Version AF285170.1 GI:11066855 (Choi, et al., (2001)
WSMV Czech Strain Length 9381 nucleotides; Accession No. AF454454; Version AF454454.1 GI:17981491 (Rabenstein, et al., (2002) J. Gen. Virol. 83: 895-906)
WSMV Sidney 81 Length 9384 nucleotides; Accession No. AF057533; Version AF057533.1 GI:3047320 (Stenger, et al., (1998) Phytopathology 88: 782-787)
WSMV Turkey 1 Length 9384 nucleotides; Accession No. AF454455; Version AF454455.1 GI:17981493; (Rabenstein, et al., (2002) J. Gen. Virol. 83: 895-906)

Figure 9:
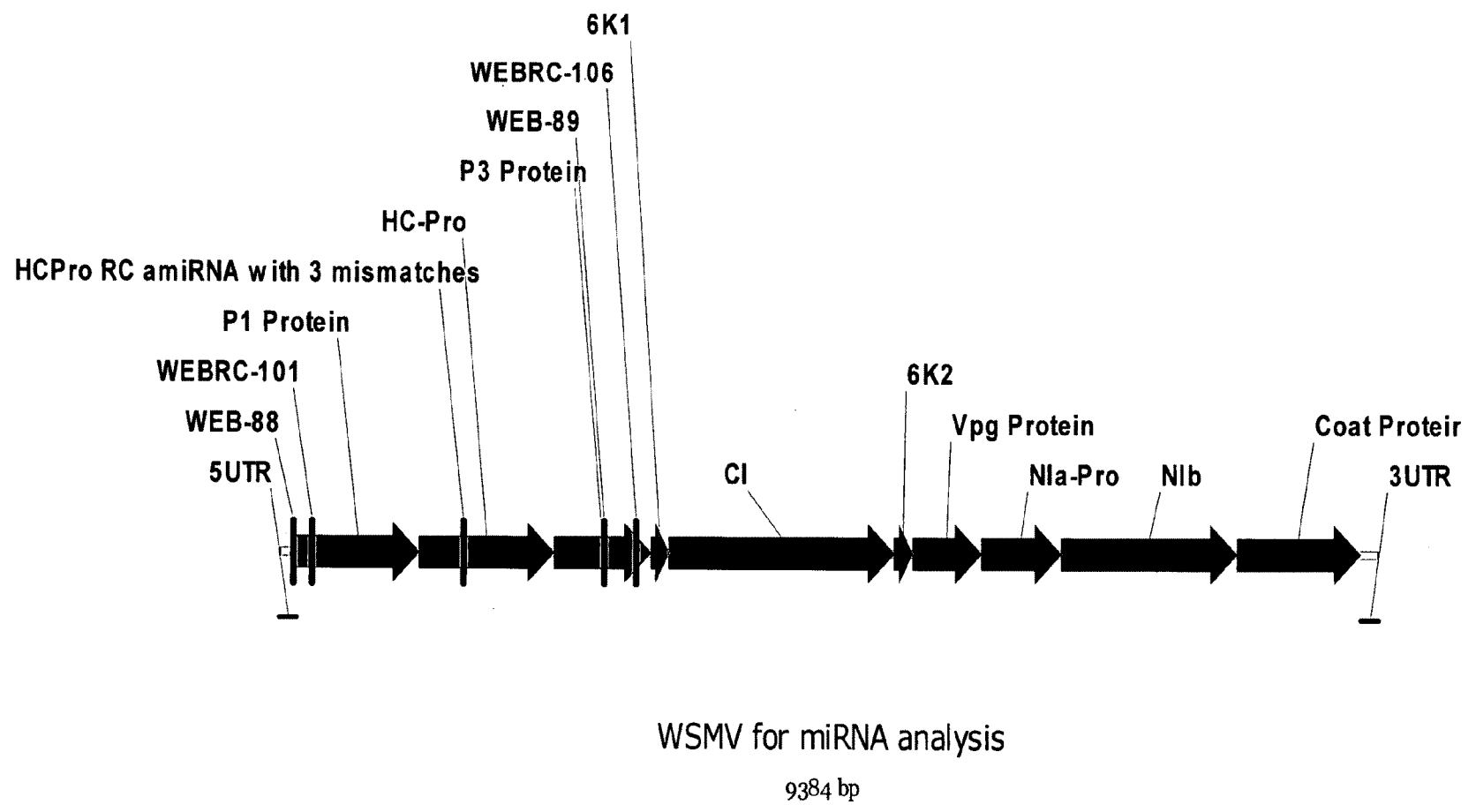

The candidate target sequences were then examined for 21-nucleotide sequences which resembled miRNAs and having a minimum free energy ($\Delta G$) of binding to their complementary sequences (and therefore WSMV) of less than −30 kcal/mol. Five sequences were chosen; the sequences are shown in Table 2 along with the corresponding positions in the WSMV concensus sequence. Three of the sequences were complementary to the WSMV genomic RNA and therefore targeted the genomic strand, while the other two (WEB88 and WEB89) were complementary to the (−) replicative strand of WSMV, ie. identical to regions of the WSMV genomic RNA and therefore targeted the (−) replicative strand of WSMV. Moreover, the five miRNAs targeted different protein-encoding regions of the genomic RNA or its complement (Table 2). These target regions are shown schematically in FIG. 9.

A vector encoding a truncated mi395 from rice was then modified to substitute the naturally occurring rice miRNA sequences with the five chosen miRNA sequences. The mi395 precursor from rice naturally encodes 7 miRNAs, designated mi395a to mi395g. However, the vector used contained a truncated mi395 gene and encoded only the first five of these. The native and modified mi395 gene sequences are shown in FIG. 10.

The chimeric gene was inserted into vector and used to transform wheat cells of the variety Bob White, and transgenic wheat plants were regenerated.

TABLE 1

Conserved candidate sequences for targeting with miRNA, and the complementary sequences thereto (SEQ ID NOs: 2-20, respectively, from top to bottom)

| | Location on genome |
|---|---|
| >1-200<br>GTTCATTGTGAGCTCTCGCATAGAGATAAGCAATGGC | 1-200 |
| >1-200+<br>CAGCGAATTGTTTGCTCGGTGA | 1-200+ |
| >201-400<br>GGACCAGGAAGCATTTTCTGGTCAAA | 201-400 |
| >2601+<br>TCGAGCAAGATCTTTCACACGCAGAGTGTGC | 2601+ |
| >2801<br>TACGACTCACATATTCTGGTCC | 2801 |
| >2801a<br>TACAAAGGGAGTTCCTTGAGGAT | 2801a |
| >2801+<br>TGGAGGAAGGTTACTCACCTTTGCGGAAACGC | 2801+ |
| >3001<br>TTTTACAACATGGCCGCGAACGTCTTGCAAGTTATACT<br>CATAGGCCTTTCTACCGTTTTCGGAGC | 3001 |
| >3001a<br>TATTTATTAAAGAAGATCTTAAAAATGCT | 3001a |
| >9000<br>GATGATGTGAGGGAGAACACGCACAGTTTCAATGGTGT | 9000 |
| Complementary sequences to target sequences: candidate sequences for miRNA: | |
| >1-200, 37 bases<br>GCCATTGCTTATCTCTATGCGAGAGCTCACAATGAAC | 1-200 |
| >1-200+, 22 bases<br>TCACCGAGCAAACAATTCGCTG | 1-200+ |
| >201-400, 26 bases<br>TTTGACCAGAAAATGCTTCCTGGTCC | 201-400 |
| >2601+, 31 bases<br>GCACACTCTGCGTGTGAAAGATCTTGCTCGA | 2601+ |
| >2801, 22 bases<br>GGACCAGAATATGTGAGTCGTA | 2801 |
| >2801a, 23 bases<br>ATCCTCAAGGAACTCCCTTTGTA | 2801a |
| >2801+, 32 bases<br>GCGTTTCCGCAAAGGTGAGTAACCTTCCTCCA | 2801+ |
| >3001, 65 bases<br>GCTCCGAAAACGGTAGAAAGGCCTATGAGTATAACTTG<br>CAAGACGTTCGCGGCCATGTTGTAAAA | 3001 |
| >3001a, 29 bases<br>AGCATTTTTAAGATCTTCTTTAATAAATA | 3001a |
| >9000, 38 bases<br>ACACCATTGAAACTGTGCGTGTTCTCCCTCACATCATC | 9000 |

TABLE 2 amiRNAs, their target WSMV Genes and reference point on WSMV consensus sequences (SEQ ID NOs: 21-25, respectively, from top to bottom)

| Name of amiRNA | Mature amiRNA | Target Gene | Coordinates on consensus sequences |
|---|---|---|---|
| >WSMV-miR395a/WEB88 | AGCUCUCGCAUAGAGAUAAGC (SEQ ID NO: 21) | P1 | 109-129 |
| >WSMV-miR395b/WEB89 | UCGAGCAAGAUCUUUCACACG (SEQ ID NO: 22) | P3 | 2765-2785 |
| >WSMV-miR395c/WEBRC-101 | UGACCAGAAAAUGCUUCCUGG (SEQ ID NO: 23) | P1 | 272-292 |
| >WSMV-miR395d/WEBRC-106 | UAACUUGCAAGACGUUCGCGG (SEQ ID NO: 24) | P3 | 3038-3058 |
| >WSMV-miR395e/HCPro-RC | UCGGCACAUAAUGGAAUCUUC (SEQ ID NO: 25) | HC-pro | 1976-1987 |

Example 7

Results of Transgenic Resistance with Multiplex amiRNA

BobWhite#26 wheat was transformed using biolistics with the selectable marker (nptII) and the amiRNA gene on separate DNA molecules. 25 transgenic plants were recovered with the selectable marker gene. Nine of these had not incorporated a copy of the amiRNA gene.

T1 progeny were mechanically inoculated with WSMV. Symptoms were monitored for six weeks and virus accumulation measured using ELISA at 2 weeks and 4 weeks post inoculation. In all 14 families where the amiRNA transgene was present and segregating, the symptoms and ELISA readings showed a dramatic reduction in symptoms and virus titre in the individuals inheriting the amiRNA transgene. Many of the transgenic individuals showed no symptoms at all and no detectable virus in new leaves. A large number of non-transgenic controls, both BobWhite#26 and non-transgenic segregants from all families, were uniformly infected with symptoms and high virus titres, demonstrating the uniformity of the inoculation process.

The resistance in some families was characterised as immunity as confirmed by test inoculations using extracts from the inoculated transgenic leaves onto susceptible, untransformed plants. No infections were transmitted from the immune plants to the susceptible plants.

The plants are self-fertilised, and homozygous progeny plants are identified in the T2 generation. Such plants are expected to show stable and durable immunity to WSMV. These plants can be tested in field experiments.

Targeting of multiple conserved sequences as shown in these Examples was considered to increase the likelihood of durable and stable immunity against WSMV. Not only were the plants immune to the challenge WSMV strain, they are also expected to be immune to the other strains of WSMV which comprise the conserved target sequences. Moreover, the use of a multi-gene targeting chimeric DNA, in this case encoding five separate and distinct miRNAs, reduced the likelihood of WSMV variants arising which could overcome the silencing. In contrast, immunity provided by a single-targeting silencing RNA might be expected to be more likely to be overcome by mutations in the virus. Furthermore, targeting both the genomic and (−) replicative strands of WSMV further increased the likelihood of effective immunity against the virus by targeting different stages of the viral lifecycle with the one transgene. Such a design of the chimeric DNA has advantages not only for effective and stable immunity, but also simplifies breeding of the transgenic plants.

REFERENCES

Alvarez et al (2006) Plant Cell 18:1134-1151
Baley G J, Talbert L E, Martin J M, Young M J, Habernicht D K, Kushnak G D, Berg J E, Lanning S P and Bruckner P L (2001) Crop Science 41:1779-1784.
Bevan et al. (1983) Nucl. Acid Res. 11: 369-385.
Chen W P, Gu X, Liang G H, Muthukrishnan S, Chen P D, Liu D J and Gill B S (1998) Theoretical and Applied Genetics 97:1296-1306.
Choi I R, Hall J S, Henry M, Zhang L, Hein G L, French R and Stenger D C (2001) Arch Virol 146:619-628.
Conner R L, Thomas J B and Whelan E D P (1991) Crop Science 31:315-318.
Divis L A, Graybosch R A, Peterson C J, Baenziger P S, Hein G L, Beecher B B and Martin T J (2006) Euphytica 152: 41-49.
Dwyer G I, Gibbs M J, Gibbs A J and Jones R A C (2007) Plant Disease 91:164-170.
Ellis M H, Rebetzke G J and Chu P (2003) Plant Pathology 52:808-808.
Ellis M H, Rebetzke G J, Kelman W M, Moore C S and Hyles J E (2004) Plant Pathology 53:239-239.
Fagard M and Vaucheret H (2000) Annual Review of Plant Physiology and Plant Molecular Biology 51:167-194.
French R and Stenger D C (2003) Annu Rev Phytopathol 41:199-214.
Garfinkel et al. (1983) Cell 27: 143-153.
Gotor et al. (1993) Plant J. 3:509-518.
Greve (1983) J. Mol. Appl. Genet. 1: 499-511.
Harvey T L and Seifers D L (1991) Journal of the Kansas Entomological Society 64:18-22.
Hinchee et al. (1988) Biotech. 6:915.
Huang S S, Gilbertson L A, Adams T H, Malloy K P, Reisenbigler E K, Birr D H, Snyder M W, Zhang Q and Luethy M H (2004) Transgenic Research 13:451-461.
Jayaraj J, Liang G H, Muthukrishnan S and Punja Z K (2008) Biologia Plantarum 52:215-221.
Jiang J, Friebe B, Dhaliwal H S, Martin T J and Gill B S (1993) Theoretical and Applied Genetics 86:41-48.

Jones R A C, Coutts B A, Mackie A E and Dwyer G I (2005) Plant Disease 89:1048-1050.
Komari T, Hiei Y, Saito Y, Murai N and Kumashiro T (1996) Plant Journal 10:165-174.
Kwon et al. (1994) Plant Physiol. 105: 357-367.
Lee et al. (1993) Cell 75:843-854.
Li Z, Liu Y and Berger P H (2005). Biotechnology 4: 62-68.
Makkouk K and Kumari S (1997) Rachis 16:74-76.
Matsuoka et al. (1993) Proc. Natl. Acad. Sci. USA 90:9586-9590.
Matthews P R, Wang M B, Waterhouse P M, Thornton S, Fieg S J, Gubler F and Jacobsen J V (2001) Molecular Breeding 7:195-202.
Murray G, Simpfendorfer S, Hind-Lanioiselet T, Lanoiselet V and Wratten K (2007) in GRDC Research Update pp 63-69, Wagga Wagga: New South Wales Department of Primary Industries and EH Graham Center for agriculture Innovation.
Niedz et al. (1995) Plant Cell Reports 14: 403-406.
Nyitrai A (1991) Novenytermeles 40:21-26.
Orozco et al. (1993) Plant Mol. Biol. 23:1129-1138.
Ow et al. (1986) Science 234: 856-859.
Palatnik et al (2003) Nature 425:257-263
Parizotto et al (2004) Genes Dev 18:2237-2242.
Pawlowski W P and Somers D A (1996) Molecular Biotechnology 6:17-30.
Pellegrineschi A, Noguera L M, Skovmand B, Brito R M, Velazquez L, Salgado M M, Hernandez R, Warburton M and Hoisington D (2002) Genome 45:421-430.
Prasher et al. (1985) Biochem. Biophys. Res. Comm. 126: 1259-68.
Prols F and Meyer P (1992) Plant Journal 2:465-475.
Rabenstein F, Seifers D L, Schubert J, French R and Stenger D C (2002) Journal of General Virology 83:895-906.
Salomon et al. (1984) EMBO J. 3: 141-146.
Schwab et al (2006) Plant Cell 18: 1121-1133.
Seifers D L, Harvey T L, Martin T J and Jensen S G (1998) Plant Disease 82:875-879.
Seifers D L, Martin T J, Harvey T L and Gill B S (1995) Plant Disease 79:1104-1106.
Seifers D L, Martin T J, Harvey T L and Haber S (2007) Plant Disease 91:1029-1033.
Seifers D L, Martin T J, Harvey T L, Haber S and Haley S D (2006) Plant Disease 90:623-628.
Sharp G L, Martin J M, Lanning S P, Blake N K, Brey C W, Sivamani E, Qu R and Talbert L E (2002) Crop Sci 42:105-110.
Slykhuis J T (1955) Phytopathology 45:116-128.
Stalker et al. (1988) Science 242:419-423.
Stam M, deBruin R, Kenter S, vanderHoorn R A L, vanBlokland R, Mol J N M and Kooter J M (1997a) Plant Journal 12:63-82.
Stam M, Mol J N M and Kooter J M (1997b) Annals of Botany 79:3-12.
Stam M, Viterbo A, Mol J N M and Kooter J M (1998) Molecular and Cellular Biology 18:6165-6177.
Stenger D C, Hall J S, Choi I R and French R (1998) Phytopathology 88:782-787.
Stenger D C, Seifers D L and French R (2002) Virology 302:58-70.
Stockhaus et al. (1987) Proc. Natl. Acad. Sci. USA 84:7943-7947.
Stockhaus et al. (1989) EMBO J. 8:2445-2451.
Thillet et al. (1988) J. Biol. Chem. 263:12500.
Vidal J R, Kikkert J R, Donzelli B D, Wallace P G and Reisch B I (2006) Plant Cell Reports 25:807-814.
Wesley S V, Helliwell C A, Smith N A, Wang M B, Rouse D T, Liu Q, Gooding P S, Singh S P, Abbott D, Stoutjesdijk P A, Robinson S P, Gleave A P, Green A G and Waterhouse P M (2001) Plant Journal 27:581-590.
Yamamoto et al. (1994) Plant Cell Physiol. 35: 73-778.
Yamamoto et al. (1997) Plant J. 1:255-265.
Yin Z, Plader W and Malepszy S (2004) Journal of Applied Genetics 45:127-144.
Yu et al (2005). Science 307:932-935
Zhao Y, Qian Q, Wang H-Z, Huang D-N and Dutis D (2007) In Vitro Cellular and Developmental Biology—Plant 43:328-334.

```
Sequence of WSMV type strain (Genbank Accession No. AF285169
                                                  (SEQ ID NO: 1)
   1 aaattaaacc aacccaaatc gatctgacaa cgaacaaaac gaactcaaag cactcacaag 61 ctcaagttca acaaagttca tcacgcagaa agcaattcgt tcattgtgag ctctcgcata 121 gagataagca atggcaacag cgaattgttt gctcggtgac ttcggaaggc aggggtcgt 181 cgctaacgac ccatacgtac agtgcagagc gcgcacgctg attttcctaa gcactgaaga 241 ggaggttgat gtggtggtta accaccacgg accaggaagc attttctggt caaaagaagg 301 cattttaaca cagacggcta agaacctta caaagctact gcgtatggcc taggctacga 361 ccttgcagca aacgtcttcg tttgcggcaa gtgtaggtcc agctgcactc agtataggta 421 cttcattgag gatcactttg cctgcgacaa actcgtggag aagaactgcg cgtacatcaa 481 gaatgataag tacgtgaagg ttgtggaggc attcccaatt atgccatctt atgccacacc 541 agggcaagaa acacgcagca tacagtggat gaacaagaca agtcattgcc ttgctgatca 601 ctgcatccaa cgcgctcgcg agatcacttt caccaactca aaaactcaag aggaagaaac 661 tcgcgtgaag gattgcagta tggaagtgtt ttatgatgac ttcgacgaag ctcatgcagt 721 gattgagcac gcacatcgta agaatccggt tcacgaatat aaagagaagc agttacggat 781 gacttcaaat aacatagctg cgttagtgga ccaagtgaca cggatgatgc actccaaggg 841 caaaacagtg gaaatagttg ggagtaaagg ccataagaaa tttgccaaga ttccactgaa
```

-continued

```
 901 gcacacaatg ggatatccaa agcgggattg ggacgcatca aaggacatac cagaagatct
 961 cagaggcttt atcacaactt atagtggcgt catacaatac acacgcaaag tgcaggatca
1021 tgaagtgacg cttggatgga gtggtgttct tcttagtgag atggatgttc ctgatggcta
1081 tcaagaagat tgcgttgacg gtctatttat tgtcatggga agatgcgcac atggacgcat
1141 tcaaaacgca ctgaagccaa aatgcacaca tggatttaga tggtatggcg accaagcagt
1201 gaacaaagct attccgaaat accacgatgt gtgcaacaac aactgcgcaa gttacctgga
1261 agccttgcca agaaaggtta gccgtgtatg gcaatcaatg tttgacatac ataatctgag
1321 gtgcgaccaa tgtagaacag agtggaagat gcggacagct tcagagcatt tgcaattgtt
1381 acagaaatct gtggaatatt acatgcaaac gtatccagac agcgatgtaa cactgttcaa
1441 agcattcttg caagcactag ggccagatga agaggttgag gcacgccagc tcaaacccaa
1501 caatacattg caacttgtag atgtgtggcg aacaatgaaa aacacaataa acatcccgaa
1561 taggatcatc tacatgggca tgttcacgga caattatgga aattttgatt tctttccgaa
1621 cacatcaatg ccggaattat tcgccatgca catgcaaccg gtgcaacata agatgctaga
1681 agatggaaca attgaaacga attttaggtt cgttgatttg gagggaaaaa tccaaactag
1741 cattgaaagt ttgtatccga catttgacag cacatactgg aatgaacagg cacgcagagt
1801 tcacagaatc caaccgctag cagactgctt gatggaaatc aacggcgagt ctaagcccat
1861 ttgtcactgg gaaggaaatg tgcctttgta caatcccatt attcgtgcaa cgcctggaca
1921 attaccgttt ggagttataa cgcatttgct gagtgtaaat gacaggagtg gaagattcca
1981 ttatgtgccg aagaatgggt attgttacat gtacatattt gcctgtgcga tgattttctg
2041 tggtaatagc aatcgttcca cagttgacgc ctttgttcgg caagtttgcg aggatctggg
2101 tccttggcca acatttggtg atgtgctaag acaacttgat tggatggcga ccttttatgg
2161 atgttacgac gcattggtgc cagtaatttt ggtagaccac acaagaaaga ccatgcacgt
2221 gccaacacca tatggtataa agcaatcagg aatgcatacc atcagagtca acacagtgct
2281 agagttgata actctcgata ccatggccag tggagcaatg aaagattaca aaattggcgg
2341 gttccaagag acagttctta gcatacaagc atgcgtcaag agcagaaaag aatttgtgcg
2401 caaaatcaac aaggatgcag aatggttggt ggacatgttt attaatcctt caacgctctt
2461 cgtgttagga ggcttaattg aagtgcacca agtcattctt gctgatgtcg agaattcatt
2521 cgacaaatca gcagctttac taaacttgcg ccaaatagct ttaaagctcg gaccacattt
2581 ggaatcaaag cagcgcgtac gtcagtacat ggagttaatg attcagcatc gagcatcagt
2641 tgaagcaata atcccctcgc aacacatgaa agctgagatg atgcaataca ttgatgcact
2701 gcaacgctca attcttgagg agcaagtaat catagagatg gatcgagttg gaggaaagga
2761 aaaaatgctc gtcgagcaag atctttcaca cgcagagtgt gcgtacaacg agttcttcaa
2821 ctccattggc tatttaaact ttcatggaac cgttttacga ctcacatatt ctggtccagg
2881 aagaaaggtt ggagaagtgc tagagagttt aagagacaac tggttgacac gctatctccg
2941 aggaccgaag cagccgagag actacaaagg gagttccttg aggatttgga ggaaggttac
3001 tcacctttgc ggaaacgctt acaggtgggt attttacaac atggccgcga acgtcttgca
3061 agttatactc ataggccttt ctaccgtttt cggagcatat ttattaaaga agatcttaaa
3121 aatgctgcag tgggagaagg agcaagaaag caccgaattg gttgaatacc aagggaagcg
3181 agaggaagca tggataaccc gagtaatggc tgtattgtat ataatagctt cacttttctc
3241 cgtagatttt agttctgctt tatattcgaa tttggtgaag ttcagaacca tatttgacat
```

-continued

```
3301 cttgaagttt agttgcgagt atcagagtgg aattttttgaa agtttgaaaa atcaactcgg
3361 caacatccca gcgtttcatg aggtacattt gtatgaccat gaggcaacac aagtagcagt
3421 cccaccagct atattgacat tcgagcgatg gttcgagact cggatcacat ctggccagca
3481 aggatatgcg ccacttgatg gtagccacgt gagcttaacg atgacaaaag acacagttgg
3541 tgagatcgca acacaagttc aagcgcacaa ggcaaaggag tttctcatta taggacatgt
3601 tggatgtgga aaatctacag cttttccagc aacactctcc aggaatgggc gtgtgatgat
3661 atgtgaacca acccgcgtgc tagtcacaaa tttgcaggat tcaatgctag caacgaagaa
3721 tctaagcatc agtgccatga tgagaaacca ccgggttatg acggcgtcga acataacagt
3781 aactacgtat gggtatgcac tccactactt gtacaacaac tcacataacc tttcagaata
3841 tgattatatt cttttcgacg aagtgcacca aacctcggca gagatgctag tgttttacaa
3901 ctggcttaag agcacaacgt gggatggcaa gctcatcaag ttaacagcca cgaacaacac
3961 agttaatggc gacatgcaaa cacagcaagc ccttgatgtc aaaacgtggc cggttatgga
4021 tcacagaaca ttcatgcagg agcaaggtcg aggaacggct catgatgcat caactcttgg
4081 tgacgtcatc atagtctttt taacttcgtt tcgtgaaatt gatgaatctg ctgatatttt
4141 aagcaaaaat tcaaaaattg gcgtaataaa ggcagatagt cggcacttgc gaaacaaagt
4201 tagcttgatg gatgatgttg aagcactccg agctgagaag aaatacattc ttgcaactaa
4261 tattcttcaa aacggtgtga atttgcatgc agacgttgtc gttgattttg gcttcaagat
4321 tgtaccagcc attgacagcg acaatcggat gatcacagtc aagcgccaat gatcaacaa
4381 atcagatagg attcagagac taggacgagt gggccggatg aagatgggat acgcaaggaa
4441 aatcggaaat gaaatagatg cttcattcgc tttggatgaa gtcacagcta cggaagctgc
4501 cttgttggca tttggactcg gtgttgctcc agtgttgcag aatgttgacc aacacacatt
4561 cggaaaaata acagcagagc aagttcgaac agctgcacgc tttgaaatgc aattgtcgta
4621 tatggtgtgg atgatcaaca gagatggcac tatggccaca cggttatatg aacaattcaa
4681 atcattgctt ttaacaccag ggaacacgag tttggccccg tattatgaga cactcgttga
4741 cactcataga ttcagaacca ttggacaata cgcaactctt ggatacatgc gcacagacga
4801 aaagcatcat ttggtattac catttcacca caatgacgtg agcgttgaat ttgctgaaag
4861 gattggcgaa gcctatatag cctctcaagt cccgacatca attaagctgc gcgtacctgc
4921 ggtcaatcat agagaagtgg cgatgaagat gtcagcaaat cctgaagatg tgggaaccat
4981 attgtatatg gttgagcaag cgctaataag tgaaaagacg aaactggaga atctaactca
5041 ggcattccag cagcaacaat caacatattg cagcgtgctt attcctaatt tcaatgttgc
5101 tggtcggcta acacaggcaa tggatcgcat aagaaagaat gtttctgtgc tacaacacca
5161 aaaaacagct ctcgaaaagg cagcagtgac ttacgactac acgaagttag ttgagctcct
5221 tgacgaaaat ccaagcatag cttcccatgt ttcataccag gctgggccag caaaattcat
5281 tgatgaattc atattggaga agcgcgatta tgggtggcta ccgtatcttg cagtaggaac
5341 tgcgtgtgca attgctggca caacacttgt gatgatgtac taccgtcgca tgaagcgtag
5401 tgtcaagttc gagggcaaag cagcacgcaa cagtagtgca aaacgacaat cagcaagaga
5461 tcaaaagatg gagcgtggca acgaatacac atactacgat gctggtgaca ccttgtataa
5521 tggagttcaa gagaatatga atcatgcacc agactggacc gaccggatta agaagaagac
5581 tcatgcatac gcaatgcaat ttggtaggga agtaccaaaa actgaagcac agcgatcctc
5641 acaatactgg cacttctacg gttttgatcc aaagatgtat gattcagtcg aatttaagga
5701 catatcagca aacttctcag tgcatcagga tgcaaaggca atggatttgc agaaggcctt
```

-continued

```
5761 cacagaaatg gtggaaaatc gttgggatga tgaagacttc ttcgacgaga agatacccaaa
5821 gcgagttttg gccatcttca ggaaaggaga caaggttcgt gaagttgcat ggcaccctca
5881 caagccaaac caagtcaaca agcgtgggct acccgtcgga catgctgatc acagaggaga
5941 gtggagacaa acacagcctt catttgaaaa agaagtgtcg tacgagaaca aatcaacttt
6001 cgaaggtgca cgttcacttg atcatatcca tcagaatcaa gtcatcctcg ttgaagacaa
6061 tcaacagtta aatgggctaa tagttggaaa catactcttg gcgccatatc atttcacacg
6121 gggtatgagg aacagagagg agaaggaaac acgcatgttg acacagtttg gaacgtataa
6181 tcttggaaaa cttaccaaca agcatgtcac aaaattcaca atgatggatc tggtagcatt
6241 aacattacct ccaacatttc aagcaagacg gaaactcaaa tgtttcagac caccaaggga
6301 aggagagcga gcaatgctgg tgaccatgca gtacgagaaa gcaggatggg ttgccaagca
6361 atcagcggaa acaacaatca caccattcgg tgatcgacat gatggtttgt ggaagcatag
6421 aatttcaaca ggaccaggtg actgtggaag tgccatagta gcagtagcag acctaaaagt
6481 tgtgggattc cataaccttg agggaaaggt tgagaattac ttcacaccga taactattga
6541 ggtcatggat ttcttagctg aaaagtctgt aacaccgctt gtgccatgga agttctcaga
6601 cgagcaagtt gacttgtgtg gtttaattgc gaccaatgga gcagacaaat acccattcac
6661 caaaacaata agcgacttgg ttagttggca aagtctccaa atgacgaaat attgtgggga
6721 gaacttcaag gctatcgctt acgctccaaa ccgaatgtca aaaggcatg tcattacagg
6781 aaagaggcct gaattcatta aatttctaga ttcccacccg aagtggaatg cagtggtaac
6841 accttttctta aacgagtttc aaccatcagt cctgacacat gaagcatatt acaaggatgt
6901 gttgaagtat aacaaagaca taattgttgg agggactgac gaagtgtgtt tcgcgaaggc
6961 agtggtcgca accattggga ttctagaaat agccggattt caaagggac aatttcaacc
7021 aatctttgat ggatgtaaaa ttttcaatga cttgaattta gatgccgcaa tgggagcttt
7081 gtactcaggg aagaaatctg catactttga cggagcaaca agcgacgaaa tcaatgaatt
7141 ctttgaactg agtgcagcga agctactcag taacggacat ggagtatggt ctggtttact
7201 caaagctgag ttgagaccga aggcaaaggt cgtggcgaac aaaacgcgaa cattcacatc
7261 agcaccaatt gatatactca tgggtgccaa agctgtggtt gatgagttca acaaattctt
7321 ctacacaaag catctgcgcg gaccatggac cgtcggcatc aataagttta acggaggttg
7381 ggatttgttg gccaaaaatc taatggtgta cgagtggttc attgacgctg atggttctca
7441 attcgacagt tcaatcactc cacttctgat gaatgcaatt cttaacatac ggcaatactt
7501 catggcagaa gatgttgaag ctgaacaaat gctggcaaat ttgtatacgc aaattataaa
7561 cacatgcatt ttaattgaag atgggacgat tgtgcagaag tttcgaggta ataacagtgg
7621 ccaaccaagc acagttgtcg acaacacgat gtgtttaatc atagctatgg agtattgcag
7681 aatgcgtgta gaaaaggatc atggacatag aatgaggata ctgtacgtgt gcaacgggga
7741 tgatttgctt atcaatgccg acacaaagga caaagatttc atacagcagt attttgccga
7801 ttacatgcgc gaactggagc tgaattactc atttgacgag gcttaccgta gtatcgagga
7861 ggtggaatac atgtcacaca cattcatgaa gcgaaattcg atgtacattc caaagttgaa
7921 gcgcgaacga attgtggcaa tcctggagtg gcagaggagc aaggaaccga aggctattca
7981 gagcgctatt attgcagcat acgtggaagc tttcggttat gatgaattca cggagatgat
8041 tgaagaactt gcgcaggagg tttcagcggt gtggccagat ttcaagttgc cctcacgaca
8101 agaggttgag gatttgtact tgactgggac tcgaacggat ttaggagaag agattaagga
```

-continued

```
8161 atgtggagag caatactgcg tgtacgaatc gagtgaggcc gcaaccgacg ctgtcttggc
8221 ggcagcaaat gcaggaactg gtagtgaacc gagcagtgga agtactcaat caagtctgag
8281 cgcaagtact gctagcggat cagggagctc accatcagga tcaggttctg gagcagtggg
8341 tgaatcaggt tctggatcag cacaaacaca atctaataac gtatctgtca tggctggcct
8401 cgacacggga ggaactaaga caggtcaagg atcaggatca aaagggacga gtggttcatt
8461 cgtatcgaat cccgtgcgaa ctggaggccg agcaacggat gtgcaagatc agacaccagg
8521 gttagtgttt ccagcaccaa agatcacaac aaaggccata tacatgccaa aaactgtacg
8581 cgacaagata aagcctgaaa tgataaataa catgatcaaa taccaaccgc gtgcggaact
8641 tatcgacaac agatatgcaa caactgaaca gctcaacacc tggatagaag aggcatctga
8701 agggcttgac gtgacagagg aagttttcat aaacaccta cttccaggat gggtctacca
8761 ctgcataatc aacacaacga gcccagagaa cagagcacta ggaacttggc gtgttgtgaa
8821 taatgcaggc aaggacaatg agcagcaact cgagtttaaa attgaaccga tgtacaaagc
8881 cgcgaagcca tcacttcgag ccattatgcg tcactttggc gagggagctc gagtgatgat
8941 cgaggagagt gttcggattg gaaaacctat cataccaagg ggcttcgaca aggccggtgt
9001 gctaagcatc aacaatattg tggcagcgtg tgatttcatt atgcgcggtg cagatgacac
9061 accaaatttt gtgcaagtgc agaacagcgt tgcagtgaac aggctacgcg gaatacagaa
9121 caagctgttt gcacaggcac gactgagtgc gggtactaat gaggacaact cacgtcatga
9181 tgcagatgat gtgagggaga acacgcacag tttcaatggt gtaaacgctc ttgcgtgagc
9241 acagtagaaa ccacaaatcc acgagtacca ggatttgagc ggaataacgc tgcgtttcgt
9301 taacccttcg ttgttactag gtgtgtactt ctccacgaga ggcgtgcatt cttggtagct
9361 atgtgtgggt tagggcgacg ctac
```

What is claimed is:

1. A transgenic wheat plant, the wheat plant comprising a chimeric DNA molecule which encodes a dsRNA molecule
   a) comprising a double-stranded RNA portion of at least 150 contiguous basepairs comprising at least 150 nucleotides whose sequence is at least 98% identical to a corresponding region of Wheat Streak Mosaic Virus (WSMV) genomic RNA; or
   b) which is processed in the wheat plant into a silencing RNA molecule that is fully identical to, or fully complementary to, 21 to 24 consecutive nucleotides of WSMV genomic RNA;
   which is capable of inhibiting WSMV replication, such that the wheat plant is immune to WSMV.

2. The transgenic wheat plant as claimed in claim 1 in which the chimeric DNA encodes a dsRNA molecule comprising a double-stranded RNA portion of at least 150 contiguous basepairs comprising at least 150 nucleotides whose sequence is at least 98% identical to a corresponding region of the WSMV genomic RNA, which is a hairpin RNA molecule.

3. The transgenic wheat plant as claimed in claim 1 in which the chimeric DNA encodes two complementary RNA strands which are capable of annealing to form the dsRNA molecule.

4. The transgenic wheat plant as claimed in claim 1 in which the dsRNA is a pri-miRNA which is processed in the wheat plant into the silencing RNA molecule that is fully identical to, or fully complementary to, 21 to 24 consecutive nucleotides of the WSMV genomic RNA.

5. The transgenic wheat plant as claimed in claim 1 in which the chimeric DNA molecule comprises a promoter which directs expression by RNA polymerase II (Pol II) or RNA polymerase III (Pol III) which is operably linked to a DNA region encoding the dsRNA.

6. The transgenic wheat plant as claimed in claim 1 in which the wheat plant is a hexaploid wheat plant.

7. The transgenic wheat plant as claimed in claim 1 in which the wheat plant is homozygous for the chimeric DNA molecule.

8. The transgenic wheat plant as claimed in claim 1 in which the wheat plant does not comprise a transgene encoding an antibiotic-resistance marker.

9. The transgenic wheat plant as claimed in claim 1 in which the wheat plant is characterized by stable immunity to WSMV such that immunity is maintained in progeny plants.

10. The transgenic wheat plant as claimed in claim 1 in which the wheat plant is at least a third generation transgenic plant.

11. A chimeric DNA molecule, comprising
(i) a wheat expressible promoter;
(ii) a region which encodes a dsRNA
  a) comprising a double-stranded RNA portion of at least 150 contiguous basepairs comprising at least 150 nucleotides whose sequence is at least 98% identical to a corresponding region of WSMV genomic RNA, which is capable of inhibiting WSMV replication; or
  b) which is processed in a wheat plant into a silencing RNA molecule that is fully identical to, or fully complementary to, 21 to 24 consecutive nucleotides of WSMV genomic RNA, which is capable of inhibiting WSMV replication;
wherein said inhibition confers immunity to the plant to WSMV; and
(iii) optionally, a transcription termination signal.

12. A process for producing the transgenic wheat plant of claim 1, comprising
(I) introducing into a parental wheat cell a chimeric DNA molecule comprising
  (i) a wheat expressible promoter;
  (ii) a region which encodes a dsRNA
    a) comprising a double-stranded RNA portion of at least 150 contiguous basepairs comprising at least 150 nucleotides whose sequence is at least 98% identical to a corresponding region of the WSMV genomic RNA, which is capable of inhibiting WSMV replication; or
    b) which is processed in a wheat plant into a silencing RNA molecule which is capable of inhibiting WSMV replication, wherein the silencing RNA molecule is fully identical to, or fully complementary to, 21 to 24 consecutive nucleotides of the WSMV genomic RNA; and
  (iii) optionally, a transcription termination signal; and
(II) regenerating a wheat plant from the wheat cell comprising the chimeric DNA molecule; and
(III) identifying and/or selecting a plant obtained in step II which is immune to WSMV.

13. The process as claimed in claim 12 in which the process further comprises producing progeny plants from the wheat plant selected or identified in (III).

14. The transgenic wheat plant of claim 1, wherein the silencing RNA molecule has a 3' nucleotide which is methylated in its ribose moiety.

15. A process for producing wheat grain, comprising
i) growing a wheat plant according to claim 1,
ii) harvesting the grain from the wheat plant, and optionally
iii) processing the grain.

16. A process for producing wheat flour, wholemeal, bran or starch, comprising
i) obtaining grain from the wheat plant as claimed in claim 1; and
ii) milling the grain, and
iii) optionally, refining the milled grain thereby producing the wheat flour, wholemeal, bran or starch.

17. The transgenic wheat plant as claimed in claim 6 in which the hexaploid wheat plant is a *Triticum aestivum* ssp aestivum plant.

18. The transgenic wheat plant as claimed in claim 1 in which the wheat plant is immune to WSMV such that after inoculation of the plant with WSMV, the WSMV is undetectable by reverse transcription-polymerase chain reaction (RT-PCR).

19. The transgenic wheat plant as claimed in claim 1 in which the dsRNA molecule targets multiple regions of the WSMV genome and/or the (−) replicative strand.

* * * * *

SEQUENCE LISTING

<160> NUMBER OF SEQ ID NOS: 32

<210> SEQ ID NO 1
<211> LENGTH: 9384
<212> TYPE: DNA
<213> ORGANISM: Wheat streak mosaic virus

<400> SEQUENCE: 1

```
aaattaaacc aacccaaatc gatctgacaa cgaacaaaac gaactcaaag cactcacaag      60
ctcaagttca acaaagttca tcacgcagaa agcaattcgt tcattgtgag ctctcgcata     120
gagataagca atggcaacag cgaattgttt gctcggtgac ttcggaaggc aggggtcgt      180
cgctaacgac ccatacgtac agtgcagagc gcgcacgctg attttcctaa gcactgaaga     240
ggaggttgat gtgtggtta accaccacgg accaggaagc attttctggt caaagaagg       300
catttaaca cagacggcta agaaccttta caaagctact gcgtatggcc taggctacga     360
ccttgcagca aacgtcttcg tttgcggcaa gtgtaggtcc agctgcactc agtataggta     420
cttcattgag gatcactttg cctgcgacaa actcgtggag aagaactgcg cgtacatcaa     480
gaatgataag tacgtgaagg ttgtggaggc attcccaatt atgccatctt atgccacacc     540
agggcaagaa acacgcagca tacagtggat gaacaagaca agtcattgcc ttgctgatca     600
ctgcatccaa cgcgctcgcg agatcacttt caccaactca aaaactcaag aggaagaaac     660
tcgcgtgaag gattgcagta tggaagtgtt ttatgatgac ttcgacgaag ctcatgcagt     720
```

```
gattgagcac gcacatcgta agaatccggt tcacgaatat aaagagaagc agttacggat    780
gacttcaaat aacatagctg cgttagtgga ccaagtgaca cggatgatgc actccaaggg    840
caaaacagtg gaaatagttg ggagtaaagg ccataagaaa tttgccaaga ttccactgaa    900
gcacacaatg ggatatccaa agcgggattg ggacgcatca aaggacatac cagaagatct    960
cagaggcttt atcacaactt atagtggcgt catacaatac acacgcaaag tgcaggatca   1020
tgaagtgacg cttggatgga gtggtgttct tcttagtgag atggatgttc ctgatggcta   1080
tcaagaagat tgcgttgacg gtctatttat tgtcatggga gatgcgcac atggacgcat   1140
tcaaaacgca ctgaagccaa aatgcacaca tggatttaga tggtatggcg accaagcagt   1200
gaacaaagct attccgaaat accacgatgt gtgcaacaac aactgcgcaa gttacctgga   1260
agccttgcca agaaaggtta gccgtgtatg gcaatcaatg tttgacatac ataatctgag   1320
gtgcgaccaa tgtagaacag agtggaagat gcggacagct tcagagcatt tgcaattgtt   1380
acagaaatct gtggaatatt acatgcaaac gtatccagac agcgatgtaa cactgttcaa   1440
agcattcttg caagcactag ggccagatga agaggttgag gcacgccagc tcaaacccaa   1500
caatacattg caacttgtag atgtgtggcg aacaatgaaa acacaataa acatcccgaa   1560
taggatcatc tacatgggca tgttcacgga caattatgga aattttgatt tctttccgaa   1620
cacatcaatg ccggaattat tcgccatgca catgcaaccg gtgcaacata agatgctaga   1680
agatggaaca attgaaacga ttttaggtt cgttgatttg gagggggaaaa tccaaactag   1740
cattgaaagt ttgtatccga catttgacag cacatactgg aatgaacagg cacgcagagt   1800
tcacagaatc caaccgctag cagactgctt gatggaaatc aacggcgagt ctaagcccat   1860
ttgtcactgg gaaggaaatg tgcctttgta caatcccatt attcgtgcaa cgcctggaca   1920
attaccgttt ggagttataa cgcatttgct gagtgtaaat gacaggagtg aagattcca   1980
ttatgtgccg aagaatgggt attgttacat gtacatattt gcctgtgcga tgattttctg   2040
tggtaatagc aatcgttcca cagttgacgc ctttgttcgg caagtttgcg aggatctggg   2100
tccttggcca acatttggtg atgtgctaag acaacttgat tggatggcga ccttttatgg   2160
atgttacgac gcattggtgc cagtaatttt ggtagaccac acaagaaaga ccatgcacgt   2220
gccaacacca tatggtataa agcaatcagg aatgcatacc atcagagtca acacagtgct   2280
agagttgata actctcgata ccatggccag tggagcaatg aaagattaca aaattggcgg   2340
gttccaagag acagttctta gcatacaagc atgcgtcaag agcagaaaag aatttgtgcg   2400
caaaatcaac aaggatgcag aatggttggt ggacatgttt attaatcctt caacgctctt   2460
cgtgttagga ggcttaattg aagtgccaca agtcattctt gctgatgtcg agaattcatt   2520
cgacaaatca gcagctttac taaacttgcg ccaaatagct ttaaagctcg gaccacattt   2580
ggaatcaaag cagcgcgtac gtcagtacat ggagttaatg attcagcatc gagcatcagt   2640
tgaagcaata atcccctcgc aacacatgaa agctgagatg atgcaataca ttgatgcact   2700
gcaacgctca attcttgagg agcaagtaat catagagatg gatcgagttg gaggaaagga   2760
aaaaatgctc gtcgagcaag atcttttcaca cgcagagtgt gcgtacaacg agttcttcaa   2820
ctccattggc tatttaaact ttcatggaac cgttttacga ctcacatatt ctggtccagg   2880
aagaaaggtt ggagaagtgc tagagagttt aagagacaac tggttgacac gctatctccg   2940
aggaccgaag cagccgagag actacaaagg gagttccttg aggatttgga ggaaggttac   3000
tcacctttgc ggaaacgctt acaggtgggt attttacaac atggccgcga acgtcttgca   3060
agttatactc ataggccttt ctaccgtttt cggagcatat ttattaaaga agatcttaaa   3120
```

```
aatgctgcag tgggagaagg agcaagaaag caccgaattg gttgaatacc aagggaagcg   3180
agaggaagca tggataaccc gagtaatggc tgtattgtat ataatagctt cacttttctc   3240
cgtagatttt agttctgctt tatattcgaa tttggtgaag ttcagaacca tatttgacat   3300
cttgaagttt agttgcgagt atcagagtgg aattttgaa agtttgaaaa atcaactcgg    3360
caacatccca gcgtttcatg aggtacattt gtatgaccat gaggcaacac aagtagcagt   3420
cccaccagct atattgacat cgagcgatg gttcgagact cggatcacat ctggccagca    3480
aggatatgcg ccacttgatg gtagccacgt gagcttaacg atgacaaaag acacagttgg   3540
tgagatcgca acacaagttc aagcgcacaa ggcaaaggag tttctcatta taggacatgt   3600
tggatgtgga aaatctacag cttttccagc aacactctcc aggaatgggc gtgtgatgat   3660
atgtgaacca acccgcgtgc tagtcacaaa tttgcaggat tcaatgctag caacgaagaa   3720
tctaagcatc agtgccatga tgagaaacca ccgggttatg acggcgtcga acataacagt   3780
aactacgtat gggtatgcac tccactactt gtacaacaac tcataaacc tttcagaata    3840 tgattatatt cttttcgacg aagtgcacca aacctcggca gagatgctag tgttttacaa   3900
ctggcttaag agcacaacgt gggatggcaa gctcatcaag ttaacagcca cgaacaacac   3960
agttaatggc gacatgcaaa cacagcaagc ccttgatgtc aaaacgtggc cggttatgga   4020
tcacagaaca ttcatgcagg agcaaggtcg aggaacggct catgatgcat caactcttgg   4080
tgacgtcatc atagtctttt taacttcgtt tcgtgaaatt gatgaatctg ctgatatttt   4140
aagcaaaaat tcaaaaattg gcgtaataaa ggcagatagt cggcacttgc gaaacaaagt   4200
tagcttgatg gatgatgttg aagcactccg agctgagaag aaatacattc ttgcaactaa   4260
tattcttcaa aacggtgtga atttgcatgc agacgttgtc gttgattttg gcttcaagat   4320
tgtaccagcc attgacagcg acaatcggat gatcacagtc aagcgccaat tgatcaacaa   4380
atcagatagg attcagagac taggacgagt gggccggatg aagatgggat acgcaaggaa   4440
aatcggaaat gaaatagatg cttcattcgc tttggatgaa gtcacagcta cggaagctgc   4500
cttgttggca tttggactcg gtgttgctcc agtgttgcag aatgttgacc aacacacatt   4560
cggaaaaata acagcagagc aagttcgaac agctgcacgc tttgaaatgc aattgtcgta   4620
tatggtgtgg atgatcaaca gagatggcac tatggccaca cggttatatg aacaattcaa   4680
atcattgctt ttaacaccag ggaacacgag tttggccccg tattatgaga cactcgttga   4740
cactcataga ttcagaacca ttggacaata cgcaactctt ggatacatgc gcacagacga   4800
aaagcatcat ttggtattac catttcacca caatgacgtg agcgttgaat ttgctgaaag   4860
gattggcgaa gcctatatag cctctcaagt cccgacatca attaagctgc gcgtacctgc   4920
ggtcaatcat agagaagtgg cgatgaagat gtcagcaaat cctgaagatg tgggaaccat   4980
attgtatatg gttgagcaag cgctaataag tgaaaagacg aaactggaga atctaactca   5040
ggcattccag cagcaacaat caacatattg cagcgtgctt attcctaatt tcaatgttgc   5100
tggtcggcta acacaggcaa tggatcgcat aagaaagaat gtttctgtgc tacaacacca   5160
aaaaacagct ctcgaaaagg cagcagtgac ttacgactac acgaagttag ttgagctcct   5220
tgacgaaaat ccaagcatag cttcccatgt ttcataccag gctgggccag caaaattcat   5280
tgatgaattc atattggaga gcgcgatta tgggtggcta ccgtatcttg cagtaggaac    5340
tgcgtgtgca attgctggca caacacttgt gatgatgtac taccgtcgca tgaagcgtag   5400
tgtcaagttc gagggcaaag cagcacgcaa cagtagtgca aaacgacaat cagcaagaga   5460
tcaaaagatg gagcgtggca acgaatacac atactacgat gctggtgaca ccttgtataa   5520
```

```
tggagttcaa gagaatatga atcatgcacc agactggacc gaccggatta agaagaagac    5580
tcatgcatac gcaatgcaat ttggtaggga agtaccaaaa actgaagcac agcgatcctc    5640
acaatactgg cacttctacg gttttgatcc aaagatgtat gattcagtcg aatttaagga    5700
catatcagca aacttctcag tgcatcagga tgcaaaggca atggatttgc agaaggcctt    5760
cacagaaatg gtggaaaatc gttgggatga tgaagacttc ttcgacgaga agataccaaa    5820
gcgagttttg gccatcttca ggaaaggaga caaggttcgt gaagttgcat ggcacctca     5880 caagccaaac caagtcaaca agcgtgggct acccgtcgga catgctgatc acagaggaga    5940
gtggagacaa acacagcctt catttgaaaa agaagtgtcg tacgagaaca atcaacttt     6000 cgaaggtgca cgttcacttg atcatatcca tcagaatcaa gtcatcctcg ttgaagacaa    6060
tcaacagtta aatgggctaa tagttggaaa catactcttg gcgccatatc atttcacacg    6120
gggtatgagg aacagagagg agaaggaaac acgcatgttg acacagtttg aacgtataa     6180 tcttggaaaa cttaccaaca agcatgtcac aaaattcaca atgatggatc tggtagcatt    6240
aacattacct ccaacatttc aagcaagacg gaaactcaaa tgtttcagac caccaaggga    6300
aggagagcga gcaatgctgg tgaccatgca gtacgagaaa gcaggatggg ttgccaagca    6360
atcagcggaa acaacaatca caccattcgg tgatcgacat gatggtttgt ggaagcatag    6420
aatttcaaca ggaccaggtg actgtggaag tgccatagta gcagtagcag acctaaaagt    6480
tgtgggattc cataaccttg gagggaaagg tgagaattac ttcacaccga taactattga    6540
ggtcatggat ttcttagctg aaaagtctgt aacaccgctt gtgccatgga agttctcaga    6600
cgagcaagtt gacttgtgtg gtttaattgc gaccaatgga gcagacaaat acccattcac    6660
caaaacaata agcgacttgg ttagttggca aagtctccaa atgacgaaat attgtgggga    6720
gaacttcaag gctatcgctt acgctccaaa ccgaatgtca aaaaggcatg tcattacagg    6780
aaagaggcct gaattcatta aatttctaga ttcccacccg aagtggaatg cagtggtaac    6840 accttctta aacgagtttc aaccatcagt cctgacacat gaagcatatt acaaggatgt    6900
gttgaagtat aacaaagaca taattgttgg agggactgac gaagtgtgtt tcgcgaaggc    6960
agtggtcgca accattggga ttctagaaat agccggattt tcaaagggac aatttcaacc    7020
aatctttgat ggatgtaaaa ttttcaatga cttgaattta gatgccgcaa tgggagcttt    7080
gtactcaggg aagaaatctg catactttga cggagcaaca agcgacgaaa tcaatgaatt    7140
ctttgaactg agtgcagcga agctactcag taacggacat ggagtatggt ctggtttact    7200
caaagctgag ttgagaccga aggcaaaggt cgtggcgaac aaaacgcgaa cattcacatc    7260
agcaccaatt gatatactca tgggtgccaa agctgtggtt gatgagttca caaaattctt    7320
ctacacaaag catctgcgcg gaccatggac cgtcggcatc aataagttta acggaggttg    7380
ggatttgttg gccaaaaatc taatggtgta cgagtggttc attgacgctg atggttctca    7440
attcgacagt tcaatcactc cacttctgat gaatgcaatt cttaacatac ggcaatactt    7500
catggcagaa gatgttgaag ctgaacaaat gctggcaaat ttgtatacgc aaattataaa    7560
cacatgcatt ttaattgaag atgggacgat tgtgcagaag tttcgaggta ataacagtgg    7620
ccaaccaagc acagttgtcg acaacacgat gtgtttaatc atagctatgg agtattgcag    7680
aatgcgtgta gaaaaggatc atggacatag aatgaggata ctgtacgtgt gcaacgggga    7740
tgatttgctt atcaatgccg acacaaagga caaagatttc atacagcagt attttgccga    7800
ttacatgcgc gaactggagc tgaattactc atttgacgag gcttaccgta gtatcgagga    7860
ggtggaatac atgtcacaca cattcatgaa gcgaaattcg atgtacattc caaagttgaa    7920
```

```
gcgcgaacga attgtggcaa tcctggagtg gcagaggagc aaggaaccga aggctattca    7980
gagcgctatt attgcagcat acgtggaagc tttcggttat gatgaattca cggagatgat    8040
tgaagaactt gcgcaggagg tttcagcggt gtggccagat ttcaagttgc cctcacgaca    8100
agaggttgag gatttgtact tgactgggac tcgaacggat ttaggagaag agattaagga    8160
atgtggagag caatactgcg tgtacgaatc gagtgaggcc gcaaccgacg ctgtcttggc    8220
ggcagcaaat gcaggaactg gtagtgaacc gagcagtgga agtactcaat caagtctgag    8280
cgcaagtact gctagcggat cagggagctc accatcagga tcaggttctg gagcagtggg    8340
tgaatcaggt tctggatcag cacaaacaca atctaataac gtatctgtca tggctggcct    8400
cgacacggga ggaactaaga caggtcaagg atcaggatca aaagggacga gtggttcatt    8460
cgtatcgaat cccgtgcgaa ctggaggccg agcaacggat gtgcaagatc agacaccagg    8520
gttagtgttt ccagcaccaa agatcacaac aaaggccata tacatgccaa aaactgtacg    8580
cgacaagata aagcctgaaa tgataaataa catgatcaaa taccaaccgc gtgcggaact    8640
tatcgacaac agatatgcaa caactgaaca gctcaacacc tggatagaag aggcatctga    8700
agggcttgac gtgacagagg aagttttcat aaacacctta cttccaggat gggtctacca    8760
ctgcataatc aacacaacga gcccagagaa cagagcacta ggaacttggc gtgttgtgaa    8820
taatgcaggc aaggacaatg agcagcaact cgagtttaaa attgaaccga tgtacaaagc    8880
cgcgaagcca tcacttcgag ccattatgcg tcactttggc gagggagctc gagtgatgat    8940
cgaggagagt gttcggattg gaaaacctat cataccaagg ggcttcgaca aggccggtgt    9000
gctaagcatc aacaatattg tggcagcgtg tgatttcatt atgcgcggtg cagatgacac    9060
accaaatttt gtgcaagtgc agaacagcgt tgcagtgaac aggctacgcg gaatacagaa    9120
caagctgttt gcacaggcac gactgagtgc gggtactaat gaggacaact cacgtcatga    9180
tgcagatgat gtgagggaga acacgcacag tttcaatggt gtaaacgctc ttgcgtgagc    9240
acagtagaaa ccacaaatcc acgagtacca ggatttgagc ggaataacgc tgcgtttcgt    9300
taacccttcg ttgttactag gtgtgtactt ctccacgaga ggcgtgcatt cttggtagct    9360
atgtgtgggt tagggcgacg ctac                                          9384

<210> SEQ ID NO 2
<211> LENGTH: 37
<212> TYPE: DNA
<213> ORGANISM: Wheat streak mosaic virus

<400> SEQUENCE: 2
gttcattgtg agctctcgca tagagataag caatggc                              37

<210> SEQ ID NO 3
<211> LENGTH: 26
<212> TYPE: DNA
<213> ORGANISM: Wheat streak mosaic virus

<400> SEQUENCE: 3
ggaccaggaa gcattttctg gtcaaa                                          26

<210> SEQ ID NO 4
<211> LENGTH: 31
<212> TYPE: DNA
<213> ORGANISM: Wheat streak mosaic virus

<400> SEQUENCE: 4
tcgagcaaga tctttcacac gcagagtgtg c                                    31
```

<210> SEQ ID NO 5
<211> LENGTH: 22
<212> TYPE: DNA
<213> ORGANISM: Wheat streak mosaic virus

<400> SEQUENCE: 5
tacgactcac atattctggt cc                                              22

<210> SEQ ID NO 6
<211> LENGTH: 23
<212> TYPE: DNA
<213> ORGANISM: Wheat streak mosaic virus

<400> SEQUENCE: 6
tacaaaggga gttccttgag gat                                             23

<210> SEQ ID NO 7
<211> LENGTH: 32
<212> TYPE: DNA
<213> ORGANISM: Wheat streak mosaic virus

<400> SEQUENCE: 7
tggaggaagg ttactcacct ttgcggaaac gc                                   32

<210> SEQ ID NO 8
<211> LENGTH: 65
<212> TYPE: DNA
<213> ORGANISM: Wheat streak mosaic virus

<400> SEQUENCE: 8
ttttacaaca tggccgcgaa cgtcttgcaa gttatactca taggcctttc taccgttttc     60
ggagc                                                                 65

<210> SEQ ID NO 9
<211> LENGTH: 29
<212> TYPE: DNA
<213> ORGANISM: Wheat streak mosaic virus

<400> SEQUENCE: 9
tatttattaa agaagatctt aaaaatgct                                       29

<210> SEQ ID NO 10
<211> LENGTH: 38
<212> TYPE: DNA
<213> ORGANISM: Wheat streak mosaic virus

<400> SEQUENCE: 10
gatgatgtga gggagaacac gcacagtttc aatggtgt                             38

<210> SEQ ID NO 11
<211> LENGTH: 37
<212> TYPE: DNA
<213> ORGANISM: Wheat streak mosaic virus

<400> SEQUENCE: 11
gccattgctt atctctatgc gagagctcac aatgaac                              37

<210> SEQ ID NO 12
<211> LENGTH: 22
<212> TYPE: DNA
<213> ORGANISM: Wheat streak mosaic virus

<400> SEQUENCE: 12

```
tcaccgagca acaattcgc tg                                              22

<210> SEQ ID NO 13
<211> LENGTH: 26
<212> TYPE: DNA
<213> ORGANISM: Wheat streak mosaic virus

<400> SEQUENCE: 13
tttgaccaga aaatgcttcc tggtcc                                         26

<210> SEQ ID NO 14
<211> LENGTH: 31
<212> TYPE: DNA
<213> ORGANISM: Wheat streak mosaic virus

<400> SEQUENCE: 14
gcacactctg cgtgtgaaag atcttgctcg a                                   31

<210> SEQ ID NO 15
<211> LENGTH: 22
<212> TYPE: DNA
<213> ORGANISM: Wheat streak mosaic virus

<400> SEQUENCE: 15
ggaccagaat atgtgagtcg ta                                             22

<210> SEQ ID NO 16
<211> LENGTH: 23
<212> TYPE: DNA
<213> ORGANISM: Wheat streak mosaic virus

<400> SEQUENCE: 16
atcctcaagg aactcccttt gta                                            23

<210> SEQ ID NO 17
<211> LENGTH: 32
<212> TYPE: DNA
<213> ORGANISM: Wheat streak mosaic virus

<400> SEQUENCE: 17
gcgtttccgc aaaggtgagt aaccttcctc ca                                  32

<210> SEQ ID NO 18
<211> LENGTH: 65
<212> TYPE: DNA
<213> ORGANISM: Wheat streak mosaic virus

<400> SEQUENCE: 18
gctccgaaaa cggtagaaag gcctatgagt ataacttgca agacgttcgc ggccatgttg    60
taaaa                                                                65

<210> SEQ ID NO 19
<211> LENGTH: 29
<212> TYPE: DNA
<213> ORGANISM: Wheat streak mosaic virus

<400> SEQUENCE: 19 agcatttta agatcttctt taataaata                                       29

<210> SEQ ID NO 20
<211> LENGTH: 38
<212> TYPE: DNA
<213> ORGANISM: Wheat streak mosaic virus
```

-continued

```
<400> SEQUENCE: 20
acaccattga aactgtgcgt gttctccctc acatcatc                                 38

<210> SEQ ID NO 21
<211> LENGTH: 21
<212> TYPE: RNA
<213> ORGANISM: Wheat streak mosaic virus

<400> SEQUENCE: 21
agcucucgca uagagauaag c                                                   21

<210> SEQ ID NO 22
<211> LENGTH: 21
<212> TYPE: RNA
<213> ORGANISM: Wheat streak mosaic virus

<400> SEQUENCE: 22
ucgagcaaga ucuuucacac g                                                   21

<210> SEQ ID NO 23
<211> LENGTH: 21
<212> TYPE: RNA
<213> ORGANISM: Wheat streak mosaic virus

<400> SEQUENCE: 23
ugaccagaaa augcuuccug g                                                   21

<210> SEQ ID NO 24
<211> LENGTH: 21
<212> TYPE: RNA
<213> ORGANISM: Wheat streak mosaic virus

<400> SEQUENCE: 24
uaacuugcaa gacguucgcg g                                                   21

<210> SEQ ID NO 25
<211> LENGTH: 21
<212> TYPE: RNA
<213> ORGANISM: Wheat streak mosaic virus

<400> SEQUENCE: 25
ucggcacaua auggaaucuu c                                                   21

<210> SEQ ID NO 26
<211> LENGTH: 9352
<212> TYPE: DNA
<213> ORGANISM: Wheat streak mosaic virus

<400> SEQUENCE: 26
aaattaaacc aacccaaatc gatctgacaa cgaacaaaac gaactcacag cattcttaag         60
ctcaagttca acaaagttca ttgcgcagaa agcaattcgt tcattgtgag ctctcgcata        120
gagataagca atggcagcag cgaattgttt gctcggtgac ttcggaaggc aggggtcgt         180 cgctaatgac ccatatgtac agtgcagggc gcgcacgctg attttcttaa gcactgagga        240
ggaggttgat gtggtggtta accaccatgg accaggaagc attttctggt caaaagaagg        300
tatcttaacc cagacggcta agaacctcta caaagctact gcgtacggct taggctacga        360
tcttgcagcg aacgttttcg tttgcgggaa gtgtaggtca agttgcactc agtacaggta        420
cttcattgaa gatcattttg cttgtgacaa gcttgtggag aagaactgtg cgtacatcaa        480
ggatgataag tacgtgaagg tcgtggaggc atttccaatt atgccatcat acgccacacc        540
```

```
agggcaggaa gcacgcatca tacagtggat gaacaaaaca agccaatgcc ttgctgatca      600
ctgcatccaa cgcacgcgtg agatcacctt caccaactca aaacccaag aggaagaaac       660 tcgcgtaaag gattgcagta ttgaggtgtt ttatgatgat tttgatgaaa cacatgcagt      720
tattgagcat gctcatcgta agaatccgat ccacgagtac aaagagaagc agctacgcat      780
gacatcaaac aacatagctg cgttggtgga tcaagtgaca cggatgatgc attccaaggg      840
caaaacagtg gaaatcatag gaagcaaagg gcacaagaaa tttgctaaaa ttccactgaa      900
gcatacaatg gggtacccaa agagagattg ggatgcaatg aaagacatac cagaggactt      960
cagaggcttc atcacaacct acagcggtgt tatacaatac acacgtaaag tgcaggatca     1020
tgaggtgacg ctcggatgga gtggtgtcct ccttagtgaa atggatgtgc agatggctac     1080
caggaggatt gtgtggatgg cctattcatt gttatgggaa gatgtgcact ggacgcattc     1140
agaacgcact gaagccgaaa tgcacgcatg gacttagatg gtattgcgac cagctgtgaa     1200
caaagtgatt ccaaaacatc atgaagtgtg caacagtaac tgcgcaatta tctggaagca     1260
ttaccaagaa aggttagtcg tgtgtggcaa tcaatgttcg acataccaac ctgaggtgcg     1320
atttgtgcag agcagagtgg aagacgcgaa ctgcttcaga gcattgcagt tgctacagaa     1380
atctgtagag cattacatgc agacgtatcc agacagcgat gtaaattgtt caaggcgttt     1440
ttacaagcac ttggaccaga tgaggaagtc gaaacacgtc aactaaacct aacaatacat     1500
tgcaacttgt ggatgtgtgg cggacaatga agaacacgat aacatcccaa atagaatcat     1560
ctacatgggc atgttcacag acaattatgg aaatttcgat tcttcccaaa tacatcaatg     1620
cctgaactat tcgcaatgca catgcaacca gttcaacaca gatgctagat gatggaacaa     1680
ttgaaacgaa ttttagattc gttgatttag aagggaaaac cagacgagca tcgaaagttt     1740
atacccgaaa ttcgacagca catactggaa cgaacaagac gcaaagtcca cagaatccaa     1800
ccgttgacag attgctccat ggaaattaac ggcgaattaa gcccatttgt cattgggagg     1860
ggaatgttcc gttgtacaat cccataatcc gtgcaaacca gggcaactac catttggagt     1920
aactacgcac ttgctgagtg tgaacgacag gagcgaagat ttcattatgt gccgaagaac     1980
ggatattgct acatgtacat cttttgcatgc gcaagatctt ctgtggtaat agcaaccgtt     2040
cgacagttga tgcatttgtc cggcaagttt gcgagatctg ggtccctggc ctacatttgg     2100
tgaggtattg agacaacttg actggatggc aacttttatg ggtgttatga tgcactggtg     2160
ccagtaatct tagtggatca cacgaggaag atatgcacgt gccaacgcca tatggcatga     2220
aacaatcagg aatgcacacc ataagggtta cacagtactg gaactgataa ccctcgacac     2280
catggccagc ggagcaatga aggattacag attggcggat ccaagacac tgttctcggc       2340 atacaagcgt gtgtcaagag caggaaggat ttgtgcgtaa atcaacaaa gatgctgaat        2400 ggttagtgga tatgttcatt aatccttgac actctttgtg ttaggggtc taattgaagt        2460 tcaccaagtt attctcgcag atgttggaat tcattcgata aatcagcagc tctactgaac       2520
ttgcgccaga tagccctaaa gctcgacctc acttggaatc gaaacagcgc gtgcgtcaat      2580
acatggagtt aatgattcaa caccagcatc agttgaagca ataattccat cacaacacat      2640
gaaagctgag atgatgcaat acacgacgcg ctacaacgct caattcttga agagcaagtg     2700
atcatagaga tggatcgagt tgaggaaagg aaaaaatgct cgtcgagcaa atctttcac       2760 acgcagagtg tgcgtacaac gagttcttca actccattgg ttacttaaac tttcatggaa     2820
ccgttttacg actcacatat tctggtcccg gaagaaaggt tggagaagtg ctagagagtt     2880
taaaagacaa ctggttgaca cgctatctcc gaggaccgaa gcagccgaga gattacaaag    2940
```

```
ggagttcctt gaggatctgg aggaaggtta ctcacctttg cggaaacgct tacaggtggg    3000
tgttttacaa catggccgcg aacgtcttgc aagttatact cataggcctt tctaccgttt    3060
tcggagccta tttattaaag aagatcttaa aaatgcttca atgggagaag gagcaagaaa    3120
gcaccgaatt ggttgaatac caagggaagc gagaggaagc atggataaca cgagtaatgg    3180
ctgtattgta tataatagct tcactctttt ctgtagactt tagttctgct ttatattcga    3240
atttggttaa atttagaacc atatttgata ttttaaagtt taactgtgaa taccagagtg    3300
gaatatttga aagtttgaaa aatcaactcg gcaacatccc agcatttcat gaagtgcatt    3360
tgtacgacca cgaggcaaca caagtagcag ttccaccagc cattttaacg tttgaacgat    3420
ggtttgaaac tcgaatcact tctggccaac aagggtacgc accattagat ggtagccatg    3480
taagcttaac aatgacaaaa gacacagtcg gtgaaatcgc tacacaagtg cagacacaca    3540
aggcgaagga atttctcatc ataggacatg ttgggtgtgg aaaatccaca gcctttccag    3600
caacgctctc ccggaatggg cgtgtcatga tttgcgaacc tacccgcgtg ctggtaacaa    3660
acttgcaaga ttcaatgtta gcaacgaaga atttaagtat cagcgccatg atgaggaacc    3720
atcgggttat gacggcgtcg aatataactg taaccacgta tgggtatgca ctccattatt    3780
tgtacaacaa ctcacacaac cttgcagagt atgactacat tcttttgac gaagtgcatc     3840 aaacctcggc agaaatgcta gtgttttaca actggcttaa gagcacaacg tgggagggca    3900
aactcattaa gttaacagct acaaacaaca ccgtcaatgg agacatgcaa acacagcagg    3960
cacttgatgt caaaacatgg ccagttatgg accacaggac attcatgcag gagcaaggcc    4020
ggggaactgc ccacgatgca tccactcttg gtgatgttat catagtgttc ttaacttcgt    4080
tccgcgagat tgacgaatct gccgacattt tgagcaaaaa cccaaagatt ggagtcataa    4140
aggcagatag tcgccacttg cgaaacaaag ttagcttaat ggatgatgtt gaagcactcc    4200
gagctgaaaa gaaatacatc cttgcaacga acatccttca aaacggtgtg aatttgcacg    4260
cagacgttgt agttgatttt ggtttcaaga ttgtgccagc aattgacagc gacaatcgaa    4320
tgattacagt taagcgccaa ctgatcaaca aatcagaccg aattcagaga ttgggacgag    4380
taggccggat gaagatggga tacgcaagga aaatcggaaa tgagatagac gcatcgttcg    4440
ccttggatga agtgacagct acggaagctg ccttgttggc atttggacta ggtgttgctc    4500
cagtgttgca aaatgttgat caacacacat tcggaaagat tacagcagag caagttcgaa    4560
cagcagcacg atttgagatg caattgtcat acatggtgtg gatgattaat agagatggaa    4620
ccatggccac acggttatat gaacaattta agtcactctt gctaacacca ggaaacacga    4680
gtttggcacc gtattacgag acgcttgtag acactcacag gttcagaact attggtcaat    4740
atgcaactct gggatacatg cgcacagatg agaaacacca tttggttctc ccatttcacc    4800
ataatgatgt tagcgttgaa tttgcagaga ggattggtga agcgtatatg gcttctcaag    4860
tcccaacatc aatcaagttg cgtgtgccag cagttaacca cagagaggtg gctatgaaga    4920
tgtcagcaaa tcctgaagat gtgggaacca tactgtacat ggttgagcaa gcactgatta    4980
gcgagaagac aaaactggaa aatctcactc aggcgttcca gcaacaacag tcaacatatt    5040
gcagtgtgct cattcctaat ttcaacgttg ctggtagact gacacaggcg atggatcgca    5100
ttagaaagaa tgtctcagtg ctacaacacc agaaaacagc tcttgagaag gcggcagtga    5160
catatgatta cacaaagtta gttgagctcc ttgatgaaaa tccaagcata gcttctcatg    5220
tgtcatacca agctgggcca gcaaagttca ttgatgaatt catattggag aagcgtgatt    5280
atggatggct tccatatctt gcggtgggaa ctgcatgtgc gatagctggt acaacacttg    5340
```

```
tgatgatgta ctaccgtcgc atgaagcgca gtgttaaatt cgagggcaag gcagaacgca    5400
acaggagcgc gaagcgacag tcagccagag accagaagat ggagcgtggt aatgaataca    5460
catactatga cgccggcgac actttgtaca atggggttca agagaatatg aatcatgcac    5520
cagattggac tgaccgaatc aagaagaaaa ccaatgcata tgcaatgcaa tttggtaggg    5580
aagtgccaaa gaccgaaaca cagcgatctt cccaatattg gcatttctat ggatttgatc    5640
caaagatgta cgattcggtt gaattcaagg atatagccgc taacttttca gtgcatcagg    5700
atgccaaggc aatggatctg cagaaagcct tcacagaaat ggtggagaat cgttgggatg    5760
atgatgattt ctttgacgag aaaataccga agcgagttct agccatcttc agaaaagggg    5820
acaaagttcg tgaggtcgca ttggcacctc acaagccaaa ccaagttaac aagcgtgggc    5880
tacctgttgg gcatgctgac cacagaggag aatggcgaca acacaaccca tcgtttgaga    5940
aagaagtgtc atacgagaac aaatcaacct ttgaaggggc acgctcactt gatcatatcc    6000
atcagaatca ggttattctt gttgaggaca accaacagtt gaatgggtta atagtcggaa    6060
atatactctt ggcgccgtat cacttcacgc gaggtatgag gaacagagaa gagaaggaaa    6120
cacgcatgtt aacacaattt ggaacataca atcttggaaa actcaccaac aagcatgtca    6180
caaagtttac gatgatggat ttggttgcat taaccttacc tccgactttc caagcaagac    6240
ggaagcttaa gtgtttcaga ccaccacggg aaggagaacg agcaatgtta gtaaccatgc    6300
aatacgagaa aactggatgg gtcgctaagc aatcagcgga acaacaatc acaccattcg    6360 gtgatcgaca tgatggtttg tggaagcaca gaatctcgac aggaccagga gattgtggaa    6420
gcgctatagt ggcagtagca gacttgaagg ttgttgggtt ccataatctt ggagggaaag    6480
gcgagaatta tttcacgccg ataaccattg aagtcatgga tttcctagct gaaaagtccg    6540
taacaccact tgttccatgg aaattttcag atgagcaagt tgatctgtgc ggtttaattg    6600
cggccaatgg agcagacaaa tacccatttta ccaaaactat aagcgatttg gttagctggc    6660
aaagccttca gatgacaaaa tattgtgggg agaatttcaa ggctattgct tatgctccaa    6720
accgaatgtc aaagagacac gtcatcacag gaaagaggcc cgagttcatc aagtttctag    6780
actcccaccc gaaatggaac actctggtga cacctttcct gaacgaattc caaccatcag    6840
ttctgacaca tgaagcatat tacaaggatg tactgaagta caacaaggac ataattgttg    6900
gaggaactga tgaagtgtgc tttgcgaaag cagtggttgc taccattgga attctcgaaa    6960
tagccgggtt ttcaaagggt caattccagc ccatctttga cggatgcaaa atttcaacg    7020 atttgaatct ggatgctgca atgggagctc tatattcagg gaagaaggct gcatactttg    7080
acggagcaac aagtgatgaa atcaacgagt tctttgagtt gagcgcagcg aagttgctca    7140
gtaatggaca cggagtgtgg tctggttttgc taaaggctga gttgagaccg aaggctaaag    7200
ttgtggcaaa caagacgaga acattcacat cagcaccgat tgacatactt atgggcgcca    7260
aggctgtggt tgatgagttt aacaagtttt tctacacaaa acacctgcgt gggccatgga    7320
cagtaggcat caacaaattc aatggtgggt gggatttgct agctaaaaac ttgatggtgc    7380
acgagtggtt catagatgct gatggctctc aatttgatag ctcaatcact ccgctttga    7440 tgaatgcaat tttgaacata aggcagtact tcatggcaga ggacgatgag gctgagcaga    7500
tgttggcaaa tttgtacacg cagataataa acacatgcat cttaattgaa gatggtacga    7560
ttgtgcaaaa gtttcgaggt aacaacagtg gtcaaccaag cacagtcgtt gacaacacga    7620
tgtgcctgat catagcaatg gagtattgca gaatgcgtgt ggagaaagat cacggacaca    7680
gcatgaggat actatatgtg tgcaatggag atgatctact tatcaatgcc gacacaaagg    7740
```

```
ataaagactt catacagcag ttctttgccg actacatgcg cgagttggag ctgaattatt    7800
catttgatga agcgtatcgt agcatcgagg aggttgagta catgtcacac acattcatga    7860
agcgaggctc aatgtacata ccaaagttga agcgcgaacg cattgtggca attctagagt    7920
ggcagagaag caaggaacca aaggctattc agagtgccat cattgcagca tatgtggaag    7980
cttttggtta tgatgatttc acggaaatga ttgaagagct cgcacgggag gtctcagcag    8040
tatggccaga tttcaagttg ccctcacggg aggaagttga aaacttatac ctaactggga    8100
accgaactga tctgggagag gaaatcaaag agtgtggaga acagtactgc gtgtacgaat    8160
caagtgaggc agcaactgat gctgtcctgg cagcagcaaa tgccggaagt ggcagtgcac    8220
cgagcagtgg aagtacgcag tcaagtctga gtgcaagcac ggcaagcgga tcaggaagct    8280
caccatcagg gtcaggttct ggagcagcgg gtggatcagg ttcaggatca gcacaaacac    8340
aatctagcaa cgtgtcggtc atggcaggcc tcgacacggg agctaagact ggtcaagggt    8400
caggatcaaa aggaacaggt ggttcattcg tttcgaatcc tgtgcgaact ggaggtcgag    8460
caacggatgt gcaagatcag acaccaggcc ttgtgtttcc agcaccaaaa atcacaacaa    8520
aggccatata catgccgaaa accgtacgcg ataagataaa gcctgaaatg ataaataaca    8580 tgattaaaata ccaaccgcgt gcagaactca tcgataatag gtatgccaca actgagcaac    8640
tcaatacctg gatcaaagaa gcatctgaag ggcttgatgt tacagaggat gtgttcatta    8700
acaccttgct tcctggatgg gtttatcact gcataattaa taacgagc cagagaaca    8760 gagcactagg aacttggcgt gttgtgaata atgcaggaaa ggacaatgag cagcaactcg    8820
aatttaagat cgaaccgatg tacaaagctg cgaagccatc acttcgagct attatgcggc    8880
attttggcga gggagctcgg gtgatgatcg aggagagcgt tcgaattggg aaacctatta    8940
taccaagagg ttttgacaaa gccggtgtgc taagcatcaa caatattgtg gcagcgtgtg    9000
attttatcat gcgtgggggca gatgacacac caaacttcgt gcaagtgcaa aacagcgttg    9060
cagtgaacag gctacgcgga atacagaata agctgtttgc acaagcacga ctgagtgcgg    9120
gtactaatga ggacaactca cgtcacgacg cagatgatgt gagggagaac acgcacagtt    9180
tcaatggtgt aaacgcgctt gcgtgagcac agtagaaact acaaatccat gagtaccagg    9240
gtttgagcgg aataacgctg cgtttcgtta acccttcgtt gttactaggt gtgtacttct    9300
ccacgagagg cgtgcattct tggtagccat gtgtgggtta gggcgacgct ac            9352
```

<210> SEQ ID NO 27
<211> LENGTH: 9339
<212> TYPE: DNA
<213> ORGANISM: Wheat streak mosaic virus

<400> SEQUENCE: 27

```
aaattaaacc aacccaaaac aatctgacaa cgaacaacgc acactcacag caaccacaag      60
ctcaagttac gcatcgttca ttgaatagga agcaatttgt tcattgtgag ctctcgcata     120
gagataagca atggcttcag cgaattgttt gctcggtgaa tttggaaagc aggggggtcgt    180 cgctaacgac ccatatgtac ggtgcagggc gcgcacgctg ctattttttaa gcactgagga    240 agaggttgat gtggtggtca accaccacgg accaggaagc attttctggt caaaggatgg    300
agttttaacc caaacgggga aaaacctcta taaagcaaca atgaatggct ggggttacga    360
tctcgcagcc aacgtatttg tttgcggcaa gtgcagatcc agttgcactc actataggta    420
cttcgttgag gatcactacg cctgcgcaa gctcgtggaa aagaattgcg cgtacatcaa    480
gactgacaag tacgtgagag tagtggatgc attcccaatc atgccagcgt atgccacagc    540
```

```
agcgcaagaa gcacgcataa tacaatggat gagtaaaacc agccagtgtc ttgcggacca    600
ctgtgtgcag tataagcgtg aggtcacatt tgtgaacgcc aaaaccaagg aggaagaaac    660
gcgctccaag gacagctgcg cagaagttta ctacgatgaa ttcgatgaag atcacacagt    720
aacagagcac gcacatagga agaacccact acatgagtac aaggagaaac aactaaggat    780
gacctcaagt aacatatctg cactggttga ccaggtcacc aggctcatgt attcacaagg    840
gaaaactatt gaaatcgtcg gaagcaaggg gcacaagaag ttcgccaaga taccattgaa    900
gcacacaatg gggtatccaa agcgagaatg ggatggatgc aaggatgttc ctgaggatat    960
gcgaagcttc ataaccacgt acagcagcgt gatacaatac acacgtaagg ttcaggacca   1020
cgaaattact cttgggtgga gtggtgtagt gttgagcgag tttgatgtcc cagatggata   1080
tcaggaggac tgtgtcgatg ggctcttcat tgttatgggg agatgcgctc atgggcgaat   1140
ccaaaacgca ctaaaaccga gatgcataca tggtttgcgc tggtatgggg attcacctgt   1200
gaatagtgcc attccaaaac aacatgcacac atgcaacaat aattgcgcag gctatttgga   1260
tgctctacca aagaaggtaa gtcgcgtgtg gcaagcaatg ttcgacatcc ataaccttaa   1320
gtgcgatgaa tgtcgagccg aatggaaggc tagaacaggc gctgagcata cgcagatgtt   1380
acgaaagtca atagcgaatt atgttcaaac atacccggac agcgacgtaa cacttttcaa   1440 atcattttg caagcactag gttcggaaga agtaagtgga gtcaagcagt tcaaacctag   1500
tggtacgttg cagttagtgg atgtttggcg aactatgaag agcaccataa atattccaaa   1560
cagaattatt tatatgggta tgttcacgga taattatggg aatttcgatt tctttccaaa   1620
cacttcgatg cccgaactgt tcgcaacgta catgcaacca gtgcatcata ggctacttga   1680
agacgggaca attgacacaa attttcgatt tgttgatgtc gagaggcaaa tacaaacgag   1740
cattgaaagt ttatatcccg tgtttgatag catttattgg aacgagcaag cacgaagagt   1800
ccacaggatt caacctctca cggactgcgc aatggaaatt aatggtgaga ctaaacccat   1860
ctgccactgg gaaggaaacg tcccttttgta taacccgata attcgagcaa caccaggaca   1920
actaccattc gggatgacaa cacatctgct aagtgtaaat gacaggagtg gaagatacca   1980
ctatgtaccg aagaatgggt attgctacat gtacattttt gcatgtgcaa tgatcttctg   2040
cggtaatagc aatcgatcaa ctgttgacgc attcgtgagg caagtatgtg aagatctggg   2100
tccgtggcca acttttggag aggttctgag gcaactcgac tggatggcca cattctacgg   2160
ttgctatgat gcactagtgc cagtaatact cgtagatcac acgaagaaga caatgcacgt   2220
tcctactcca tacggagtca agcagtcagg aatgcacacc attcgggtca atacagttct   2280
cgaactgatc acattggaca caatggcgag cggagcgatg aaagactaca agattggtgg   2340
tttccaggag acagtcttga gtattcatgc gtgcgtcaag agccgaaaag aatttgtgcg   2400
gaaaattaac aaggatgccg aatggctagt ggatatgttt attaacccat ctacactttt   2460
tgtgttaggt gggttgatcg aagtgcacca agtcatacta gcagacgtgg agaactcgtt   2520
tgataaatcg gcagcactat tgaacttgcg ccaaatggca ttgaaactcg gaccacactt   2580
ggaatcaaag caacgagtgc gccaatacat ggagttgatg attcaacacc gagcatcagt   2640
agaggccata atcccatcac aacatatgaa ggccgaaatg atgcaataca ttgatgcact   2700
acaacgatcc attctcgaag agcaggcaat actcgaaatg gatagagttg gaggaaagga   2760
aaaaatgctc atcgagcaag atctttcaca cgcagagtgt gctttcaacg aattcttcaa   2820
ctcaattggt tacttaaact ttcatggaac cgtgctacga ctcacatatt ctggtccagg   2880
aagaaaggtt ggagaaatgc tcgagagttt aaaagacaat tggttaacgc gctatctccg   2940
```

```
aggaccgagt cagccgagag actacaaagg gagttccttg aggatttgga ggaaggttac   3000
tcacctttgc ggaaacgcgt acagatgggt gttttacaac atggccgcga acgtcttgca   3060
agttatactc ataggccttt ctaccgtttt cggagcgtat ttattaaaga agatcttaaa   3120
aatgctgcag tgggagaagg aacaggaaag tgctgaattg gtggagtatc aaggaaaacg   3180
agaagaagca tggataacta ggattatggc tgtactatat atcatagctt cactattctc   3240
agtcgatttt agttccgcac tatactcaaa ccttgtaaaa tttcgcacaa ttttgatat    3300 actgaagttt aactgcgaat atcaaagtgg tatatttgag agcttaaaga accaactcgg   3360
caacattcca gcattccacg aaatgcacct atacgaccac gaggcaacac aagtcgcagt   3420
gccaccagca gtcctcacat ttgaaagatg gttcgagacg cgcataacgt caggtcagca   3480
ggggtatgct ccattggatg gaatcatgt cagtctgaca atgacaaaag acacagtggg    3540
tgacgtagcc acgcaagtgc aggctagcaa ggccaatgaa tttctcatta tcggtcatgt   3600
tgggtgtgga aagtcgacag cttttccagc cactttgtca cggaatggcc gtgtaatgat   3660
ttgcgagccc acgcgcgtgc ttgtaacaaa cttgcaggac tcgatgctag caacaaagaa   3720
cttgagtatt agcgccatga tgagacatca tagagtgatg acagcttcaa acatcacagt   3780
cacaacgtat ggatatgcat ttcactactt gtacaataac tcacacaacc tggcagagta   3840
tgattatatc ctatttgacg aagttcacca aacatcagca gagatgctag tgttctacaa   3900
ctggctcaag agcacgacgt ggagtggcaa actgataaag ctgacagcaa ccaataacac   3960
agtgaacggg gatatgcaaa ctcagcaagc acttgatgtt aaaacttggc cggtcatgga   4020
tcacagaaca ttcatgcagg agcaagggcg gggcacagca catgacgcgt ctgtacttgg   4080
cgacgtggta attgtcttct tgacttcatt ccgtgagatt gacagtcag cagacatcct    4140 aagcaagaat ggtaaaattg tgtcataaa agcagatagc cggcatttga ggaacaaggt    4200
gagcttgatg gacgatgtag aggcattgcg ggccgagaag aagtacattc tagcaactaa   4260
cattctgcaa aatggtgtga atttgcacgc ggatgttgtg gttgacttcg gttttaagat   4320
tgtgcctacc attgatagtg ataatcggat gattacagtc aagcgccaat tgattaacaa   4380
atcagatcgg attcaacggc tgggccgagt tgggcgtatg aagatgggtt atgcacggaa   4440
gattgggaat gacattgacg cctcatttgc attggatgaa gtaacagcaa cagaggctgc   4500
tctactggcg ttcggatttg tgtggcacc  tgttttacaa aatgttgacc aacacacatt   4560
tggtaaaata actgcagaac agataagaac agcagcacga tttgaaatgc agttatcata   4620
catggtatgg atggtgaacc gtgatggaac aatggctacg aggttgtacg agcaattcaa   4680
gcctctgctc ctaacaccag gaaacacgag tttagctcca tattacgaaa cattggtcga   4740
cacacatagg tttcgtagta ttggccagta tgtgtctttg ggctacatgc ggacagatga   4800
gaaacaccat ctgattttac catttcacca taatgacatt agcgttgagt ttgcttgtaa   4860
aattggtgaa gcatatttgg aatcacaagt cccaacgtca atcaaattgc gcgtaccggc   4920
agttaatcac agggaagtcg ccatgaagat gtccgccaat ccggaagatg tgggaaccat   4980
tctttatatg gttgagcaag ctttaattaa cgagaaaacc aagctcgaga atctcacaca   5040
agcattccag caacagcaat caacatattg tagtgttttg attccgaatt tcaatgttgc   5100
tgggagatta actcaggcca tggatcgcat aaggaagaac gtgtcagtcc ttcaacacca   5160
gaagacagca ctggaaaagg ccacggttac gtatgattac acgaagttgg tggagttgct   5220
ggatgagaac ccaagtatag catcacatgt gtcatatcaa gcgggtccag caaagttcat   5280
tgacgaattt attttggaga agcgtgacta tggatggctg ccatatcttg cagttggaac   5340
```

```
agcatgcacc gtggctggaa ctgcgcttgt ggtgatgtac tataggagga tgaagcgaag   5400
cgttaaattc gagggcaagg cagcccgcaa caggaacgca aaacgacaat cagcaaggga   5460
ccagaaaatg gaacgtggca atgagtacac atattatgat gctggtgaca cactgtatga   5520
tggcgtgcaa gaaatatga atcacactcc tgactggaca gatcgaatca aaagaaaac    5580 acaagcacat gcaatgcaat ttgggcggga ggtcccaaaa actgaaagcc aacgttcatc   5640
tcaatattgg cacttttatg gatttgatcc caagatgtat gattctgttg agttcaagga   5700
tattgccgca aacttctcag ttcaccagga cgcaaaggca atggatttgc agaaggcatt   5760
cacagagatg gtcgaaaacc gctgggacga cgaagacttc tttgatgaga agataccaaa   5820
gcgcgtgcta gccatttca ggaaaggga caaggttcgt gaagtcgcac ttgcaccgca    5880
caaaccgaac caggtaaata gcgtggttt gccagtaggg tatgccgacc acagaggtga    5940
atggcgccag acgcaaccat cttttgagaa agaggtgtca tacgagaaca aatcgctatt   6000
cgaaggggcg cgctcactag accatataca tcaaaaccaa gttattttgg ttgaggataa   6060
tcagcaactt aatggtctaa ttgttggcaa catacttttg gcgccgtatc atttcacacg   6120
gaatatgcga aataggagg agaaagaaac tcggatgctc acacaatttg gcacctataa    6180
tcttgggaag ctaacggaaa aacatgtcac caagtttaca atgatggatc tagtggcctt   6240
aacactacca cccacatttc aagccaggcg ccgactcaaa tgcttcaggc ctccaaggga   6300
aggcgaacga gcgatcctag tcaccatgca ctacgataag gcaggatggg ttggaaaaca   6360
atcagctgaa acagctatca caccgtacgg cgatcgacac gatggcttat ggaaacataa   6420
aatcacaacg tcagcagggg attgtggaag cgcaattgtt gctgtagctg atttgaaggt   6480
tgttgggttt cacaacctcg gagggaaggg cgagaattac tttacgccag tcacaagcga   6540
ggtaatggag tttctcgcag agaaggccgt gattccgttg gttccgtgga gttttcaga    6600 tgagcatgtt gatctgtgcg gattaatcgc ggccaatggt gcagataaat tccattctc    6660 aaagcaaatc agcgatttag tcagttggca gagccttcaa atgacaaagt actgcggtga   6720 gaattcaaa gcaattgcat atgcaccaaa ccgcatgtca aagaggcacg tgataacagg    6780
acgaaggcct gaatttgtca gttttggga ttcccaccca aaatggaatg cgctagtgac    6840
tccctatctg aatgaattcc agccatcaat tctgaatcat gaagcatatt ataaggatgt   6900
cctgaagtac aacaaggaca tagtggttgg aggtacggat gaggtgtgct ttgcgaaggc   6960
cgtggttgca actgttgagg ctctcaaggt ggcaggcttt gtgaaaggac agttcaatcc   7020
tgtgtttgat ggatgtaaag tctttaacga tctaaacctt gacgccgcta tgggcgcttt   7080
atacacagga aagaagtccg catactttga tggagcaact agcgatgaaa taaacgaact   7140
ctttgaacat agcgctgcta agttgctcag taatggacat ggagtttggt ctgggttgtt   7200
gaaggcggag ctgagaccga aggcaaaggt ggccgcaaac aagactcgca cattcacatc   7260
agcaccaatt gacattctta tgggtgctaa agccgttgtt gatgaattta ataaattctt   7320
ttacacacgg cacttgcggg ggccttggac cgttggcatc aacaaattta atggcgggtg   7380
gaacctgctt gcagaaaatc tgatggtaca cgaatggttc atagatgctg atgggtccca   7440
gtttgacagt tcaataaccc cacttctgat gaatgcagtc ctgaacatca ggcaatactt   7500
catggtggaa gatgaagaag cggagttgat gctatcaaac ttgtatacgc aaatcatcaa   7560
cacgtgcata ctcatcgaag atggaacgat cgtgcagaaa tttcgaggta ataacagcgg   7620
tcagccgagc acagttgttg acaacacgat gtgtcttatc attgcaatgg agtactgcag   7680
actgcgcgtc gcaaaggagt atggtcatga catgagattc ctatatgtat gcaacgggga   7740
```

```
tgatttgcta attaatgcca acacgcaaga taaggacttt gtgcaacaac actttgccaa    7800
ctacatgcgg gagctggaat tgaattattc attcgacgag gcatatcgga gcattgaaga    7860
agttgagtac atgtcgcaca catttgtcaa gcgaggatca atgttcatac caaagctaaa    7920
gcgagagcgg atcgtggcca ttttggagtg gcaacgaagc aaggagccaa aggccataca    7980
aagcgcaatt atagcagcat atgtcgaagc ttttggatat gatgacttca cagagatgat    8040
tgaagagctg gcgcacgaag tctcacaaat ctggccagat ttcaagctac aacacgaca    8100
ggaagttgag gatttgtact aacaggaaa tcggacggat ttgggagaag aagcgaagga    8160
gtgtgctgag caatactgtg tgtacgagtc aagcacgtca gcaacagaag atgtgttggc    8220
agcggcagat gctgggacta atggtgcttc aagcagtgga aacgcgcaag cagggtcaag    8280
cacaggatca gctagtgggt ctagctctgc agcatcacaa tcacaagcag gtggcacttc    8340
cacaatggca ggtgtggaca cagggagagc taaagttggg caagcttcag gatcaaaggg    8400
cactagcggt tcattcattt cgaatccggt tcgaaatggt ggccgggcca cagacgtgca    8460
ggaccagaca cctggcttgg ttttccccgc gcccaagatc acaacaaaag ctatttatat    8520
gcccaggaat gtgcgcgaga aaataaagcc agagatgatc aataacatga tcaagtacca    8580
accacgggcc gagcttgtcg acaatagata cgccacgatt gagcaactca acacgtggat    8640
caaggaggcc tcgatggtt tggatgtcac agaggatgtg tttgttaaca cactattacc    8700
gggatgggtg taccattgca taatcaatac aaccagtccg gaaaacaaag cactaggaac    8760
ctggcgtgtg gtgaataacg ttgggaagga taacgaagag cagcatgaat acaagattga    8820
tcctatgtac aaagctgcaa accgtcgct gcgcgcaatt atgcgacatt ttggcgaggg    8880
agcaagagtg atgattgagg agagcgtcag gattggaaag cctataatac caagaggttt    8940
cgacaaagca ggtgtgctga gtgtcaacaa tattgttgca gcgtgtgatt ttatcatgcg    9000
cacttcagat gacacaccaa atttcgtgca ggtgcagaat agcgtagcgg tgaataggct    9060
gcgcgggata cagaataaat tatttgcaca ggcacgattg agtgcgggta ctaatgaaga    9120
caactcacgt cacgatgccg atgatgtgag ggagaacacg cacagtttca atggtgtgaa    9180
cgctcttgcg taagcacagc agaaactaca gatccatgag taccagggtt tgggcgaaat    9240
aacgctgcgt ttcgttgacc tttcgttggtt actaggtgtg cacttcttca tgaaaggcgt    9300
gcattcttgg tagctatgtg tgggttaggg caacgctac                           9339

<210> SEQ ID NO 28
<211> LENGTH: 9384
<212> TYPE: DNA
<213> ORGANISM: Wheat streak mosaic virus

<400> SEQUENCE: 28
aaattaaacc aacccaaatc gatctgacaa cgaacaaaac gaactcaaag cacccacaag     60
ctctagttca acaaagttca tcacgcagaa agcaattcgt tcattgtgag ctctcgcata    120
gagataagca atggcaacag cgaattgttt gctcggtgac ttcggaaggc agggggtcgt    180
cgctaacgac ccatatgtac agtgcagagc gcgcacgctg atttttcctaa gcactgagga    240
ggaggttgat gtggtggtta accaccacgg accaggaagc attttctggt caaaagaagg    300
tatcttaaca cagacggcta agaacctttta caaagctact gcgtatggct taggctacga    360
ccttgcagca aacgtcttcg tttgcggcaa gtgtaggtcc agctgcactc agtataggta    420
cttcattgag gatcactttg cttgcgacaa actcgtggaa aagaactgcg cgtacatcaa    480
ggatgataag tacgtgaagg ttgtggaggc attcccaatt atgccatctt atgccacacc    540
```

```
agggcaagaa acacgcatca tacagtggat gaacaagaca agtcaatgcc ttgctgatca    600
ctgcatccaa cgcactcgcg agatcacttt caccaactca aaaactcagg aggaagaaac    660
tcgcgtgaag gattgcagtt tggaagtatt ttatgatgac ttcgatgaag ctcatgctgt    720
gattgagcac gcacatcgga aaaatccggt tcacgaatat aaggagaagc agctgcggat    780
gacttcaaat aatatagctg cgttagtgga ccaagtgaca cggatgatgc actccaaggg    840
caaaacagtg gaaatagttg ggagtaaagg ccataagaaa tttgccaaaa ttccactgaa    900
gcacacaatg ggatatccaa agcgggattg ggacgcaaca aaggacatac cagaagattt    960
cagaggcttt atcacaactt atagtggcgt catacaatac acacgcaaag tgcaggatca    1020
cgaagtgacg cttggatgga gtggtgttct gcttagtgag atggatgttc ctgatggcta    1080
tcaagaagat tgcgttgacg gtctatttat tgtcatggga agatgtgcac atggacgcat    1140
tcaaaatgca ctgaagccga aatgcacaca tggacttaga tggtatggcg accaagcagt    1200
gaacaaagtt attccgaaat atcacgatgt gtgcaacaac aactgcgcaa gttacctgga    1260
agccttgcca agaaaggtta gccgtgtatg gcaatcaatg tttgacatac ataatctgag    1320
gtgcgaccaa tgtagaacag agtggaagat gcgaacagcc tcagagcatt tgcaattgtt    1380
acagaaatcg gtggaacatt acatgcaaac gtatccagac agcgatgtaa cactgttcaa    1440
agcattcttg caagcactag ggccagatga agaggttgag gcacgccagc tcaaacccaa    1500
caatacattg caacttgtag atgtgtggcg aacaatgaaa acacaataa acatcccgaa    1560 tagaatcatc tacatgggca tgttcacgga caattatggg aattttgatt tctttccgaa    1620
cacatcaatg cctgaattat tcgccatgca catgcaaccg gtgcaacata agatgctaga    1680
agatggaaca attgaaacga attttaggtt cgttgatttg gaagggaaaa tccaaactag    1740
cattgaaagt ttgtatccga catttgacag cacatactgg aatgaacaag cacgcagagt    1800
tcacagaatc caaccgctag cagactgctc gatggaaatt aacggcgagt ctaagcccat    1860
ttgtcactgg gaaggaaatg tgcctttgta caatcccatt attcgtgcaa cgcctggaca    1920
attaccgttt ggagttacaa cgcatttgct gagtgtaaat gacaggagtg gaagattcca    1980
ttatgtgccg aagaatgggt attgttacat gtacatattt gcctgtgcga tgattttctg    2040
tggtaatagc aatcgttcca cagttgacgc ctttgttcgg caagtctgcg aggatctggg    2100
tccttggcca atgtttggtg atgtactaag acaacttgac tggatggcga cctttatgg    2160 atgttacgac gcattggtgc cagtcatctt ggtagaccat acaagaaaga ccatgcacgt    2220
gccaacacca tatggtataa agcaatcagg aatgcatacc atcagagtca acacagtgct    2280
agagttgata actctcgata ccatggccag tggagcaatg aaagattaca aaattggcgg    2340
gttccaagag actgttctca gtatacaagc atgcgtcaag agcagaaaag aatttgtgcg    2400
caaaattaac aaggatgcag aatggttggt ggatatgttt attaatcctt caacgctctt    2460
cgtgttggga ggcttaattg aagtgcacca agtcattctt gctgatgtcg aaaattcatt    2520
cgacaaatca gcagctttac taaacttgcg ccaaatagct ttaaagctcg gaccacactt    2580
ggaatcaaag cagcgtgtac gtcagtacat ggagttaatg attcagcatc gggcatcagt    2640
tgaagcaata attccctcgc aacacatgaa agctgagatg atgcaatata ttgatgcact    2700
gcaacgctca attcttgagg agcaagtaat catagagatg gatcgagttg gaggaaagga    2760
aaaaatgctc gtcgagcaag atcttcaca cgcagagtgt gcgtacaacg agttcttcaa    2820
ctccattggc tacttaaact ttcatggaac cgttttacga ctcacatatt ctggtccagg    2880
aagaaaggtt ggagaagtgc tagagagttt aagagacaac tggttgacac gctatctccg    2940
```

```
aggaccgaag cagccgagag actacaaagg gagttccttg aggatttgga ggaaggttac    3000
tcacctttgc ggaaacgctt acaggtgggt attttacaac atggccgcga acgtcttgca    3060
agttatactc ataggccttt ctaccgtttt cggagcatat ttattaaaga agatcttaaa    3120
aatgctgcag tgggagaagg agcaagaaag cacagaattg gttgaatacc aagggaagcg    3180
agaggaagca tggataacac gagtaatggc tgtattgtat ataatagctt cacttttctc    3240
cgtagatttt agttctgctt tatattcgaa tttggtgaag ttcagaacca tatttgacat    3300
cttgaagttt aattgcgaat atcagagtgg aatttttgaa agtctgaaaa atcaactcgg    3360
caacatccca gcgtttcatg aggtacattt gtatgaccat gaggcaacac aagtagcagt    3420
tccaccagcg atattgacat tcgagcgatg gttcgagact cggatcacat ctggccagca    3480
aggatatgca ccacttgatg gtagccacgt gagcttaacg atgacaaaag acacagttgg    3540
tgagatcgca acacaagtgc aaacgcacaa ggcaaaggag tttcttatta taggacatgt    3600
tggatgtggg aaatctacag cttttccagc aacactctcc cggaatgggc gtgtgatgat    3660
atgcgaacca acccgcgtgc tagtcacaaa tttgcaggat tcaatgctag caacgagaaa    3720
tctaagcatc agtgccatga tgagaaacca ccgggttatg acggcgtcga atataacagt    3780
aactacgtat gggtatgcac tccactactt gtacaacaac tcacataacc tttcagaata    3840
tgattatatt cttttttgacg aagtgcacca aacctcggca gagatgttag tgttttacaa    3900
ctggcttaag agcacaacgt gggagggcaa gctcatcaag ttaacagcca cgaacaacac    3960
agttaatggc gacatgcaaa cacagcaagc cctcgatgtc aaaacgtggc cggttatgga    4020
tcacagaaca ttcatgcagg agcaaggtcg aggaacggct cacgatgcat caactcttgg    4080
tgatgtcatc atagtcttct taacttcgtt tcgtgaaatt gatgaatctg ctgatatttt    4140
aagcaaaaat tcaaagattg gcgtaataaa ggcagatagt cggcacttgc gaaacaaaat    4200
tagcttgatg gatgatgtcg aagcactccg agctgagaag aaatacattc ttgcaactaa    4260
tattcttcaa aacggtgtga atttgcatgc agacgttgtc gttgattttg gcttcaagat    4320
tgtaccagcc attgacagcg acaatcggat gatcacagtc aagcgccaat tgatcaacaa    4380
atcagacagg attcagagac taggacgagt aggccggatg aagatgggat acgcaaggaa    4440
aatcggaaat gaaatagatg cctcattcgc tttggatgaa gtcacagcta cggaagctgc    4500
cttgttggca tttggactcg gtgttgctcc agtgttgcag aatgtcgatc aacacacatt    4560
cggaaaaata acagcagagc aagttcgaac agctgcgcgc tttgaaatgc aattgtcgta    4620
tatggtgtgg atgattaaca gagatggcac tatggccaca cggttatatg aacaattcaa    4680
atcattgctt ttaacaccag ggaacacgag tttggctccg tattacgaga cactcgttga    4740
cactcacaga ttcagaacta ttggacaata cgcaactctt ggatacatgc gcacagacga    4800
aaagcaccat ttggtattac catttcatca taatgacgtg agcgttgaat ttgccgaaag    4860
gattggcgaa gcctatatgg cctctcaagt cccgacatca atcaagttgc gcgtacctgc    4920
tgtaaatcat agagaagtgg cgatgaagat gtcagcaaat cctgaagatg tgggaaccat    4980
attgtatatg gttgagcaag cgctaataag tgaaaagacg aaactggaga atttaaccca    5040
ggcattccag cagcaacaat caacatattg cagcgtgctc atccctaatt ttaatgttgc    5100
tggtcggcta acacaggcaa tggatcgcat aagaaagaat gtttctgtgc tgcaacacca    5160
gaaaacagct ctcgaaaagg cggcagtgac ttacgactac acgaagttag ttgagctcct    5220
tgatgaaaat ccaagcatag cttcccatgt gtcataccag gctgggccag caaaattcat    5280
tgatgaattc atattggaga agcgcgatta tgggtggcta ccatatcttg cagtaggaac    5340
```

```
tgcgtgtgca attgctggca caacacttgt aatgatgtac taccgtcgca tgaagcgtag    5400
tgtcaagttc gagggcaaag cagcacgcaa caggagtgca aaacgacaat cagcaagaga    5460
ccaaaagatg gagcgtggta acgaatacac atactacgat gctggtgaca ccttgtataa    5520
tggagttcaa gagaatatga atcatgcacc agactggacc gatcggatta agaagaagac    5580
tcatgcatac gctatgcaat ttggtaggga agtaccaaag actgaaacac agcgatcctc    5640
acaatactgg cacttctacg gttttgatcc aaagatgtat gactcagtcg aattcaagga    5700
catagcagca aacttctcag tgcaccagga tgcaaaggca atggatttgc agaaagcctt    5760
cacagaaatg gtggaaaatc gttgggatga tgaagacttc ttcgacgaga agataccaaa    5820
gcgagttttg gccatcttca ggaaaggaga caaggttcgt gaagttgcat tggcacctca    5880
caagccaaac caagtcaaca agcgtgggct acctgtcgga catgctgatc acagaggaga    5940
gtggagacaa acacagcctt catttgaaaa agaagtgtcg tacgagaaca atcaactttt    6000
cgaaggtgca cgttcacttg atcatatcca tcagaatcaa gtcatcctcg ttgaagacaa    6060
tcagcagtta aatgggctaa tagttgggaa catactcttg gcgccatatc atttcacacg    6120
aggtatgagg aacagagagg agaaggagac acgcatgttg acacagtttg gaacgtacaa    6180
tcttggaaaa cttaccaaca agcatgtcac aaaatttaca atgatggatc tggtagcatt    6240
aaccttgcct ccaacatttc aagcaagacg gaaactcaaa tgtttcagac caccaaggga    6300
aggagagcga gcaatgttgg tgaccatgca gtacgagaaa gcaggatggg ttgccaagca    6360
atcagcagaa acaacaatca caccattcgg tgatcgacat gatggtttgt ggaagcatag    6420
aatttcaaca ggaccaggtg actgtggaag cgccatagta gcagtagcag acctaaaagt    6480
tgtgggattc cataaccttg gagggaaagg tgagaattat tcacaccgta actattga    6540
ggtcatggat ttcttagctg aaaagtctgt gacaccgctt gtgccatgga agttctcaga    6600
cgagcaagtt gacttatgtg gtttaattgc ggccaatgga gcagacaaat acccattcac    6660
caaaacaata agcgacttgg ttagttggca aagtctccaa atgacgaaat actgtgggga    6720
gaacttcaag gctatcgctt atgctccaaa ccgaatgtcg aaaaggcatg tcataacagg    6780
aaagaggcct gaattcatta aatttctaga ttccccacccg aagtggaatg caacggtaac    6840
accttttctta aacgggtttc aaccatcagt ttttgacacat gaagcatatt acaaggatgt    6900
gttgaagtat aacaaagaca taattgttgg agggactgat gaagtgtgtt ttgcgaaggc    6960
agtggtcgca accattggga ttctagaaat agccggattt tcaaagggac aatttcaacc    7020
aatctttgac ggatgtaaaa ttttcaatga cttgaatttg gatgccgcaa tgggagcttt    7080
gtactcaggg aagaaatcag catactttga cggagcaaca agcgacgaga tcaatgaatt    7140
ctttgaactg agtgcagcga agctactcag taacggacat ggagtatggt ctggtttact    7200
caaagctgag ttgagaccga aggcaaaggt cgtggcgaac aaaacgcgaa cattcacatc    7260
agcaccaatt gatatactca tggggtgccaa agctgtggtt gatgagttca acaaattctt    7320
ctacacaaag catttgcgcg gaccatggac tgtcggaatc aataagttca cggaggttg    7380
ggatttgttg gccaaaaatt taatggtgca cgagtggttc attgacgctg atggttcgca    7440
attcgacagt tcaatcactc cacttctcat gaatgcaatt cttaacatac ggcaatactt    7500
catggcagaa gatgatgaag ctgaacaaat gctggcaaat ttgtatacgc agattataaa    7560
cacatgcatt ttaattgaag atggaacgat tgtgcagaag tttcgaggta ataacagtgg    7620
ccaaccaagc acagttgttg acaacacgat gtgtttaatc atagcaatgg agtattgcag    7680
aatgcgcgtc gaaaaggatc atgaacatag aatgaggata ctgtacgtgt gcaacggaga    7740
```

```
tgatttgctt attaatgccg acacaaagga caaagacttc atacagcagt attttgccga    7800
ttacatgcgc gaactggagc tgaattactc atttgacgag gcttaccgta gtatcgagga    7860
ggtggaatac atgtcacata catttatgaa gcgaaattcg atgtacattc caaagttgaa    7920
acgcgaacgt attgtggcaa ttctggagtg gcagaggagc aaggaaccga aggctattca    7980
gagcgctatt attgcagcat acgtggaagc tttcggttat gatgaattca cggagatgat    8040
tgaagaactt gcgcaggaag tttcagcggt gtggccggat ttcaagttgc cctcacgaca    8100
agaggttgag gatttgtact tgactgggac ccgaacggat ttaggagaag agattaagga    8160
atgtggagag caatactgcg tgtacgaatc gagtgaggcc gcaaccgacg ctgtcttggc    8220
ggcagcaaat gcaggaactg gtagtgcatc gagtagtgga agcactcagt caagtcagag    8280
cgcaagtact gctagcggat cagggagttc accatcagga tcaggttctg gagcagcggg    8340
tggatcaggt tctggatcag cacaaacaca atctaataac gtatctgtca tggctggcct    8400
cgacacggga ggagctaaga cagatcaagg atcaggatca aaagggacgg gtggttcatt    8460
cacatcgaat cccgtgcgaa ctggaggccg agcaacggat gtgcaagatc agacaccagg    8520
tttagtgttt ccagcaccaa agatcacaac aaaggccata tacatgccaa aaactgtacg    8580
cgacaagata aaacctgaaa tgataaataa catgatcaaa taccaaccgc gtgctgaact    8640
tatcgacaac agatatgcca caactgaaca actcaacacc tggataaaag aggcatctga    8700
agggcttgac gtgacagagg atgttttcat aaacacctta cttccaggat gggtctacca    8760
ctgcataatc aacacaacga gcccagaaaa cagagcacta ggaacttggc gtgttgtgaa    8820
caatgcaggc aaggacaatg agcagcaact cgagtttaag attgaaccga tgtacaaagc    8880
tgcgaagcca tcacttcgag ccattatgcg ccactttggt gagggagctc gagtgatgat    8940
cgaggagagt gttcgaattg gaaaacctat cataccaagg ggcttcgaca aggccggtgt    9000
gctaagcatc aacaatattg tggcagcgtg tgatttcatc atgcgcggtg cagatgacac    9060
accaaatttt gtgcaagtgc agaacagcgt tgcagtaaac aggctacgcg gaatacagaa    9120
caagctgttt gcacaggcac gactgagtgc gggtactaat gaggacaact cacgtcatga    9180
tgcagatgat gtgagggaga acacgcacag tttcaatggt gtaaacgctc ttgcgtgagc    9240
acagtagaaa ctacaaatcc acgagtacca ggatttgagc gaaataacgc tgcgtttcgt    9300
taacccttcg ttgttactag gtgtgtactt ctccacgaga ggcgtgcatt cttggtagct    9360
atgtgtgggt tagggcgacg ctac                                           9384
```

<210> SEQ ID NO 29
<211> LENGTH: 9384
<212> TYPE: DNA
<213> ORGANISM: Wheat streak mosaic virus

<400> SEQUENCE: 29

```
aaattaaacc aacccaaatc gatctgacaa cgaacaaaac gaactcaaag cactcacaag     60
ctcaagttca acaaagttca tcacgcagaa agcaattcgt tcattgtgag ctctcgcata    120
gagataagca atggcaacag cgaattgttt gctcggtgac ttcggaaggc aggggtcgt     180 cgctaacgac ccatacgtac agtgcagagc gcgcacgctg attttcctaa gcactgagga    240
ggaggttgat gtggtggtta accaccacgg accaggaagc attttctggt caaagaagg     300 tatcttaaca cagacggcta agaacccttta caaagctact gcgtatggcc taggctacga    360
ccttgcagca aacgtcttcg tttgcggcaa gtgtaggtcc agctgcactc agtataagta    420
cttcatcgag gatcactttg cctgcgacaa actcgtggag aagaactgcg cgtacatcaa    480
```

```
ggatgataag tacgtgaagg ttgtggaggc attcccaatt atgccatctt atgccacacc    540
agggcaagaa acacgcatca tacagtggat gaataagaca agtcaatgcc ttgctgatca    600
ctgcatccaa cgcactcgcg aaatcacttt caccaactca aaaactcagg aggaagaaac    660
tcgcgtgaag gattgcagtt tggaagtatt ttatgatgac ttcgatgaag ctcatgcagt    720
gattgagcac gcacatcgga agaatccggt tcacgaatat aaggagaagc agctacggat    780
gacttcaaat aacatagctg cgttagtgga ccaagtgaca cggatgatgc actccaaggg    840
caaaacagtg gaaatagttg ggagtaaagg ccataagaaa tttgccaaaa ttccactgaa    900
gcacacaatg ggatatccaa agcgggattg ggacgcaaca aaggacatac cagaagattt    960
cagaggcttt atcacaactt atagtggcgt catacaatac acgcgcaaag tgcaggatca   1020
cgaagtgacg cttggatgga gtggtgttct tctcagtgag atggatgttc ctgatggcta   1080
tcaagaagat tgcgttgacg gtctatttat tgtcatggga agatgcgcac atggacgcat   1140
ccaaaatgca ctgaaaccaa aatgcacaca tggatttaga tggtatggcg accaagcagt   1200
gaacaaagtc attccgaaat atcacgatgt gtgcaacaac aactgcgcaa gttacctgga   1260
agccttgcca agaaaggtta gccgcgtatg gcaatcaatg tttgacatac ataatctgag   1320
gtgcgaccaa tgtagaacag agtggaagat gcggacagcc tcagagcatt tgcaattgtt   1380
acagaaatct gtggaacatt acatgcaaac gtatccagac agcgatgtaa cactgttcaa   1440
agcattcttg caagcactag ggccagatga agaggttgag gcacgccagc tcaaacccaa   1500
caatacattg caacttgtag atgtgtggcg aacaatgaaa acacaataa catcccgaa   1560 tagaatcatc tacatgggca tgttcacgga caattatgga aattttgatt tctttccgaa   1620
cacatcaatg cctgaattat tcgccatgca catgcaaccg gtgcaacata agatgctaga   1680
agatggaaca attgaaacga attttaggtt cgttgatttg gaagggaaaa tccaaactag   1740
cattgaaagt ttgtatccaa catttgacag cacatactgg aatgaacagg cacgcagagt   1800
tcacagaatc caaccgctag cagactgctc gatggaaatt aacggcgagt ctaagcccat   1860
ttgtcactgg gaaggaaatg tgcctttgta caatcccatt attcgtgcaa cgcctggaca   1920
attgccgttt ggagttacaa cgcacttgct gagtgtaaat gacaggagtg aagattcca   1980 ttatgtgccg aagaatgggt attgttacat gtacatattt gcctgtgcga tgatttctg   2040 tagtaatagc aatcgttcca cagttgatgc cttcgttcgg caggtctgcg aggatctggg   2100
tccttggcca acatttggtg atgtgctaag acaacttgcc tggatggcga ccttttacgg   2160
atgttatgat gcattggtgc cagtaatctt ggtagaccac acaagaaaga ccatgcacgt   2220
gccaacaccg tacggtataa agcaatcagg aatgcatacc atcagagtca acacagtgct   2280
agagttgata actctcgata ccatggccag tggagcaatg aaagaataca aataggcgg   2340 gtttcaagag acagttctta gcatacaagc atgcgtcaag agcagaaaag aatttgtgcg   2400
caaaatcaac aaggatgcag aatggttggt ggacatgttt attaatcctt caacgctctt   2460
cgtgttagga ggcttaattg aagtgcacca agtcattctt gctgatgtcg aaaattcatt   2520
cgacaaatca gcagctttac taaacttgcg ccaaatagct ttaaagctcg accacatct   2580 ggaatcaaag cagcgcgtac gtcagtacat ggagttaatg attcagcatc gagcatcagt   2640
tgaagcaata atcccatcgc aacacatgaa agctgagatg atgcaataca ttgatgcact   2700
gcaacgctca attcttgagg agcaagtaat catagagatg gatcgagttg gaggaaagga   2760
aaaaatgctc gtcgagcaag atcttcaca cgcagagtgt gcgtacaacg agttcttcaa   2820
ctccattggc tatttaaact ttcatggaac cgttttacga ctcacatatt ctggtccagg   2880
```

```
aagaaaggtt ggagaagtgc tagagagttt aagagacaac tggttgacac gctatctccg    2940
aggaccgaag cagccgagag actacaaagg gagttccttg aggatttgga ggaaggttac    3000
tcacctttgc ggaaacgctt acaggtgggt attttacaac atggccgcga acgtcttgca    3060
agttatactc ataggccttt ctaccgtttt cggagcatat ttattaaaga agatcttaaa    3120
aatgctgcag tggagaagg agcaagaaag caccgaattg gttgaatacc aagggaagcg     3180
agaggaagca tggataacac gagtgatggc tgtattgtat ataatagctt cacttttctc    3240
cgtagatttt agttctgctt tatattcgaa tttggtgaag ttcagaacca tatttgacat    3300
tttgaagttt aattgcgagt atcagagtgg aattttgaa agtttgaaaa atcaactcgg     3360
caacatccct gcgtttcatg aggtacattt gtatgaccat gaggcaacac aagtagcagt    3420
cccaccagct atattgacat tcgagcgatg gttcgaaact cggatcacat ctggccagca    3480
aggatatgca ccacttgatg gtagccacgt gagcttaacg atgacaaaag acacagttgg    3540
tgaaatttca acacaagtac aaacgcacaa ggcaaaggaa tttctcatta taggacatgt    3600
tggatgtgga aaatctacag cttttccagc aacactttcc cggaatgggc gtgtgatgat    3660
atgcgaacca acccgcgtgc tagttacaaa tttgcaggat tcaatgctag caacgagaaa    3720
tctaagtatc agtgccatga tgcgaaacca ccgggttatg acagcgtcga atataacagt    3780
aactacgtat gggtatgcac ttcactactt gtacaacaac tcataacc tttcagagta      3840 tgattatatt cttttgacg aagtgcacca aacctcggca gagatgctag tgttttacaa     3900
ctggcttaag agcacaacgt gggagggcaa gctcatcaag ttaacagcca cgaacaacac    3960
agttaatggc gacatgcaaa cacagcaagc ccttgatgtc aaaacgtggc cggttatgga    4020
tcacagaaca tttatgcagg agcaaggtcg aggaacggct cacgatgcat caactcttgg    4080
tgatgtcatc atagtcttct taacttcgtt tcgtgaaatt gatgaatctg ctgatatttt    4140
aagcaaaaat tcaaagattg gcgtaataaa ggcagatagt cggcacttgc gaaacaaagt    4200
tagcttgatg gatgatgttg aagcactccg agctgagaag aaatacattc ttgcaactaa    4260
tattcttcaa aacggtgtga atttgcatgc agacgttgtc gttgattttg gcttcaagat    4320
tgtaccagcc attgacagcg acaatcggat gatcacagtc aagcgccaat tgatcaacaa    4380
atcagacagg attcagagac taggacgagt gggccggatg aagatgggat acgcaaggaa    4440
aatcggaaat gaaatagatg cttcattcgc tttggatgaa gtcacagcta cggaagctgc    4500
cttgttggca tttggactcg gtgttgctcc agtgttgcag aatgttgatc aacacacatt    4560
cggaaaaata acagcagagc aagttcgaac agctgcacgc tttgaaatgc aattgtcgta    4620
tatggtgtgg atggtcaaca gagatggcac tatggccaca cggttatatg aacaattcaa    4680
gtcattgctt ttaacaccag gaaacacgag tttggctccg tactatgaaa cactcgttga    4740
cactcacaga ttcagaacca ttggacaata cgcaactctt ggatacatgc gcacagacga    4800
aaagcaccat ttggtattac cgtttcacca taatgacgtg agtgttgaat ttgccgaaag    4860
gattggcgaa gcctatatgg cctctcaagt cccaacatca atcaagttgc gcgtacctgc    4920
tgtaaatcat agagaagtgg cgatgaagat gtcagcaaat cctgaagatg tgggaaccat    4980
attgtatatg gttgagcaag cgctaataag tgaaaagacg aaactggaga atctaaccca    5040
ggcattccag cagcaacaat caacatattg cagcgtgctc atccctaatt ttaatgttgc    5100
tggtcggcta acacaggcaa tggatcgcat aagaaagaat gtttctgtgc tgcaacacca    5160
gaaaacagct ctcgaaaagg cagcagtgac ttacgactac acgaagttag ttgagctcct    5220
tgacgaaaat ccaagcatag cttcccatgt ttcatatcag gctgggccag caaaattcat    5280
```

```
tgatgaattc atattggaga agcgcgatta tgggtggcta ccatatcttg cagtaggaac   5340
tgcgtgtgca attgctggca caacacttgt aatgatgtac taccgtcgca tgaagcgtag   5400
tgtcaagttt gagggcaaag cagcacgcaa caggagtgca aaacgacaat cagccagaga   5460
ccaaaagatg gagcgtggca acgaatacac gtactacgat gctggtgaca ccctgtataa   5520
tggagttcaa gagaatatga atcatgcacc agactggacc gatcggatta agaagaagac   5580
tcatgcatac gctatgcaat tggtaggga agtaccaaag actgaaacac agcgatcttc   5640
gcaatactgg cacttctacg gttttgatcc aaagatgtat gactcagtcg aattcaagga   5700
catagcagca aacttttcag tgcaccagga tgcaaaggca atggatttgc agaaagcttt   5760
cacagaaatg gtggaaaatc gttgggatga tgaagacttc ttcgacgaga agataccaaa   5820
gcgagttttg gccatcttca ggaaaggaga caaggttcgt gaggttgcat ggcacctca   5880 caagccaaac caagtcaaca agcgcgggct acctgtcgga catgctgatc acagaggaga   5940
gtggagacaa acacagcctt catttgaaaa agaagtgtcg tacgagaaca aatcaacttt   6000
cgaaggtgca cgttcacttg atcatatcca tcagaatcaa gtcatcctcg ttgaagacaa   6060
tcagcaatta aatgggctaa tagttgggaa catactcttg gcgccatatc atttcacacg   6120
aggtatgagg aacagagagg aaaaggagac acgcatgctg acacagtttg aacgtacaa   6180 tcttggaaaa cttaccaaca agcatgtcac aaaatttaca atgatggatc tggtagcatt   6240
aaccttgcct ccaacatttc aagcaagacg gaaactcaag tgtttcagac caccaaggga   6300
aggagagcga gcaatgttgg tgaccatgca gtacagaaaa gcaggatggg ttgccaagca   6360
atcagcggaa acaacaatca caccattcgg tgatcgacat gatggtttgt ggaagcatag   6420
aatttcaaca ggaccaggtg actgtggaag cgccatagta gcagtagcag acctaaaagt   6480
tgttggattc cataaccttg agggaaagg tgagaattac ttcacaccga taactattga   6540
ggtcatggat ttcttagctg aaaagtctgt gacaccgctt gtgccatgga gttctcaga   6600 cgagcaagtt gacttatgtg gtttaattgc ggccaacgga gcagacaaat acccattcac   6660
caaaacaata agcgacttgg ttagttggca aagtctccaa atgacgaaat actgtgggga   6720
gaacttcaag gccatcgctt atgctccaaa ccgaatgtcg aaaaggcatg tcataacagg   6780
aaagaggcct gaattcatta aatttctaga ttcccacccg aagtggaatg caatggtaac   6840 accttttctta aacggatttc aaccatcagt tctgacacat gaagcatatt acaaggatgt   6900
gttgaagtat aacaaagaca taattgttgg agggactgat gaagtgtgtt ttgcgaaggc   6960
agtggtcgca actattggga ttctagaaat agccggattt tcaaagggac aatttcaacc   7020
aatctatgat ggatgcaaaa ttttcaacga cttgaatttg gatgccgcaa tgggagcttt   7080
gtactcaggg aagaaatcag catactttga cggagcaaca agcgacgaaa tcaatgaatt   7140
ctttgaactg agtgcagcga agctactcag taatggacat ggagtatggt ctggttttact   7200 caaagctgag ttgagaccga aggcaaaggt cgtggcgaac aaaacgcgaa cattcacatc   7260
agcaccaatt gatatactca tgggtgccaa agctgtggtt gatgagttca acaaattctt   7320
ctacacaaag catttgcgcg gaccatggac tgtcggaatc aataagttca acggaggttg   7380
ggatttgttg gccaaaaatc taatggtgca cgagtggttc attgacgctg atggttctca   7440
attcgacagt tcaatcactc cacttcttat gaatgcaatt cttaacatac ggcaatactt   7500
catggcagaa gatgatgaag ctgaacaaat gctggcaaac ttgtatacgc agattataaa   7560
cacatgcatt ttaattgaag atggaacgat tgtgcagaag tttcgaggta ataacagtgg   7620
ccaaccaagc acagttgttg ataacacgat gtgtttaatc atagcaatgg agtattgcag   7680
```

```
aatgcgcgtt gaaaaggacc atgaacacag aatgaggata ctgtacgtgt gcaacggaga   7740
tgatttgctt atcaatgccg acacaaagga caaagacttc atacagcagt attttgccga   7800
ttacatgcgc gaactggagc tgaattactc atttgacgag gcttaccgta gtatcgagga   7860
ggtggaatac atgtcacata catttatgaa gcgaaattcg atgtacattc caaagttgaa   7920
acgcgaacgt attgtggcaa ttctggagtg cagaggagc aaggaaccga aggctattca    7980
gagcgctatt attgcagcat acgtggaagc tttcggttat gatgaattca cggagatgat   8040
tgaagaactt gcgcaggaag tttcagcggt gtggccggat ttcaagttgc cctcacgaca   8100
agaggttgag gatttgtact tgactgggac ccggacggat ttaggagaag agattaagga   8160
atgtggagag caatactgcg tgtacgagtc gagtgaggcc gcaaccgacg ctgtcttggc   8220
ggcagcaaat gcaggaactg gtagtgcatc gagtagtgga agcactcaat caagtcagag   8280
cgcgagtact gctagcggat cagggagttc accatcagga tcaggttctg gagcagcggg   8340
tggatcaggt tctggatcag cacaaacaca atctaataac gtatctgtca tggctggcct   8400
cgacacggga ggagctaaga caggtcaagg atcaggatca aaagggacgg gtggttcatt   8460
cacatcgaat cccgtgcgaa ctggaggccg agcaacggat gtgcaagatc agacaccagg   8520
tttagtgttt ccagcaccaa agatcacaac aaaggccata tacatgccaa aaactgtacg   8580
cgacaagata aaacctgaaa tgataaataa catgatcaaa taccaaccgc gtgcggaact   8640
tatcgacaac agatatgcca caactgaaca actcaacacc tggataagag aggcatctga   8700
agggcttgac gtgacagagg atgttttcat aaacaccta cttccaggat gggtctacca    8760
ctgcataatc aacacaacga gcccagagaa cagagcacta ggaacttggc gcgttgtgaa   8820
caatgcaggc aaggacaatg agcagcaact cgagtttaaa attgaaccga tgtacaaagc   8880
tgcgaagcca tcacttcgag caattatgcg ccactttggc gaaggagctc gagtgatgat   8940
tgaggagagt gttcgaattg gaaaacctat cataccaagg ggcttcgaca aggccggtgt   9000
gctaagcatc aacaatattg tggcagcgtg tgatttcatc atgcgcggtg cagatgacac   9060
accaaatttt gtgcaagtgc aaaacagcgt tgcagtaaac aggctacgcg gaatacagaa   9120
caagctgttt gcacaggcac gactgagtgc gggtactaat gaggacaact cacgtcatga   9180
tgcagatgat gtgagggaga acacgcacag tttcaatggt gtaaacgctc ttgcgtgagc   9240
acagtagaaa ctacaaatcc acgagtacca ggatttgagc gaaataacgc tgcgtttcgt   9300
taacccttcg ttgttactag gtgtgtactt ctccacgaga ggcgtgcatt cttggtagct   9360
atgtgtgggt tagggcgacg ctac                                          9384
```

<210> SEQ ID NO 30
<211> LENGTH: 9385
<212> TYPE: DNA
<213> ORGANISM: Artificial
<220> FEATURE:
<223> OTHER INFORMATION: Consensus Sequence of SEQ ID NOs:1, and 26-29
<220> FEATURE:
<221> NAME/KEY: misc_feature
<222> LOCATION: (680)..(680)
<223> OTHER INFORMATION: n is a, t, g, or c.
<220> FEATURE:
<221> NAME/KEY: misc_feature
<222> LOCATION: (688)..(688)
<223> OTHER INFORMATION: n is a, t, g, or c.
<220> FEATURE:
<221> NAME/KEY: misc_feature
<222> LOCATION: (1051)..(1051)
<223> OTHER INFORMATION: n is a, t, g, or c.
<220> FEATURE:
<221> NAME/KEY: misc_feature

```
<222> LOCATION: (1210)..(1210)
<223> OTHER INFORMATION: n is a, t, g, or c.
<220> FEATURE:
<221> NAME/KEY: misc_feature
<222> LOCATION: (1473)..(1473)
<223> OTHER INFORMATION: n is a, t, g, or c.
<220> FEATURE:
<221> NAME/KEY: misc_feature
<222> LOCATION: (2087)..(2087)
<223> OTHER INFORMATION: n is a, t, g, or c.
<220> FEATURE:
<221> NAME/KEY: misc_feature
<222> LOCATION: (2126)..(2126)
<223> OTHER INFORMATION: n is a, t, g, or c.
<220> FEATURE:
<221> NAME/KEY: misc_feature
<222> LOCATION: (2360)..(2360)
<223> OTHER INFORMATION: n is a, t, g, or c.
<220> FEATURE:
<221> NAME/KEY: misc_feature
<222> LOCATION: (3302)..(3302)
<223> OTHER INFORMATION: n is a, t, g, or c.
<220> FEATURE:
<221> NAME/KEY: misc_feature
<222> LOCATION: (3422)..(3422)
<223> OTHER INFORMATION: n is a, t, g, or c.
<220> FEATURE:
<221> NAME/KEY: misc_feature
<222> LOCATION: (3431)..(3431)
<223> OTHER INFORMATION: n is a, t, g, or c.
<220> FEATURE:
<221> NAME/KEY: misc_feature
<222> LOCATION: (3545)..(3545)
<223> OTHER INFORMATION: n is a, t, g, or c.
<220> FEATURE:
<221> NAME/KEY: misc_feature
<222> LOCATION: (3686)..(3686)
<223> OTHER INFORMATION: n is a, t, g, or c.
<220> FEATURE:
<221> NAME/KEY: misc_feature
<222> LOCATION: (4412)..(4412)
<223> OTHER INFORMATION: n is a, t, g, or c.
<220> FEATURE:
<221> NAME/KEY: misc_feature
<222> LOCATION: (4463)..(4463)
<223> OTHER INFORMATION: n is a, t, g, or c.
<220> FEATURE:
<221> NAME/KEY: misc_feature
<222> LOCATION: (4637)..(4637)
<223> OTHER INFORMATION: n is a, t, g, or c.
<220> FEATURE:
<221> NAME/KEY: misc_feature
<222> LOCATION: (4856)..(4856)
<223> OTHER INFORMATION: n is a, t, g, or c.
<220> FEATURE:
<221> NAME/KEY: misc_feature
<222> LOCATION: (4922)..(4922)
<223> OTHER INFORMATION: n is a, t, g, or c.
<220> FEATURE:
<221> NAME/KEY: misc_feature
<222> LOCATION: (4925)..(4925)
<223> OTHER INFORMATION: n is a, t, g, or c.
<220> FEATURE:
<221> NAME/KEY: misc_feature
<222> LOCATION: (5039)..(5039)
<223> OTHER INFORMATION: n is a, t, g, or c.
<220> FEATURE:
<221> NAME/KEY: misc_feature
<222> LOCATION: (5153)..(5153)
<223> OTHER INFORMATION: n is a, t, g, or c.
<220> FEATURE:
<221> NAME/KEY: misc_feature
<222> LOCATION: (5183)..(5183)
<223> OTHER INFORMATION: n is a, t, g, or c.
<220> FEATURE:
<221> NAME/KEY: misc_feature
<222> LOCATION: (5639)..(5639)
<223> OTHER INFORMATION: n is a, t, g, or c.
<220> FEATURE:
<221> NAME/KEY: misc_feature
```

```
<222> LOCATION: (5642)..(5642)
<223> OTHER INFORMATION: n is a, t, g, or c.
<220> FEATURE:
<221> NAME/KEY: misc_feature
<222> LOCATION: (6089)..(6089)
<223> OTHER INFORMATION: n is a, t, g, or c.
<220> FEATURE:
<221> NAME/KEY: misc_feature
<222> LOCATION: (6834)..(6834)
<223> OTHER INFORMATION: n is a, t, g, or c.
<220> FEATURE:
<221> NAME/KEY: misc_feature
<222> LOCATION: (7100)..(7100)
<223> OTHER INFORMATION: n is a, t, g, or c.
<220> FEATURE:
<221> NAME/KEY: misc_feature
<222> LOCATION: (7352)..(7352)
<223> OTHER INFORMATION: n is a, t, g, or c.
<220> FEATURE:
<221> NAME/KEY: misc_feature
<222> LOCATION: (7691)..(7691)
<223> OTHER INFORMATION: n is a, t, g, or c.
<220> FEATURE:
<221> NAME/KEY: misc_feature
<222> LOCATION: (7931)..(7931)
<223> OTHER INFORMATION: n is a, t, g, or c.
<220> FEATURE:
<221> NAME/KEY: misc_feature
<222> LOCATION: (8264)..(8264)
<223> OTHER INFORMATION: n is a, t, g, or c.
<220> FEATURE:
<221> NAME/KEY: misc_feature
<222> LOCATION: (8270)..(8270)
<223> OTHER INFORMATION: n is a, t, g, or c.
<220> FEATURE:
<221> NAME/KEY: misc_feature
<222> LOCATION: (8278)..(8278)
<223> OTHER INFORMATION: n is a, t, g, or c.
<220> FEATURE:
<221> NAME/KEY: misc_feature
<222> LOCATION: (8309)..(8309)
<223> OTHER INFORMATION: n is a, t, g, or c.
<220> FEATURE:
<221> NAME/KEY: misc_feature
<222> LOCATION: (8522)..(8522)
<223> OTHER INFORMATION: n is a, t, g, or c.
<220> FEATURE:
<221> NAME/KEY: misc_feature
<222> LOCATION: (8636)..(8636)
<223> OTHER INFORMATION: n is a, t, g, or c.
<220> FEATURE:
<221> NAME/KEY: misc_feature
<222> LOCATION: (8903)..(8903)
<223> OTHER INFORMATION: n is a, t, g, or c.
<220> FEATURE:
<221> NAME/KEY: misc_feature
<222> LOCATION: (8912)..(8912)
<223> OTHER INFORMATION: n is a, t, g, or c.

<400> SEQUENCE: 30
aaattaaacc aacccaaatc gatctgacaa cgaacaaaac gaactcaaag cactcacaag      60
ctcaagttca acaaagttca tcacgcagaa agcaattcgt tcattgtgag ctctcgcata     120
gagataagca atggcaacag cgaattgttt gctcggtgac ttcggaaggc aggggtcgt     180 cgctaacgac ccatatgtac agtgcagagc gcgcacgctg attttcctaa gcactgagga     240
ggaggttgat gtggtggtta accaccacgg accaggaagc attttctggt caaaagaagg     300
tatcttaaca cagacggcta agaaccttta caaagctact gcgtatggct taggctacga     360
ccttgcagca aacgtcttcg tttgcggcaa gtgtaggtcc agctgcactc agtataggta     420
cttcattgag gatcactttg cctgcgacaa actcgtggag aagaactgcg cgtacatcaa     480
ggatgataag tacgtgaagg ttgtggaggc attcccaatt atgccatctt atgccacacc     540
agggcaagaa acacgcatca tacagtggat gaacaagaca agtcaatgcc ttgctgatca     600
```

```
ctgcatccaa cgcactcgcg agatcacttt caccaactca aaaactcagg aggaagaaac    660
tcgcgtgaag gattgcagtn tggaagtntt ttatgatgac ttcgatgaag ctcatgcagt    720
gattgagcac gcacatcgga agaatccggt tcacgaatat aaggagaagc agctacggat    780
gacttcaaat aacatagctg cgttagtgga ccaagtgaca cggatgatgc actccaaggg    840
caaaacagtg gaaatagttg ggagtaaagg ccataagaaa tttgccaaaa ttccactgaa    900
gcacacaatg ggatatccaa agcgggattg ggacgcaaca aaggacatac cagaagattt    960
cagaggcttt atcacaactt atagtggcgt catacaatac acacgcaaag tgcaggatca   1020
cgaagtgacg cttggatgga gtggtgttct ncttagtgag atggatgttc ctgatggcta   1080
tcaagaagat tgcgttgacg gtctatttat tgtcatggga agatgcgcac atggacgcat   1140
tcaaaacgca ctgaagccga aatgcacaca tggatttaga tggtatggcg accaagcagt   1200
gaacaaagtn attccgaaat atcacgatgt gtgcaacaac aactgcgcaa gttacctgga   1260
agccttgcca agaaaggtta gccgtgtatg gcaatcaatg tttgacatac ataatctgag   1320
gtgcgaccaa tgtagaacag agtggaagat gcgaacagcc tcagagcatt tgcaattgtt   1380
acagaaatct gtggaacatt acatgcaaac gtatccagac agcgatgtaa cactgttcaa   1440
agcattcttg caagcactag ggccagatga agnaggttga ggcacgccag ctcaaaccca   1500
acaatacatt gcaacttgta gatgtgtggc gaacaatgaa aaacacaata acatcccga    1560
atagaatcat ctacatgggc atgttcacgg acaattatgg aaattttgat ttctttccga   1620
acacatcaat gcctgaatta ttcgccatgc acatgcaacc ggtgcaacat aagatgctag   1680
aagatggaac aattgaaacg aattttaggt tcgttgattt ggaagggaaa atccaaacta   1740
gcattgaaag tttgtatccg acatttgaca gcacatactg gaatgaacaa gcacgcagag   1800
ttcacagaat ccaaccgcta gcagactgct cgatggaaat taacggcgag tctaagccca   1860
tttgtcactg ggaaggaaat gtgcctttgt acaatcccat tattcgtgca acgcctggac   1920
aattaccgtt tggagttaca acgcatttgc tgagtgtaaa tgacaggagt ggaagattcc   1980
attatgtgcc gaagaatggg tattgttaca tgtacatatt tgcctgtgcg atgatttct    2040
gtggtaatag caatcgttcc acagttgacg cctttgttcg gcaagtntgc gaggatctgg   2100
gtccttggcc aacatttggt gatgtnctaa gacaacttga ctggatggcg acctttatg    2160
gatgttatga tgcattggtg ccagtaatct tggtagacca cacaagaaag accatgcacg   2220
tgccaacacc atatggtata aagcaatcag gaatgcatac catcagagtc aacacagtgc   2280
tagagttgat aactctcgat accatggcca gtggagcaat gaaagattac aaaattggcg   2340
ggttccaaga gacagttctn agcatacaag catgcgtcaa gagcagaaaa gaatttgtgc   2400
gcaaaatcaa caaggatgca gaatggttgg tggatatgtt tattaatcct tcaacgctct   2460
tcgtgttagg aggcttaatt gaagtgcacc aagtcattct tgctgatgtc gagaattcat   2520
tcgacaaatc agcagcttta ctaaacttgc gccaaatagc tttaaagctc ggaccacact   2580
tggaatcaaa gcagcgcgta cgtcagtaca gtggagttaat gattcagcat cgagcatcag   2640
ttgaagcaat aatcccatcg caacacatga aagctgagat gatgcaatac attgatgcac   2700
tgcaacgctc aattcttgag gagcaagtaa tcatagagat ggatcgagtt ggaggaaagg   2760
aaaaaatgct cgtcgagcaa gatctttcac acgcagagtg tgcgtacaac gagttcttca   2820
actccattgg ctacttaaac tttcatggaa ccgttttacg actcacatat tctggtccag   2880
gaagaaaggt tggagaagtg ctagagagtt aagagacaa  ctggttgaca cgctatctcc   2940
gaggaccgaa gcagccgaga gaagaaaggt tggagaagtg ctagagagtt aagagacaa   3000
```

```
ctggttgaca cgctatctcc gaggaccgaa gcagccgaga catggccgcg aacgtcttgc    3060
aagttatact cataggcctt tctaccgttt tcggagcata tttattaaag aagatcttaa    3120
aaatgctgca gtgggagaag gagcaagaaa gcaccgaatt ggttgaatac caagggaagc    3180
gagaggaagc atggataaca cgagtaatgg ctgtattgta tataatagct tcacttttct    3240
ccgtagattt tagttctgct ttatattcga atttggtgaa gttcagaacc atatttgaca    3300
tnttgaagtt taattgcgaa tatcagagtg gaattttga aagtttgaaa aatcaactcg     3360
gcaacatccc agcgtttcat gaggtacatt tgtatgacca tgaggcaaca caagtagcag    3420
tnccaccagc natattgaca ttcgagcgat ggttcgagac tcggatcaca tctggccagc    3480
aaggatatgc accacttgat ggtagccacg tgagcttaac gatgacaaaa gacacagttg    3540
gtganatcgc aacacaagtg caaacgcaca aggcaaagga gtttctcatt ataggacatg    3600
ttggatgtgg aaaatctaca gcttttccag caacactctc ccggaatggg cgtgtgatga    3660
tatgcgaacc aacccgcgtg ctagtnacaa atttgcagga ttcaatgcta gcaacgaaga    3720
atctaagtat cagtgccatg atgagaaacc accgggttat gacggcgtcg aatataacag    3780
taactacgta tgggtatgca ctccactact tgtacaacaa ctcacataac ctttcagagt    3840
atgattatat tcttttgac gaagtgcacc aaacctcggc agagatgcta gtgttttaca    3900
actggcttaa gagcacaacg tgggagggca agctcatcaa gttaacagcc acgaacaaca    3960
cagttaatgg cgacatgcaa acacagcaag cccttgatgt caaaacgtgg ccggttatgg    4020
atcacagaac attcatgcag gagcaaggtc gaggaacggc tcacgatgca tcaactcttg    4080
gtgatgtcat catagtcttc ttaacttcgt ttcgtgaaat tgatgaatct gctgatattt    4140
taagcaaaaa ttcaaagatt ggcgtaataa aggcagatag tcggcacttg cgaaacaaag    4200
ttagcttgat ggatgatgtt gaagcactcc gagctgagaa gaaatacatt cttgcaacta    4260
atattcttca aaacggtgtg aatttgcatg cagacgttgt cgttgatttt ggcttcaaga    4320
ttgtaccagc cattgacagc gacaatcgga tgatcacagt caagcgccaa ttgatcaaca    4380
aatcagacag gattcagaga ctaggacgag tnggccggat gaagatggga tacgcaagga    4440
aaatcggaaa tgaaatagat gcntcattcg ctttggatga agtcacagct acggaagctg    4500
ccttgttggc atttggactc ggtgttgctc cagtgttgca gaatgttgat caacacacat    4560
tcggaaaaat aacagcagag caagttcgaa cagctgcacg ctttgaaatg caattgtcgt    4620
atatggtgtg gatgatnaac agagatggca ctatggccac acggttatat gaacaattca    4680
agtcattgct tttaacacca ggaaacacga gtttggctcc gtattacgag acactcgttg    4740
acactcacag attcagaact attggacaat acgcaactct tggatacatg cgcacagacg    4800
aaaagcacca tttggtatta ccatttcacc ataatgacgt gagcgttgaa tttgcngaaa    4860
ggattggcga agcctatatg gcctctcaag tcccaacatc aatcaagttg cgcgtacctg    4920
cngtnaatca tagagaagtg gcgatgaaga tgtcagcaaa tcctgaagat gtgggaacca    4980
tattgtatat ggttgagcaa gcgctaataa gtgaaaagac gaaactggag aatctaacnc    5040
aggcattcca gcagcaacaa tcaacatatt gcagcgtgct cattcctaat ttcaatgttg    5100
ctggtcggct aacacaggca atggatcgca taagaaagaa tgtttctgtg ctncaacacc    5160
agaaaacagc tctcgaaaag gcngcagtga cttacgacta cacgaagtta gttgagctcc    5220
ttgatgaaaa tccaagcata gcttcccatg tgtcatacca ggctgggcca gcaaaattca    5280
ttgatgaatt catattggag aagcgcgatt atgggtggct accatatctt gcagtaggaa    5340
ctgcgtgtgc aattgctggc acaacacttg tgatgatgta ctaccgtcgc atgaagcgta    5400
```

```
gtgtcaagtt cgagggcaaa gcagcacgca acaggagtgc aaaacgacaa tcagcaagag   5460
accaaaagat ggagcgtggc aacgaataca catactacga tgctggtgac accttgtata   5520
atggagttca agagaatatg aatcatgcac cagactggac cgatcggatt aagaagaaga   5580
ctcatgcata cgcaatgcaa tttggtaggg aagtaccaaa gactgaaaca cagcgatcnt   5640
cncaatactg gcacttctac ggttttgatc caaagatgta tgattcagtc gaattcaagg   5700
acatagcagc aaacttctca gtgcaccagg atgcaaaggc aatggatttg cagaaagcct   5760
tcacagaaat ggtggaaaat cgttgggatg atgaagactt cttcgacgag aagataccaa   5820
agcgagtttt ggccatcttc aggaaaggag acaaggttcg tgaagttgca ttggcacctc   5880
acaagccaaa ccaagtcaac aagcgtgggc tacctgtcgg acatgctgat cacagaggag   5940
agtggagaca aacacagcct tcatttgaaa agaagtgtc gtacgagaac aaatcaactt   6000
tcgaaggtgc acgttcactt gatcatatcc atcagaatca agtcatcctc gttgaagaca   6060
atcagcagtt aaatgggcta atagttggna acatactctt ggcgccatat catttcacac   6120
gaggtatgag gaacagagag gagaaggaaa cacgcatgtt gacacagttt ggaacgtaca   6180
atcttggaaa acttaccaac aagcatgtca caaaatttac aatgatggat ctggtagcat   6240
taaccttacc tccaacattt caagcaagac ggaaactcaa atgtttcaga ccaccaaggg   6300
aaggagagcg agcaatgttg gtgaccatgc agtacgagaa agcaggatgg gttgccaagc   6360
aatcagcgga aacaacaatc acaccattcg gtgatcgaca tgatggtttg tggaagcata   6420
gaatttcaac aggaccaggt gactgtgaa gcgccatagt agcagtagca gacctaaaag   6480
ttgttggatt ccataacctt ggagggaaag gtgagaatta cttcacaccg ataactattg   6540
aggtcatgga tttcttagct gaaaagtctg tgacaccgct tgtgccatgg aagttctcag   6600
acgagcaagt tgacttgtgt ggtttaattg cggccaatgg agcagacaaa tacccattca   6660
ccaaaacaat aagcgacttg gttagttggc aaagtctcca aatgacgaaa tactgtgggg   6720
agaacttcaa ggctatcgct tatgctccaa accgaatgtc aaaaaggcat gtcataacag   6780
gaaagaggcc tgaattcatt aaatttctag attcccaccc gaagtggaat gcantggtaa   6840
cacctttctt aaacgaattt caaccatcag ttctgacaca tgaagcatat tacaaggatg   6900
tgttgaagta taacaaagac ataattgttg gagggactga tgaagtgtgt tttgcgaagg   6960
cagtggtcgc aaccattggg attctagaaa tagccggatt ttcaaaggga caatttcaac   7020
caatctttga tggatgtaaa attttcaacg acttgaattt ggatgccgca atgggagctt   7080
tgtactcagg gaagaaatcn gcatactttg acggagcaac aagcgacgaa atcaatgaat   7140
tctttgaact gagtgcagcg aagctactca gtaatggaca tggagtatgg tctggtttac   7200
tcaaagctga gttgagaccg aaggcaaagg tcgtggcgaa caaaacgcga acattcacat   7260
cagcaccaat tgatatactc atgggtgcca aagctgtggt tgatgagttc aacaaattct   7320
tctacacaaa gcatttgcgc ggaccatgga cngtcggcat caataagttc aacggaggtt   7380
gggatttgtt ggccaaaaat ctaatggtgc acgagtggtt cattgacgct gatggttctc   7440
aattcgacag ttcaatcact ccacttctga tgaatgcaat tcttaacata cggcaatact   7500
tcatggcaga agatgatgaa gctgaacaaa tgctggcaaa tttgtatacg cagattataa   7560
acacatgcat tttaattgaa gatggaacga ttgtgcagaa gttctcgaggt aataacagtg   7620 gccaaccaag cacagttgtt gacaacacga tgtgtttaat catagcaatg gagtattgca   7680
gaatgcgcgt ngaaaaggat catggacata gaatgaggat actgtacgtg tgcaacggag   7740
atgatttgct tatcaatgcc gacacaaagg acaaagactt catacagcag tattttgccg   7800
```

```
attacatgcg cgaactggag ctgaattact catttgacga ggcttaccgt agtatcgagg    7860
aggtggaata catgtcacac acatttatga agcgaaattc gatgtacatt ccaaagttga    7920
agcgcgaacg nattgtggca attctggagt ggcagaggag caaggaaccg aaggctattc    7980
agagcgctat tattgcagca tacgtggaag ctttcggtta tgatgaattc acggagatga    8040
ttgaagaact tgcgcaggaa gtttcagcgg tgtggccaga tttcaagttg ccctcacgac    8100
aagaggttga ggatttgtac ttgactggga cccgaacgga tttaggagaa gagattaagg    8160
aatgtggaga gcaatactgc gtgtacgaat cgagtgaggc cgcaaccgac gctgtcttgg    8220
cggcagcaaa tgcaggaact ggtagtgcat cgagcagtgg aagnactcan tcaagtcnga    8280
gcgcaagtac tgctagcgga tcagggagnt caccatcagg atcaggttct ggagcagcgg    8340
gtggatcagg ttctggatca gcacaaacac aatctaataa cgtatctgtc atggctggcc    8400
tcgacacggg aggagctaag acaggtcaag gatcaggatc aaaagggacg ggtggttcat    8460
tcatatcgaa tcccgtgcga actggaggcc gagcaacgga tgtgcaagat cagacaccag    8520
gnttagtgtt tccagcacca aagatcacaa caaaggccat atacatgcca aaaactgtac    8580
gcgacaagat aaagcctgaa atgataaata acatgatcaa ataccaaccg cgtgcngaac    8640
ttatcgacaa cagatatgcc acaactgaac aactcaacac ctggataaaa gaggcatctg    8700
aagggcttga cgtgacagag gatgttttca taaacacctt acttccagga tgggtctacc    8760
actgcataat caacacaacg agcccagaga acagagcact aggaacttgg cgtgttgtga    8820
ataatgcagg caaggacaat gagcagcaac tcgagtttaa gattgaaccg atgtacaaag    8880
ctgcgaagcc atcacttcga gcnattatgc gncactttgg cgagggagct cgagtgatga    8940
tcgaggagag tgttcgaatt ggaaaaccta tcataccaag gggcttcgac aaggccggtg    9000
tgctaagcat caacaatatt gtggcagcgt gtgatttcat catgcgcggt gcagatgaca    9060
caccaaattt tgtgcaagtg cagaacagcg ttgcagtgaa caggctacgc ggaatacaga    9120
acaagctgtt tgcacaggca cgactgagtg cgggtactaa tgaggacaac tcacgtcatg    9180
atgcagatga tgtgagggag aacacgcaca gtttcaatgg tgtaaacgct cttgcgtgag    9240
cacagtagaa actacaaatc cacgagtacc aggatttgag cgaaataacg ctgcgtttcg    9300
ttaacccttc gttgttacta ggtgtgtact tctccacgag aggcgtgcat tcttggtagc    9360
tatgtgtggg ttagggcgac gctac                                         9385
```

<210> SEQ ID NO 31
<211> LENGTH: 770
<212> TYPE: DNA
<213> ORGANISM: Artificial
<220> FEATURE:
<223> OTHER INFORMATION: Natural miR395 sequence (truncated) encoding five native miRNAs in rice.

<400> SEQUENCE: 31

```
agtcaaaatt tggttggttg tccactggag ttctcctcaa tccacttcag tagatagcta     60
tggctaggcc tcattgcatt gcactgttac ataactgtga tcatgggggcc aaaagctagc    120 tatgtatagt gaagtgcttg ggggaactcc agttgacact cagcattttc aagttaggta    180
tgtaagtgct tgtactttat gaatttgtaa gtgacagaga atgattaggt ttggagtccc    240
taggagttcc tttcaagcac tttacgacac actgtattga gagttgtcgt gaagtgtttg    300
ggggaactct tagtgtcgcc aagcatttaa gtagatagtg tttaaactac aagaaatgag    360
agaaacgttt ggtattatca agagttctct ttaagcactt catacgacac cattatttat    420
```

```
agggttgttg tgaagtgttt ggaggaactc tcggtgtcat caaacaatta gtagatagtg      480
tttaaaccac aagactgaga gccacgtttg gtattgtcgt gagttccctt caagcacttc      540
acgtggcact atctcaatgc ctactatgtg aagtgtttgg gggaactctc gatatcacca      600
aacattcaac atatagtgtt taaacacgag attgagatgg gagccacttt tggtattatc      660
gagagttccc ttcaaccact tcacgtggca ctgtttcaag gcctattgtg tgaagtgttt      720
gggggaactc tcgatatcac caaacattta atgtagtgct taaaccacaa                 770

<210> SEQ ID NO 32
<211> LENGTH: 764
<212> TYPE: DNA
<213> ORGANISM: Artificial
<220> FEATURE:
<223> OTHER INFORMATION: Modified miR395 sequence encoding five amiRNAs
      targeting WSMV

<400> SEQUENCE: 32
agtcaaaatt tggttggttg tccactggct tatctctatg cgagagctgt agatagctat       60
ggctaggcct cattgcattg cactgttaca taactgtgat catggggcca aaagctagct      120
atgtataagc tctcgcatag agataagcca gttgacactc agcattttca agttaggtat      180
gtaagtgctt gtactttatg aatttgtaag tgacagagaa tgattaggtt tggagtccct      240
agcgtgtgaa agatcttgct cgacgacaca ctgtattgag agttgtctcg agcaagatct      300
ttcacacgtt agtgtcgcca agcatttaag tagatagtgt ttaaactaca agaaatgaga      360
gaaacgtttg gtattatcaa ccaggaagca ttttctggtc aacgacacca ttatttatag      420
ggttgtttga ccagaaaatg cttcctggtc ggtgtcatca acaattagt agatagtgtt       480 taaaccacaa gactgagagc cacgtttggt attgtcgtcc gcgaacgtct tgcaagttag      540
tggcactatc tcaatgccta ctattaactt gcaagacgtt cgcggtcgat atcaccaaac      600
attcaacata tagtgtttaa acacgagatt gagatgggag ccacttttgg tattatcgag      660
aagattccat tatgtgccga gtggcactgt ttcaaggcct attgttcggc acataatgga      720
atcttcgata tcaccaaaca tttaatgtag tgcttaaacc acaa                       764
```